(12) United States Patent
Blackmon et al.

(10) Patent No.: US 12,349,728 B2
(45) Date of Patent: Jul. 8, 2025

(54) HEAT-NOT-BURN (HNB) AEROSOL-GENERATING DEVICES AND CAPSULES

(71) Applicant: Altria Client Services LLC, Richmond, VA (US)

(72) Inventors: Zack W. Blackmon, Richmond, VA (US); Eric Hawes, Midlothian, VA (US); Dean Twite, London (GB); Rangaraj S. Sundar, Midlothian, VA (US); Nicolas D. Castro, Richmond, VA (US); Raymond W. Lau, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 18/440,298

(22) Filed: Feb. 13, 2024

(65) Prior Publication Data
US 2024/0180243 A1  Jun. 6, 2024

Related U.S. Application Data

(63) Continuation of application No. 17/151,340, filed on Jan. 18, 2021, now Pat. No. 11,910,826.

(51) Int. Cl.
*A24F 40/40* (2020.01)
*A24F 40/20* (2020.01)
(Continued)

(52) U.S. Cl.
CPC .............. *A24F 40/40* (2020.01); *A24F 40/20* (2020.01); *A24F 40/53* (2020.01)

(58) Field of Classification Search
CPC .......... A24F 40/20; A24F 40/40; A24F 40/42; A24F 40/46
See application file for complete search history.

(56) References Cited

U.S. PATENT DOCUMENTS 855,984 A    6/1907 Russell
1,071,389 A  8/1913 Blosser
(Continued)

FOREIGN PATENT DOCUMENTS

CN   103945716 A    7/2014
CN   203986136 U   12/2014
(Continued)

OTHER PUBLICATIONS

Crafty Vaporizer manual (2014).
International Search Report and Written Opinion for PCT/US2021/060519 dated Apr. 13, 2022.

*Primary Examiner* — Abdullah A Riyami
*Assistant Examiner* — Thang H Nguyen
(74) *Attorney, Agent, or Firm* — Harness, Dickey & Pierce, P.L.C.

(57) ABSTRACT

A capsule may include a housing, an aerosol-forming substrate, and a heater. The housing defines inlet openings, outlet openings, and a chamber between the inlet openings and the outlet openings. The chamber may have a longest dimension extending from at least one of the inlet openings to a corresponding one of the outlet openings. The aerosol-forming substrate is within the chamber of the housing. The heater is embedded in the housing. The heater includes a first end section, an intermediate section, and a second end section. The intermediate section is disposed within the aerosol-forming substrate in the chamber. An aerosol-generating device may include a device body with a lid configured to open to permit an insertion of the capsule and configured to close to engage the capsule within the device body.

20 Claims, 37 Drawing Sheets

(51) Int. Cl.
    *A24F 40/485*     (2020.01)
    *A24F 40/53*     (2020.01)

(56) References Cited

U.S. PATENT DOCUMENTS

| | | | |
|---|---|---|---|
| 1,934,887 A | 11/1933 | Robinson | |
| 4,214,146 A | 7/1980 | Schimanski | |
| 4,564,748 A | 1/1986 | Gupton | |
| 4,947,874 A | 8/1990 | Brooks et al. | |
| 5,388,572 A | 2/1995 | Mulhauser et al. | |
| 5,388,573 A | 2/1995 | Mulhauser et al. | |
| 5,441,060 A | 8/1995 | Rose et al. | |
| 5,460,173 A | 10/1995 | Mulhauser et al. | |
| 5,593,792 A | 1/1997 | Farrier et al. | |
| 5,619,984 A | 4/1997 | Hodson et al. | |
| 5,645,050 A | 7/1997 | Zierenberg et al. | |
| 5,665,262 A | 9/1997 | Hajaligol et al. | |
| 5,823,182 A | 10/1998 | Van Oort | |
| 6,006,747 A | 12/1999 | Eisele et al. | |
| 6,065,472 A | 5/2000 | Anderson et al. | |
| 6,095,153 A | 8/2000 | Kessler et al. | |
| 6,481,437 B1 | 11/2002 | Pate | |
| 7,186,958 B1 | 3/2007 | Nelson | |
| 7,997,280 B2 | 8/2011 | Rosenthal | |
| 8,488,952 B2 | 7/2013 | Landry | |
| 8,490,627 B2 | 7/2013 | Levin et al. | |
| 8,714,150 B2 | 5/2014 | Alelov | |
| 8,910,630 B2 | 12/2014 | Todd | |
| 9,072,322 B2 | 7/2015 | Liu | |
| 9,549,573 B2 | 1/2017 | Monsees et al. | |
| 9,693,587 B2 | 7/2017 | Plojoux et al. | |
| 9,756,876 B2 | 9/2017 | Liu | |
| 9,775,379 B2 | 10/2017 | Davidson et al. | |
| 9,943,114 B2 | 4/2018 | Batista | |
| 9,980,522 B1 | 5/2018 | Heidl et al. | |
| 9,986,767 B2 | 6/2018 | Batista et al. | |
| 9,999,258 B2 | 6/2018 | Newcomb et al. | |
| 10,015,990 B2 | 7/2018 | Mironov | |
| 10,045,567 B2 | 8/2018 | Monsees et al. | |
| 10,058,129 B2 | 8/2018 | Monsees et al. | |
| 10,058,130 B2 | 8/2018 | Monsees et al. | |
| 10,064,432 B2 | 9/2018 | Hawes et al. | |
| 10,076,139 B2 | 9/2018 | Monsees et al. | |
| 10,099,020 B2 | 10/2018 | Davidson et al. | |
| 10,104,913 B2 | 10/2018 | Lau et al. | |
| 10,111,470 B2 | 10/2018 | Monsees et al. | |
| 10,130,124 B2 | 11/2018 | Wong et al. | |
| 10,149,498 B2 | 12/2018 | Batista et al. | |
| 10,172,390 B2 | 1/2019 | Nakano et al. | |
| 10,179,215 B2 | 1/2019 | Raichman | |
| 10,201,190 B2 | 2/2019 | Monsees et al. | |
| D843,649 S | 3/2019 | Rasmussen et al. | |
| 10,219,543 B2 | 3/2019 | Gill et al. | |
| 10,247,443 B2 | 4/2019 | Flick | |
| 10,251,423 B2 | 4/2019 | Mamoun et al. | |
| 10,271,578 B2 | 4/2019 | John et al. | |
| 10,278,424 B2 | 5/2019 | Garthaffner et al. | |
| 10,292,436 B2 | 5/2019 | Cirillo et al. | |
| 10,314,343 B2 | 6/2019 | Newcomb et al. | |
| 10,321,716 B2 | 6/2019 | Zitzke | |
| 10,328,443 B2 | 6/2019 | Ricketts et al. | |
| 10,433,585 B2 | 10/2019 | Tucker et al. | |
| 10,485,269 B2 | 11/2019 | Hawes et al. | |
| D870,368 S | 12/2019 | Leon Duque et al. | |
| 10,492,529 B2 | 12/2019 | Borkovec et al. | |
| 10,524,512 B2 | 1/2020 | Sebastian et al. | |
| 10,555,560 B2 | 2/2020 | Bilat et al. | |
| 10,588,357 B2 | 3/2020 | Hawes et al. | |
| 10,602,776 B2 | 3/2020 | Batista | |
| 10,624,394 B2 | 4/2020 | Memari et al. | |
| 10,645,971 B2 | 5/2020 | Zitzke | |
| 10,667,557 B2 | 6/2020 | Mironov et al. | |
| 10,667,560 B2 | 6/2020 | Atkins et al. | |
| 10,674,770 B2 | 6/2020 | Talon | |
| 10,701,975 B2 | 7/2020 | Bowen et al. | |
| 10,701,981 B2 | 7/2020 | Newcomb et al. | |
| 10,709,173 B2 | 7/2020 | Monsees et al. | |
| 10,721,967 B2 | 7/2020 | Raichman | |
| D893,096 S | 8/2020 | Leon Duque et al. | |
| 10,757,972 B2 | 9/2020 | Matsumoto et al. | |
| 10,757,975 B2 | 9/2020 | Batista et al. | |
| 10,772,354 B2 | 9/2020 | Batista | |
| 10,820,629 B1* | 11/2020 | O'Connell | A24B 15/167 |
| 10,905,835 B2 | 2/2021 | Atkins et al. | |
| 12,201,148 B2* | 1/2025 | Blackmon | A24F 40/20 |
| 2004/0159322 A1 | 8/2004 | Kladders et al. | |
| 2005/0063686 A1 | 3/2005 | Whittle et al. | |
| 2007/0045288 A1 | 3/2007 | Nelson | |
| 2007/0102013 A1 | 5/2007 | Adams et al. | |
| 2008/0073558 A1 | 3/2008 | Howell et al. | |
| 2009/0293888 A1 | 12/2009 | Williams et al. | |
| 2009/0293892 A1 | 12/2009 | Williams et al. | |
| 2010/0012118 A1 | 1/2010 | Storz | |
| 2010/0059070 A1 | 3/2010 | Potter et al. | |
| 2010/0078022 A1 | 4/2010 | Striebig et al. | |
| 2010/0139655 A1 | 6/2010 | Genosar et al. | |
| 2010/0313901 A1 | 12/2010 | Fernando et al. | |
| 2011/0126848 A1 | 6/2011 | Zuber et al. | |
| 2011/0192399 A1 | 8/2011 | Wilke et al. | |
| 2012/0304990 A1 | 12/2012 | Todd | |
| 2012/0325227 A1 | 12/2012 | Robinson et al. | |
| 2013/0032145 A1 | 2/2013 | Adler et al. | |
| 2013/0186392 A1 | 7/2013 | Haartsen et al. | |
| 2013/0233309 A1 | 9/2013 | Todd | |
| 2013/0233312 A1 | 9/2013 | Cohn | |
| 2013/0255702 A1 | 10/2013 | Griffith, Jr. et al. | |
| 2013/0276799 A1 | 10/2013 | Davidson et al. | |
| 2014/0041655 A1 | 2/2014 | Barron et al. | |
| 2014/0060554 A1 | 3/2014 | Collett et al. | |
| 2014/0186015 A1 | 7/2014 | Breiwa, III et al. | |
| 2014/0217197 A1 | 8/2014 | Selby et al. | |
| 2014/0238423 A1 | 8/2014 | Tucker et al. | |
| 2014/0299141 A1 | 10/2014 | Flick | |
| 2014/0321837 A1 | 10/2014 | Flick | |
| 2014/0345606 A1 | 11/2014 | Talon | |
| 2014/0366609 A1 | 12/2014 | Beck et al. | |
| 2015/0059747 A1 | 3/2015 | Von Schuckmann | |
| 2016/0021932 A1 | 1/2016 | Silvestrini et al. | |
| 2016/0057811 A1 | 2/2016 | Alarcon et al. | |
| 2016/0295922 A1 | 10/2016 | John et al. | |
| 2016/0316817 A1 | 11/2016 | Liu | |
| 2016/0324216 A1 | 11/2016 | Li et al. | |
| 2016/0331913 A1* | 11/2016 | Bourque | A61M 15/0098 |
| 2016/0338410 A1 | 11/2016 | Batista et al. | |
| 2016/0345630 A1* | 12/2016 | Mironov | B32B 3/266 |
| 2016/0366947 A1 | 12/2016 | Monsees et al. | |
| 2017/0055584 A1* | 3/2017 | Blandino | A24F 40/00 |
| 2017/0071251 A1 | 3/2017 | Goch | |
| 2017/0095624 A1* | 4/2017 | Davidson | A61P 25/22 |
| 2017/0119979 A1 | 5/2017 | Davidson et al. | |
| 2017/0143042 A1 | 5/2017 | Batista et al. | |
| 2017/0144827 A1* | 5/2017 | Batista | B65D 17/501 |
| 2017/0164657 A1* | 6/2017 | Batista | A24F 40/42 |
| 2017/0196262 A1 | 7/2017 | Brereton et al. | |
| 2017/0231276 A1 | 8/2017 | Mironov et al. | |
| 2017/0311648 A1* | 11/2017 | Gill | A24F 40/50 |
| 2017/0347711 A1 | 12/2017 | Litten et al. | |
| 2018/0007960 A1 | 1/2018 | Suzuki et al. | |
| 2018/0042302 A1* | 2/2018 | Robinson | A61M 15/06 |
| 2018/0077967 A1 | 3/2018 | Hatton et al. | |
| 2018/0084831 A1 | 3/2018 | Mironov | |
| 2018/0104214 A1 | 4/2018 | Raichman | |
| 2018/0214645 A1* | 8/2018 | Reevell | A24F 40/53 |
| 2018/0235279 A1* | 8/2018 | Wilke | H05B 3/58 |
| 2018/0242644 A1 | 8/2018 | Bessant et al. | |
| 2018/0243520 A1 | 8/2018 | Johnson et al. | |
| 2018/0263286 A1* | 9/2018 | Reevell | B01F 23/2133 |
| 2018/0295885 A1 | 10/2018 | Rojo-Calderon et al. | |
| 2018/0361334 A1 | 12/2018 | Bahabri | |
| 2019/0046745 A1* | 2/2019 | Nettenstrom | A61M 15/002 |
| 2019/0098930 A1 | 4/2019 | Fallon et al. | |
| 2019/0099561 A1 | 4/2019 | Nettenstrom | |
| 2019/0117915 A1 | 4/2019 | Raichman | |
| 2019/0166913 A1 | 6/2019 | Trzecieski | |

(56) References Cited

U.S. PATENT DOCUMENTS

| | | |
|---|---|---|
| 2019/0174827 A1 | 6/2019 | Fernando et al. |
| 2019/0208823 A1 | 7/2019 | Raichman |
| 2019/0208826 A1 | 7/2019 | John et al. |
| 2019/0224430 A1 | 7/2019 | Raichman |
| 2019/0254348 A1 | 8/2019 | Garthaffner et al. |
| 2019/0350256 A1 | 11/2019 | Hejazi |
| 2020/0037669 A1* | 2/2020 | Bowen ............... A24F 40/46 |
| 2020/0054076 A1 | 2/2020 | Lau et al. |
| 2020/0077702 A1 | 3/2020 | Mishra et al. |
| 2020/0085099 A1 | 3/2020 | Soriano et al. |
| 2020/0120988 A1 | 4/2020 | Qiu |
| 2020/0214343 A1 | 7/2020 | Fursa |
| 2020/0229507 A1 | 7/2020 | Flora et al. |
| 2020/0229509 A1* | 7/2020 | Griscik ............... A24D 1/14 |
| 2020/0236997 A1 | 7/2020 | Mironov et al. |
| 2020/0245680 A1 | 8/2020 | Williams |
| 2020/0246563 A1 | 8/2020 | Raichman |
| 2020/0260785 A1 | 8/2020 | Bowen et al. |
| 2020/0281249 A1 | 9/2020 | Sebastian et al. |
| 2020/0281269 A1* | 9/2020 | Malgat ............... A24F 40/70 |
| 2020/0297030 A1 | 9/2020 | Newcomb et al. |
| 2020/0329773 A1 | 10/2020 | Habicht et al. |
| 2020/0352239 A1 | 11/2020 | Batista |
| 2020/0375254 A1 | 12/2020 | Mironov et al. |
| 2020/0390149 A1* | 12/2020 | Hepworth .......... A24F 40/465 |
| 2021/0015148 A1 | 1/2021 | Shenton et al. |
| 2021/0015153 A1 | 1/2021 | Raichman |
| 2021/0022395 A1 | 1/2021 | Moloney |

FOREIGN PATENT DOCUMENTS

| | | |
|---|---|---|
| CN | 104349687 A | 2/2015 |
| CN | 110200329 A | 9/2019 |
| EP | 0525720 A1 | 2/1993 |
| EP | 1007124 A1 | 6/2000 |
| EP | 1029451 A1 | 8/2000 |
| EP | 1385595 A2 | 2/2004 |
| EP | 1504768 A1 | 2/2005 |
| EP | 3033953 A1 | 6/2016 |
| EP | 3100622 A1 | 12/2016 |
| EP | 3166429 A1 | 5/2017 |
| EP | 3166425 B1 | 6/2018 |
| EP | 3435798 A1 | 2/2019 |
| EP | 3313212 B1 | 4/2019 |
| EP | 3528592 A1 | 8/2019 |
| EP | 3539599 A1 | 9/2019 |
| EP | 3068246 B1 | 4/2020 |
| EP | 3462932 B1 | 4/2020 |
| EP | 3166430 B1 | 9/2020 |
| EP | 3708011 A1 | 9/2020 |
| EP | 3711614 A1 | 9/2020 |
| EP | 3714714 A1 | 9/2020 |
| EP | 3232840 B1 | 11/2020 |
| EP | 3484315 B1 | 12/2020 |
| EP | 3508080 B1 | 1/2021 |
| EP | 3549464 B1 | 2/2021 |
| EP | 3504989 B1 | 6/2021 |
| EP | 3430921 B1 | 8/2021 |
| EP | 3498115 B1 | 9/2021 |
| KR | 101319228 B1 | 10/2013 |
| RU | 2536115 C2 | 12/2014 |
| WO | WO-2003/037306 A2 | 5/2003 |
| WO | WO-2015/116934 A1 | 8/2015 |
| WO | WO-2015/117700 A1 | 8/2015 |
| WO | WO-2016/001921 A2 | 1/2016 |
| WO | WO-2016/001922 A1 | 1/2016 |
| WO | WO-2016/001923 A2 | 1/2016 |
| WO | WO-2016/001924 A2 | 1/2016 |
| WO | WO-2016/001925 A1 | 1/2016 |
| WO | WO-2016/001926 A1 | 1/2016 |
| WO | WO-2016/005533 A1 | 1/2016 |
| WO | WO-2016/026219 A1 | 2/2016 |
| WO | WO-2016/107763 A1 | 7/2016 |
| WO | WO-2016/172448 A1 | 10/2016 |
| WO | WO-2017/163045 A1 | 9/2017 |
| WO | WO-2018/211252 A1 | 11/2018 |
| WO | WO-2018/217440 A1 | 11/2018 |
| WO | WO-2019/030115 A1 | 2/2019 |
| WO | WO-2019/46315 A1 | 3/2019 |
| WO | WO-2019/048880 A1 | 3/2019 |
| WO | WO-2019/068441 A1 | 4/2019 |
| WO | WO-2019/128551 A1 | 7/2019 |
| WO | WO-2019/162497 A1 | 8/2019 |
| WO | WO-2019/162498 A1 | 8/2019 |
| WO | WO-2019/162500 A1 | 8/2019 |
| WO | WO-2019/162502 A1 | 8/2019 |
| WO | WO-2019/162503 A1 | 8/2019 |
| WO | WO-2019/162504 A1 | 8/2019 |
| WO | WO-2019/162506 A1 | 8/2019 |
| WO | WO-2019/162507 A1 | 8/2019 |
| WO | WO-2019/162508 A1 | 8/2019 |
| WO | WO-2019/200194 A1 | 10/2019 |
| WO | WO-2019/215039 A1 | 11/2019 |
| WO | WO-2019/224382 A1 | 11/2019 |
| WO | WO-2019/238819 A1 | 12/2019 |
| WO | WO-2020/025433 A1 | 2/2020 |
| WO | WO-2020/029923 A1 | 2/2020 |
| WO | WO-2020/056776 A1 | 3/2020 |
| WO | WO-2020/089054 A1 | 5/2020 |
| WO | WO-2020/101198 A1 | 5/2020 |
| WO | WO-2020/115322 A1 | 6/2020 |
| WO | WO-2020/142003 A1 | 7/2020 |
| WO | WO-2020/210821 A1 | 10/2020 |
| WO | WO-2020/221815 A1 | 11/2020 |
| WO | WO-2020/223875 A1 | 11/2020 |
| WO | WO-2020/223876 A1 | 11/2020 |
| WO | WO-2020/264362 A1 | 12/2020 |
| WO | WO-2021/262265 A1 | 12/2021 |

* cited by examiner

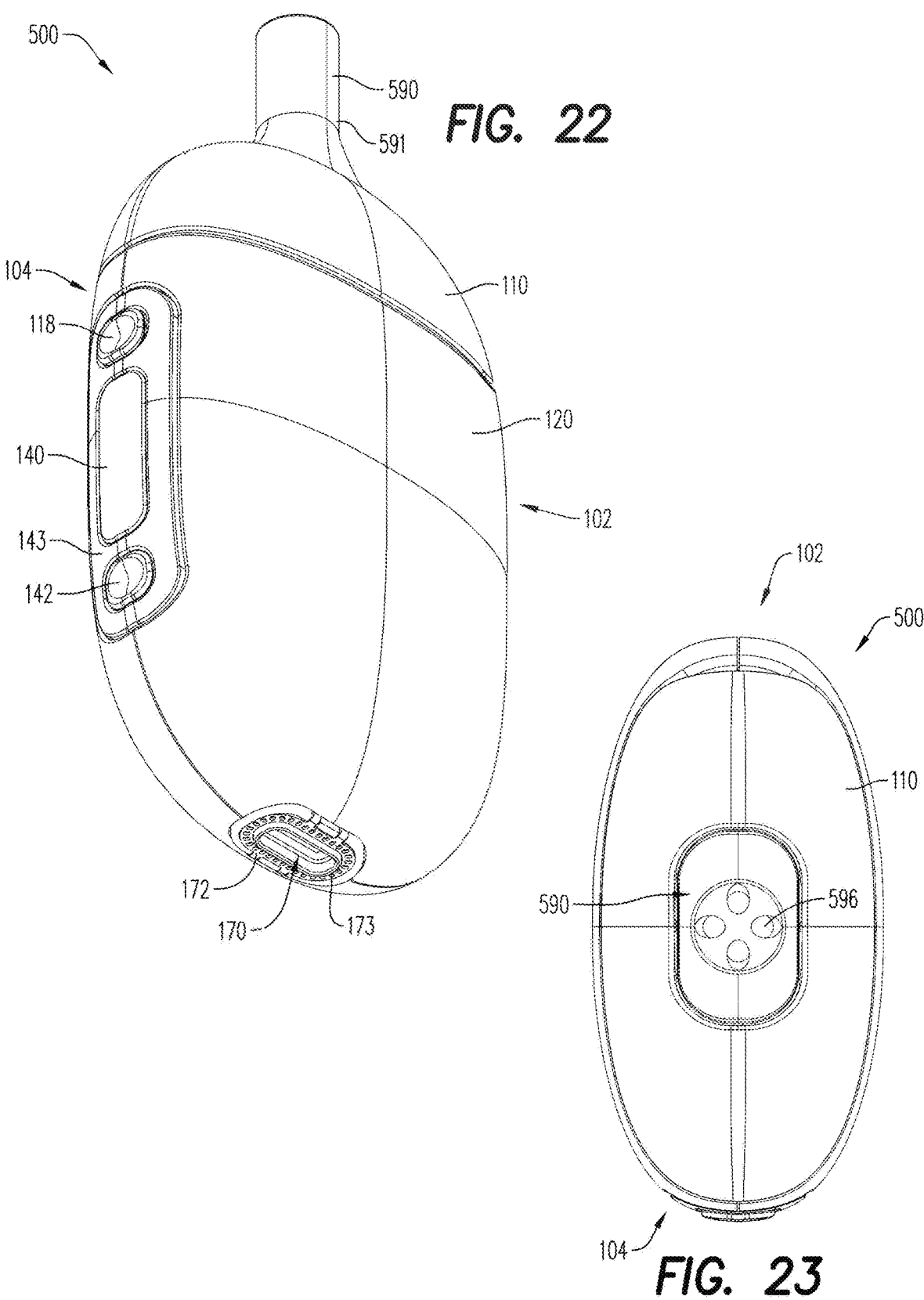

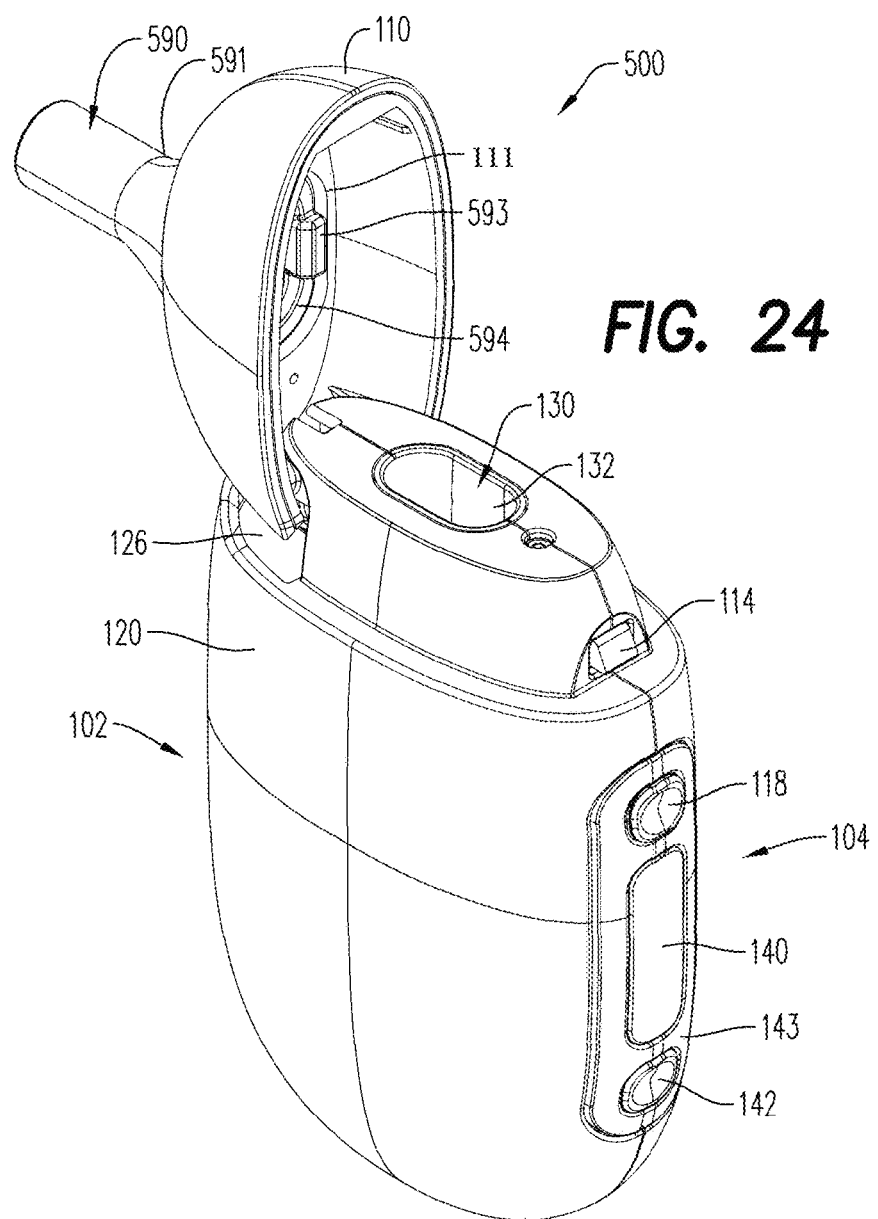

1860"

== HEAT-NOT-BURN (HNB) AEROSOL-GENERATING DEVICES AND CAPSULES

CROSS-REFERENCE TO RELATED APPLICATION

This application is a continuation under 35 U.S.C. § 120 of U.S. application Ser. No. 17/151,340, filed on Jan. 18, 2021, the entire contents of which are hereby incorporated by reference.

BACKGROUND

Field

The present disclosure relates to heat-not-burn (HNB) aerosol-generating devices and capsules configured to generate an aerosol without involving a substantial pyrolysis of an aerosol-forming substrate.

Description of Related Art

Some electronic devices are configured to heat a plant material to a temperature that is sufficient to release constituents of the plant material while keeping the temperature below a combustion point of the plant material so as to avoid any substantial pyrolysis of the plant material. Such devices may be referred to as aerosol-generating devices (e.g., heat-not-burn aerosol-generating devices), and the plant material heated may be tobacco and/or cannabis. In some instances, the plant material may be introduced directly into a heating chamber of an aerosol-generating device. In other instances, the plant material may be pre-packaged in individual containers to facilitate insertion and removal from an aerosol-generating device.

SUMMARY

At least one embodiment relates to a capsule for a heat-not-burn (HNB) aerosol-generating device. In an example embodiment, the capsule may include a housing defining inlet openings, outlet openings, and a chamber between the inlet openings and the outlet openings, the chamber having a longest dimension extending from at least one of the inlet openings to a corresponding one of the outlet openings; an aerosol-forming substrate within the chamber of the housing; and a heater embedded in the housing, the heater including a first end section, an intermediate section, and a second end section, the intermediate section being disposed within the aerosol-forming substrate in the chamber.

At least one embodiment relates to a heat-not-burn (HNB) aerosol-generating device. In an example embodiment, the aerosol-generating device may include a capsule including a housing, an aerosol-forming substrate, and a heater embedded in the housing and the aerosol-forming substrate; and a device body including a lid configured to open to permit an insertion of the capsule and configured to close to engage the capsule within the device body.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 22 is a bottom right, front perspective view of the aerosol-generating device illustrated in FIG. 21.

FIG. 23 is a top view of the aerosol-generating device illustrated in FIG. 21.

FIG. 24 is a top left, rear perspective view of the aerosol-generating device illustrated in FIG. 21, where the lid is opened.

DETAILED DESCRIPTION OF EXAMPLE EMBODIMENTS

Figure 1:
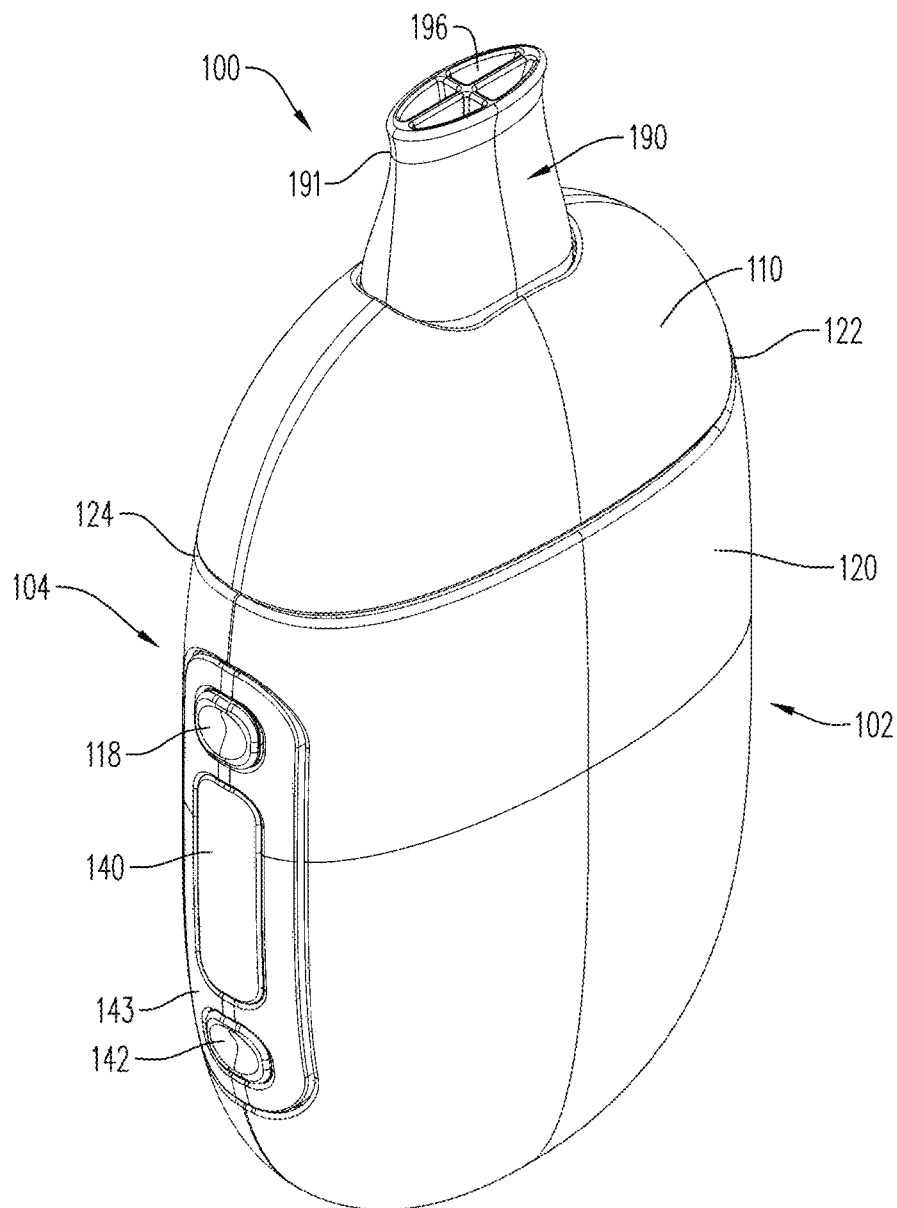
FIG. 1 is a top right, front perspective view of an aerosol-generating device in accordance with at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, component, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," specify the presence of stated features, integers, steps, operations, and/or elements, but do not preclude the presence or addition of one or more other features, integers, steps, operations, elements, and/or groups thereof.

When the terms "about" or "substantially" are used in this specification in connection with a numerical value, it is intended that the associated numerical value includes a manufacturing or operational tolerance (e.g., +10%) around the stated numerical value. Moreover, when the terms "generally" or "substantially" are used in connection with geometric shapes, it is intended that precision of the geometric shape is not required but that latitude for the shape is within the scope of the disclosure. Furthermore, regardless of whether numerical values or shapes are modified as "about," "generally," or "substantially," it will be understood that these values and shapes should be construed as including a manufacturing or operational tolerance (e.g., ±10%) around the stated numerical values or shapes.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, "coupled" includes both removably coupled and permanently coupled. For example, when an elastic layer and a support layer are removably coupled to one another, the elastic layer and the support layer can be separated upon the application of sufficient force.

Figure 2:
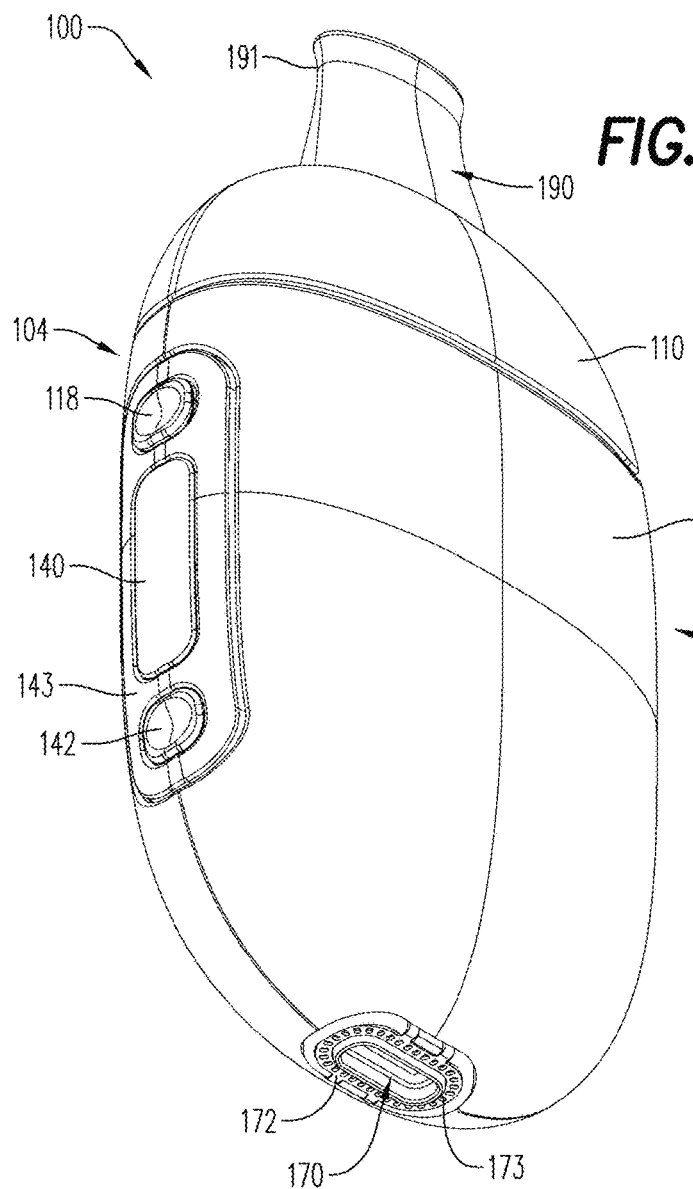
FIG. 2 is a bottom right, front perspective view of the aerosol-generating device illustrated in FIG. 1.
Figure 3:
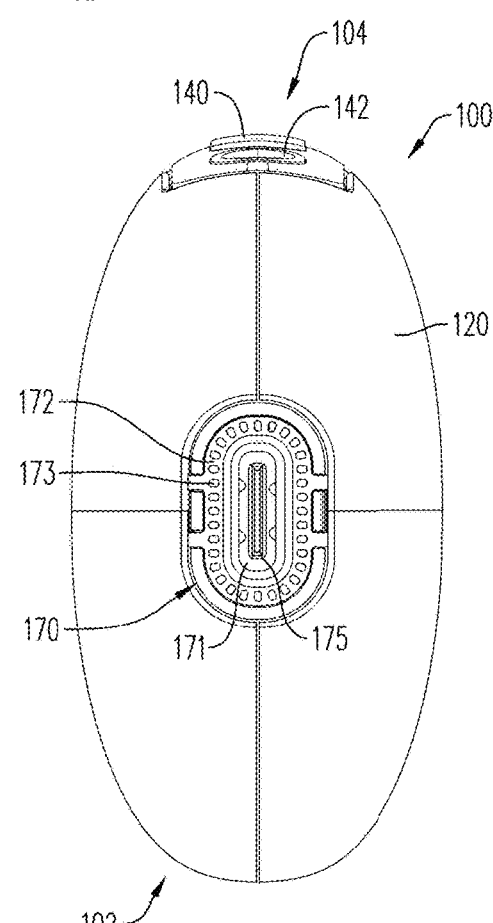
FIG. 3 is a bottom view of the aerosol-generating device illustrated in FIG. 1.
Figure 4:
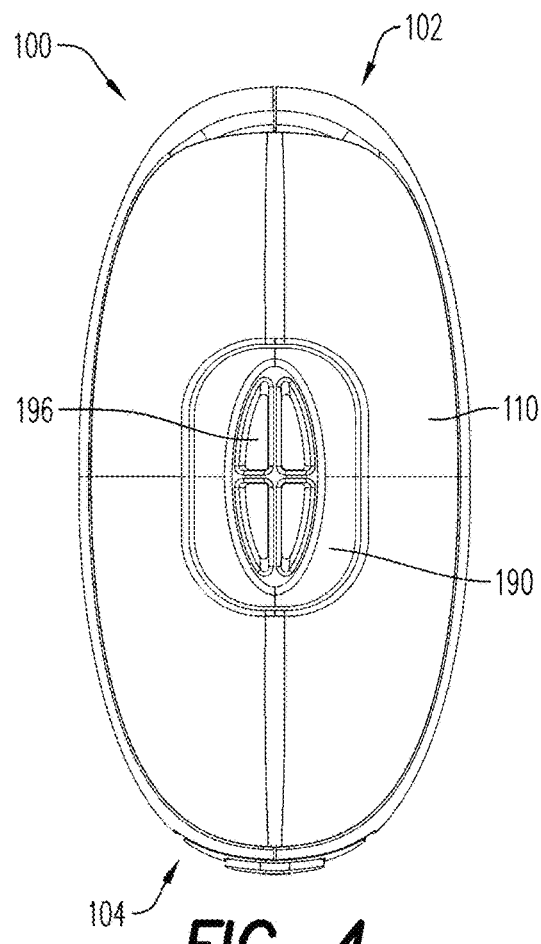
FIG. 4 is a top view of the aerosol-generating device illustrated in FIG. 1.
Figure 5:
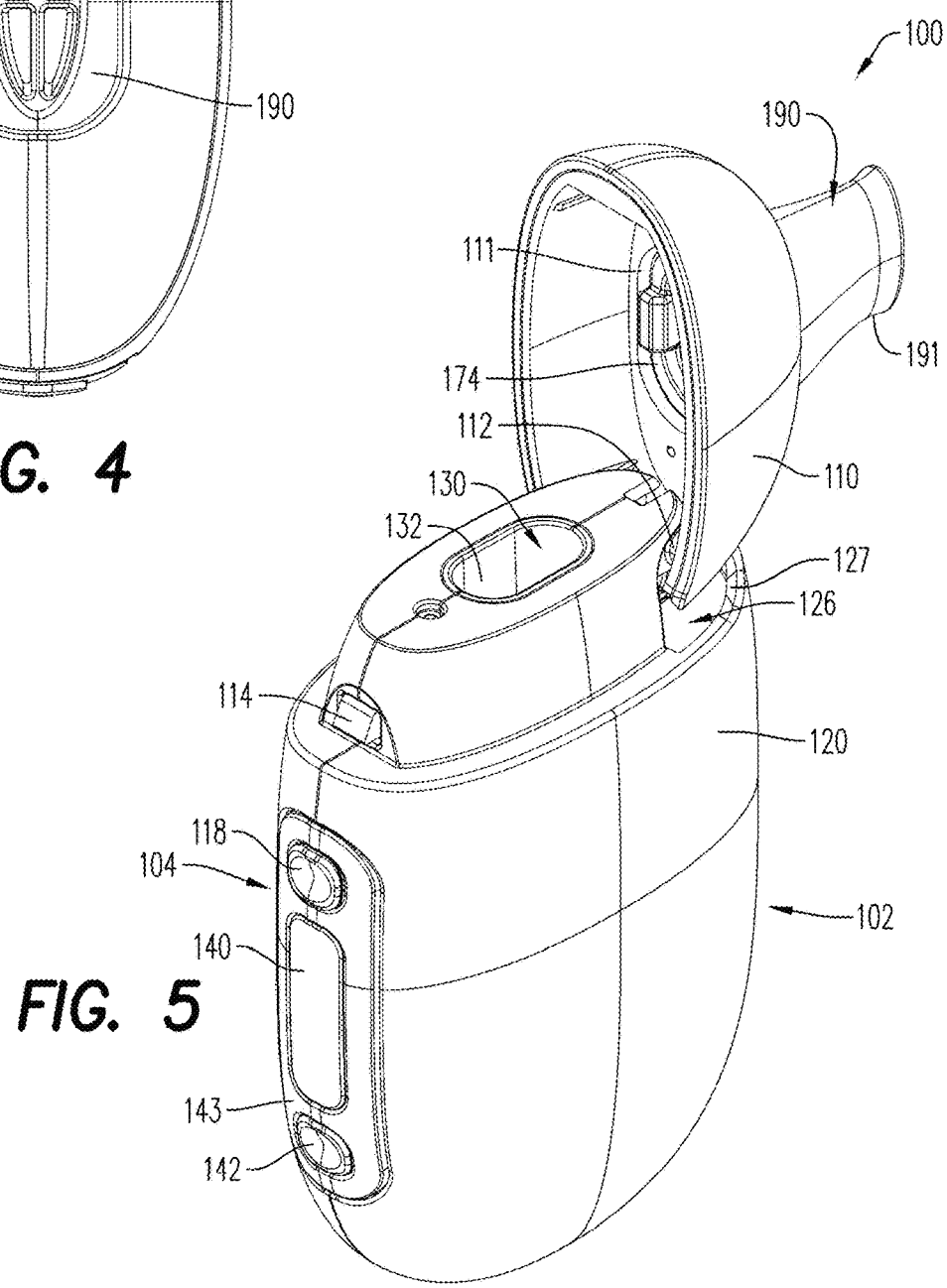
FIG. 5 is a top right, front perspective view of the aerosol-generating device illustrated in FIG. 1, where the lid is opened.
Figure 6:
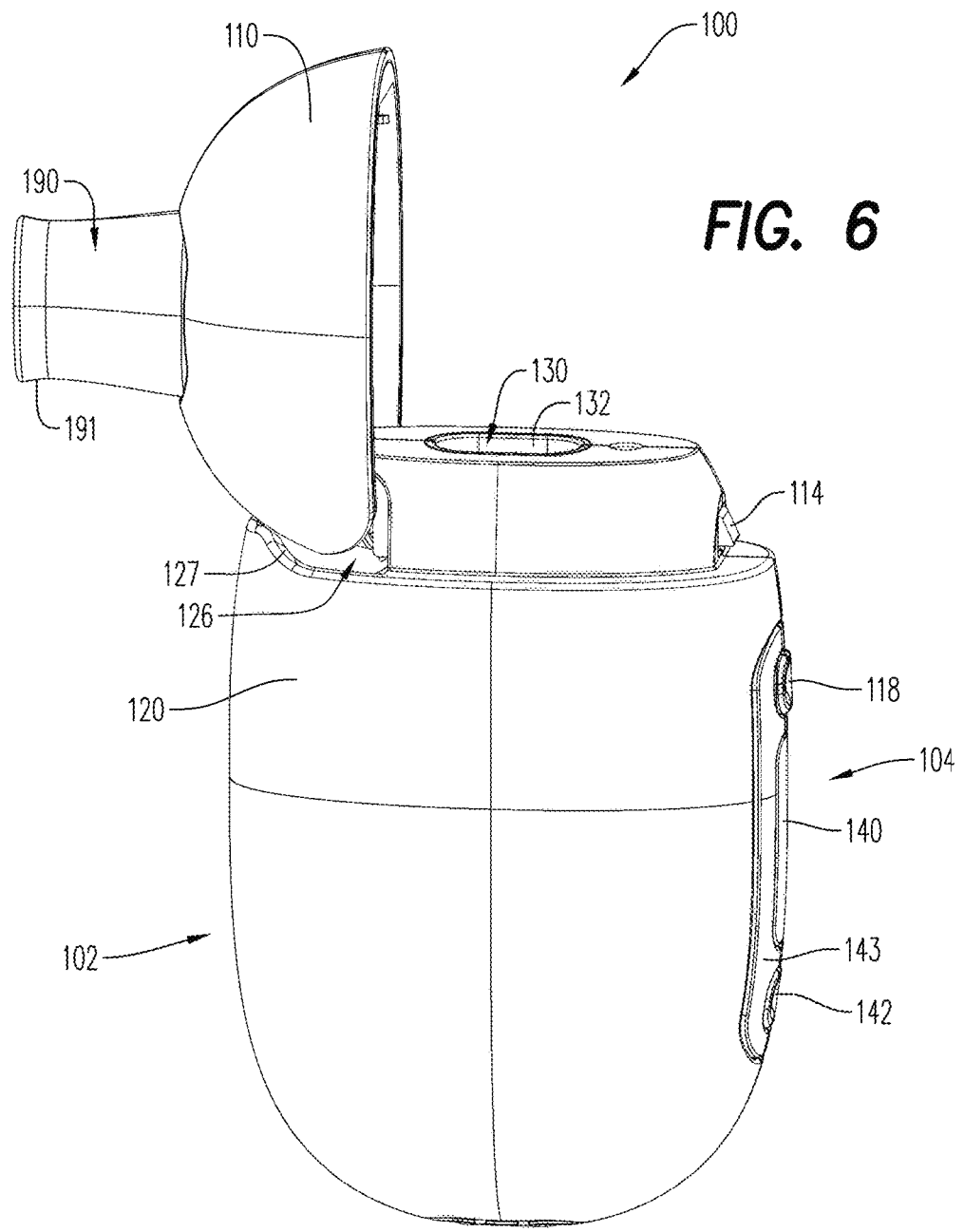
FIG. 6 is a rear perspective view of the aerosol-generating device illustrated in FIG. 5.
Figure 7:
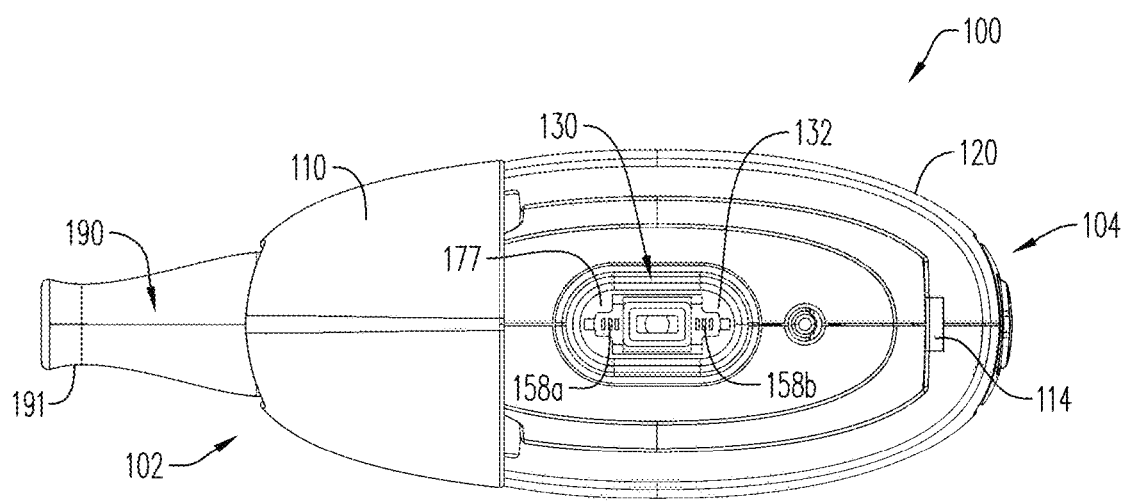
FIG. 7 is a top-down view of the aerosol-generating device illustrated in FIG. 5.
Figure 8:
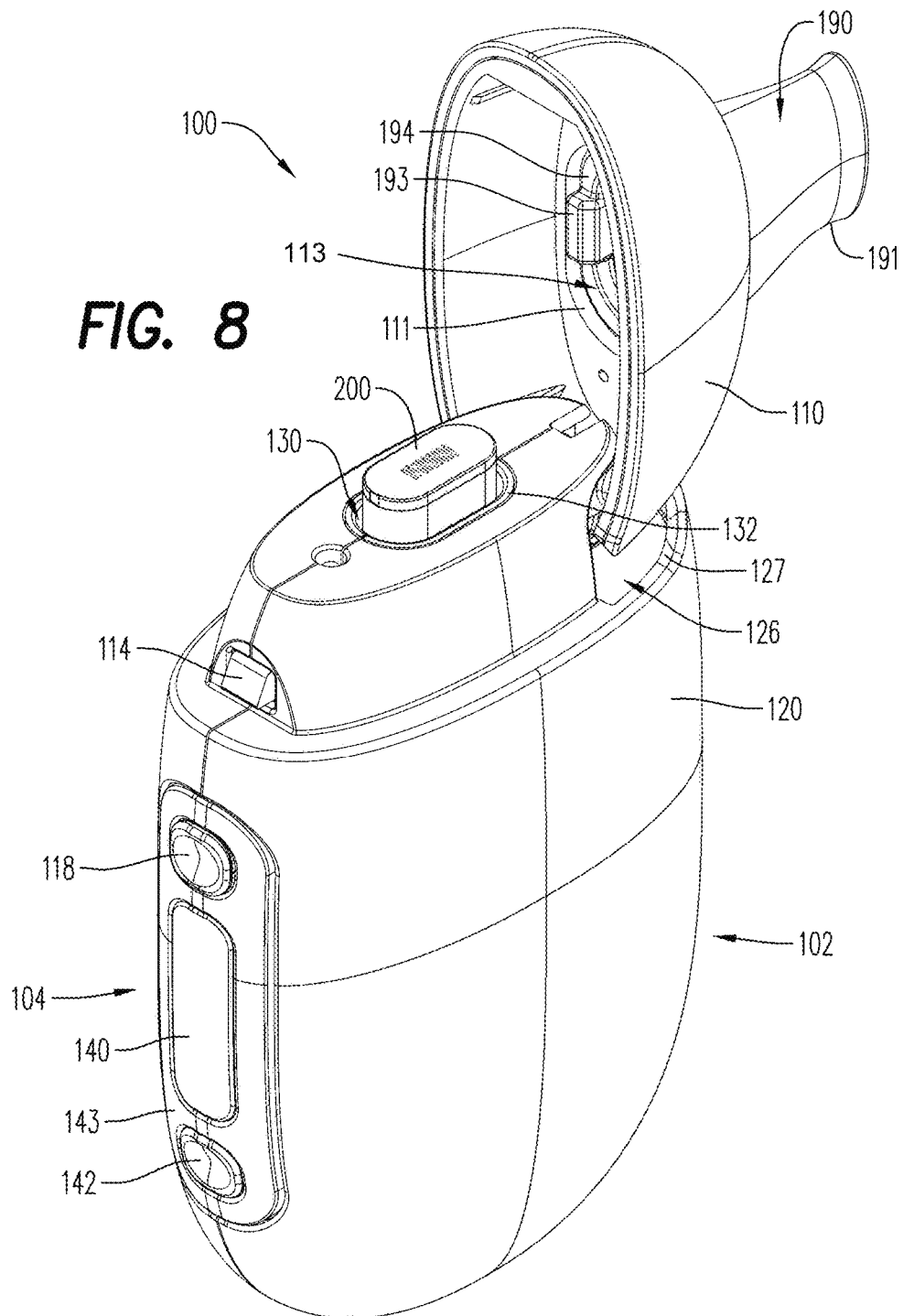
FIG. 8 is a top right, front perspective view of the aerosol-generating device illustrated in FIG. 5, including a capsule.
Figure 9:
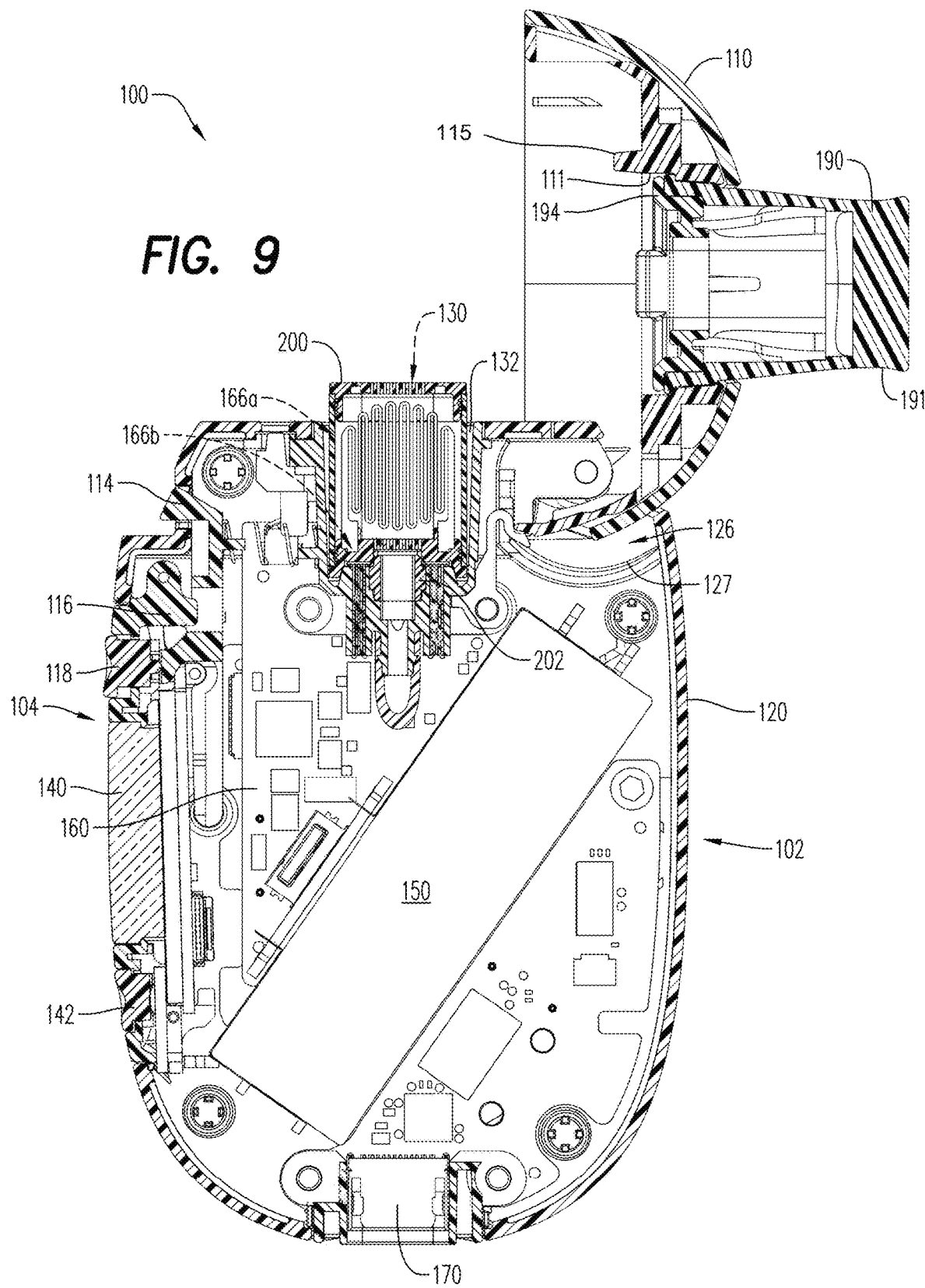
FIG. 9 is a cross-sectional view of the aerosol-generating device illustrated in FIG. 8.
Figure 10:
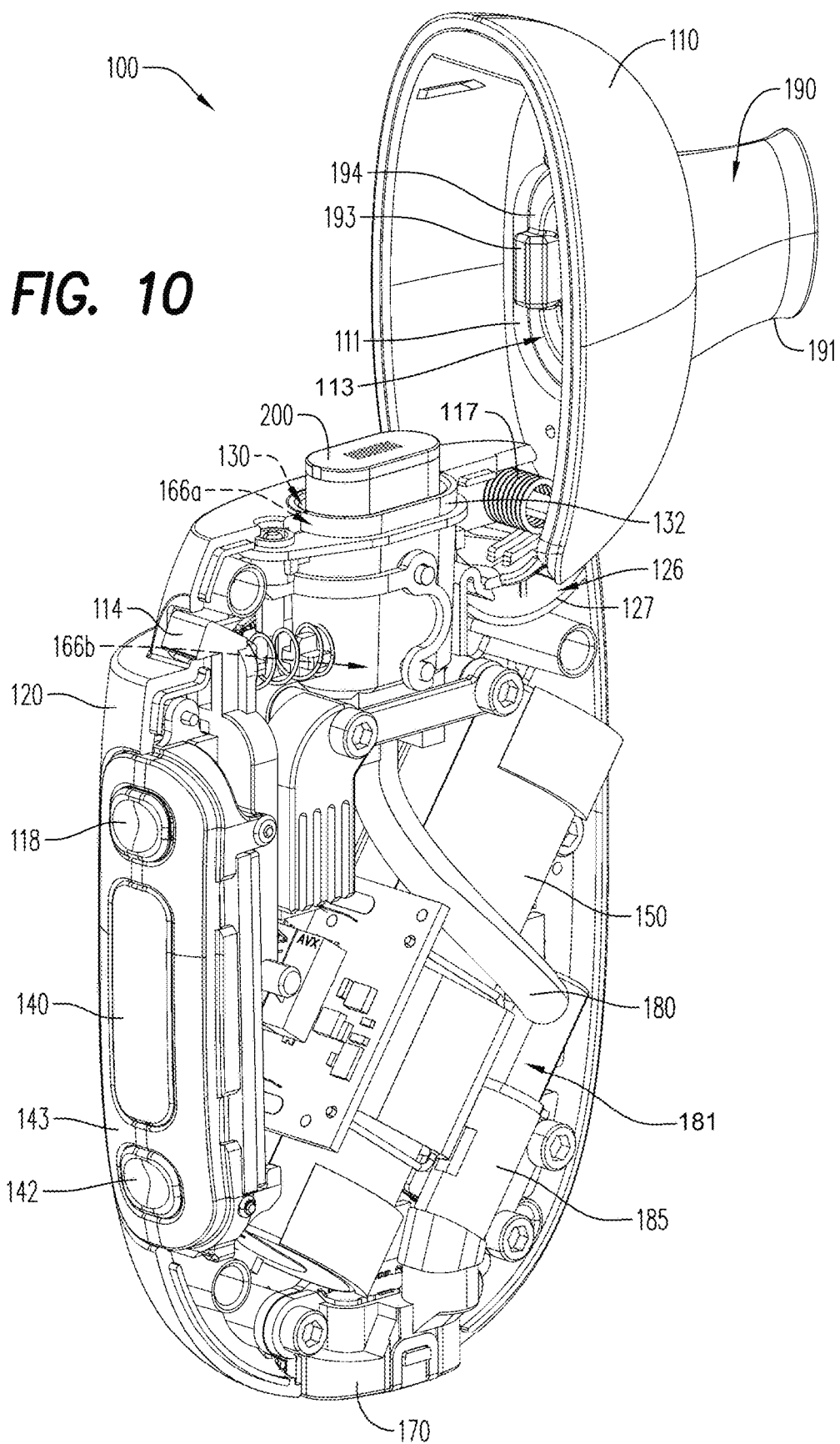
FIG. 10 is a partial front perspective view of the aerosol-generating device illustrated in FIG. 8, where a section of the housing has been removed.

FIGS. 1-10 are illustrations of an aerosol-generating device 100 (e.g., heat-not-burn (HNB) aerosol-generating device) in accordance with at least one example embodiment. For example, FIG. 1 is a top perspective view of the aerosol-generating device 100, where the lid 110 is closed. FIG. 2 is a bottom perspective view of the aerosol-generating device 100, where the lid 110 is closed. FIG. 3 is a bottom-up view of the aerosol-generating device 100, where the lid 110 is closed. FIG. 4 is a top-down view of the aerosol-generating device 100, where the lid 110 is closed. FIG. 5 is another top perspective view of the aerosol-generating device 100, where the lid 110 is opened. FIG. 6 is another top perspective view of the aerosol-generating device 100, where the lid 110 is opened. FIG. 7 is a top-down view of the aerosol-generating device 100, where the lid 110 is opened. FIG. 8 is another top perspective view of the aerosol-generating device 100, where the lid 110 is opened and a capsule 200 is received by the capsule receiving cavity 130. FIG. 9 is a cross-sectional view of the aerosol-generating device 100, where the lid 110 is opened and a capsule 200 is received by the capsule receiving cavity 130. FIG. 10 is a partial, perspective view of the aerosol-generating device 100, where a section of the housing 120 has been removed to show various internal components, the lid 110 is opened, and a capsule 200 is received by the capsule receiving cavity 130.

As illustrated, in at least some example embodiments, the aerosol-generating device 100 has a general oblong or pebble shape and a replaceable mouthpiece 190 that extends from the main body of the aerosol-generating device 100. For example, the aerosol-generating device 100 may include a housing 120 that defines a capsule-receiving cavity 130 (as best shown in FIG. 5-8). Additionally, a lid 110 is configured to open/close relative to the housing 120 and is coupleable to the replaceable mouthpiece 190. For example, the lid 110 may be fixedly coupled to the housing 120 at a first point 122 and releasably coupleable to the housing 120 at a second point 124. The first point 122 of the housing 120 may be on a first side 102 of the device 100. The second point 124 of the housing 120 may be on a second side 104 of the aerosol-generating device 100. In some instances, the lid 110 may also be referred to as a door. An exterior of the housing 120 and/or lid 110 may be formed from a metal (such as aluminum, stainless steel, and the like); an aesthetic, food contact rated plastic (such as, a polycarbonate (PC), acrylonitrile butadiene styrene (ABS) material, liquid crystalline polymer (LCP), a copolyester plastic, or any other suitable polymer and/or plastic); or any combination thereof. The replaceable mouthpiece 190 may be similarly formed from a metal (such as aluminum, stainless steel, and the like); an aesthetic, food contact rated plastic (such as, a polycarbon-ate (PC), acrylonitrile butadiene styrene (ABS) material, liquid crystalline polymer (LCP), a copolyester plastic, or any other suitable polymer and/or plastic); and/or plant-based materials (such as wood, bamboo, and the like). One or more interior surfaces or the housing 120 and/or lid 110 may be formed from or coated with a high temperature plastic (such as, polyetheretherketone (PEEK), liquid crystal polymer (LCP), or the like). The lid 110 and the housing 120 may be collectively regarded as the main body of the aerosol-generating device 100.

The lid 110 may be fixedly coupled to the housing 120 at the first point 122 by a hinge 112, or other similar connector, that allows the lid 110 to move (e.g., swing and rotate) from an open position (such as illustrated in FIGS. 5-10) to a closed position (such as illustrated in FIG. 1-2). As illustrated in FIG. 10, the hinge 112 may include a torsion spring 117. In at least some example embodiments, such as illustrated in FIGS. 5-6 and 8-10, the housing 120 includes a recess 126 at the first point 122. The recess 126 may be configured to receive a portion of the lid 110 so as to allow for an easy and smooth movement of the lid 110 from the open position to the closed position (and vice versa). The recess 126 may have a structure that corresponds with a relative portion of the lid 110. For example, as illustrated, the recess 126 may include a substantially curved portion 127 that has a general concave shape that corresponds with the curvature of the lid 110, which has a general convex shape.

The lid 110 may be releasably coupleable to the housing 120 at the second point 124 by a latch 114, or other similar connector, that allows the lid 110 to be fixed or secured in the closed position and easily releasable so as to allow the lid 110 to move from the secured closed position to the open position. In at least one example embodiment, the latch 114 may be coupled to a latch release mechanism 116. The latch release mechanism 116 may be configured to move the latch 114 from a first or closed position to a second or open position. For example, such as best illustrated in FIG. 10, the latch 114 may extend downwards in the housing 120 and the latch release mechanism 116 may be perpendicular to the downwards length of the latch 114. As such, the latch release mechanism 116 is configured to apply pressure to the latch 114. For example, the latch release mechanism 116 may be movable between a first position and a second position. In the first position, the latch release mechanism 116 may be neutral relative to the latch 114. In the second position, the latch release mechanism 116 may apply pressure to the downwards length of the latch 114 so as to move the latch 114 from the secured or latched close position to the open position.

In at least one example embodiment, such as best illustrated in FIG. 10, the latch release mechanism 116 is in communication with a latch release button 118 that is configured to activate the latch release mechanism 116—i.e., to move the latch 114 from the first or closed or secured position to the second or pressure-applying position and to move/return the latch 114 from the open position to the secured or closed position. In at least one example embodiment, the latch release button 118 is an adult consumer interaction button disposed on the second side 104 of the aerosol-generating device 100. For example, when the latch release button 118 is pressed by the adult consumer, the latch release mechanism 116 may move from the first or closed or secured position to the second or pressure-applying position so as to move the latch 114 from the secured or closed position to the open position. The latch release button 118 may have a substantially circular shape with a center depression or dimple configured to direct the pressure applied by the adult consumer, although example embodiments are not limited thereto. One or more sensors (not shown) configured to detect the lid 110 opening and closure may be embedded or otherwise disposed within the housing 120 and/or one or more of the elements therein (e.g., latch 114, latch release mechanism 116, latch release button 118).

In at least some example embodiments, such as best illustrated in FIGS. 9 and 10, the housing 120 encases or houses the latch release mechanism 116, as well as a power source 150 and a processing or control circuitry 160. The control circuitry 160 may be hardware including logic circuits; a hardware/software combination such as a processor executing software; or a combination thereof. For example, the control circuitry 160 may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The supply of current from the power source 150 may be in response to a manual operation (e.g., button-activation) or an automatic operation (e.g., puff-activation). The power source 150 may include one or more batteries (e.g., rechargeable dual battery arrangement, lithium-ion battery, and/or fuel cells). In at least some example embodiments, the control circuitry 160 may further include a haptic motor that may be disposed on a side of the power source 150.

In at least some example embodiments, such as best illustrated in FIGS. 1-2, 5, and 8-10, the housing 120 includes a consumer interface panel 143 disposed on the second side 104 of the device 100. For example, the consumer interface panel 143 may be an oval-shaped panel that runs along the second side of the device 100. The consumer interface panel 143 may include the latch release button 118, such as discussed above, as well as a communication screen 140 and/or a power button 142. For example, in at least some example embodiments, the consumer interface panel 143 may include the communication screen 140 disposed between the latch release button 118 and the power button 142. As illustrated, the latch release button 118 may be disposed towards a top of the aerosol-generating device 100, and the power button 142 may be disposed towards a bottom of the aerosol-generating device 100. Like the latch release button 118, the power button 142 may also be an adult consumer interaction button. The power button 142 may have a substantially circular shape with a center depression or dimple configured to direct the pressure applied by the adult consumer, although example embodiments are not limited thereto. The power button 142 may turn on and off the aerosol-generating device 100. Though only the two buttons are illustrated, it should be understood more or less buttons may be provided depending on the available features and desired adult consumer interface.

In at least one example embodiment, the communication screen 140 is an integrated thin-film transistor ("TFT") screen. In other example embodiments, the communication screen 140 is an organic light emitting diode ("OLED") or light emitting diode ("LED") screen. The communication screen 140 is configured for adult consumer engagement and may have a generally oblong shape.

In at least some example embodiments, the housing 120 defines a charging connector or port 170. For example, as best illustrated in FIG. 2, the charging connector 170 may be defined/disposed in a bottom end of the housing 120 distal from the capsule-receiving cavity 130. The charging connector 170 may be configured to receive an electric current (e.g., via a USB/mini-USB cable) from an external power source so as to charge the power source 150 internal to the aerosol-generating device 100. For example, in at least one example embodiment, such as best illustrated in FIG. 3, the charging connector 170 may be an assembly defining a cavity 171 that has a projection 175 within the cavity 171. In an example embodiment, the projection 175 does not extend beyond the rim of the cavity 171. In addition, the charging connector 170 may also be configured to send data to and/or receive data (e.g., via a USB/mini-USB cable) from another aerosol-generating device (e.g., heat-not-burn (HNB) aerosol-generating device) and/or other electronic device (e.g., phone, tablet, computer, and the like). In at least one embodiment, the aerosol-generating device 100 may instead or additionally be configured for wireless communication (e.g., via Bluetooth) with such other aerosol-generating devices and/or electronic devices.

In at least some example embodiments, such as best illustrated in FIG. 3, a protective grille 172 is disposed around the charging connector 170. The protective grille 172 may be configured to help reduce or prevent debris ingress and/or the inadvertent blockage of the incoming airflow. For example, the protective grille 172 may define a plurality of pores 173 along its length or course. As illustrated, the protective grille 172 may have an annular form that surrounds the charging connector 170. In this regard, the pores 173 may also be arranged (e.g., in a serial arrangement) around the charging connector 170. Each of the pores 173 may have an oval or circular shape, although not limited thereto. In at least one example embodiment, the protective grille 172 may include an approved food contact material. For example, the protective grille 172 may include plastic, metal (e.g., stainless steel, aluminum), or a combination thereof. In at least some example embodiments, a surface of the protective grille 172 may be coated, for example with a thin layer of plastic, and/or anodized.

The pores 173 in the protective grille 172 may function as inlets for air drawn into the aerosol-generating device 100. During the operation of the aerosol-generating device 100, ambient air entering through the pores 173 in the protective grille 172 around the charging connector 170 will converge to form a combined flow that then travels to the capsule 200. For example, the pores 173 may be in fluidic communication with the capsule-receiving cavity 130. In at least some example embodiments, air may be drawn from the pores 173 and through the capsule-receiving cavity 130. For example, air may be drawn through a capsule 200 received by the capsule-receiving cavity 130 and out of the replaceable mouthpiece 190.

The capsule 200 (for example, as illustrated in FIG. 8) may have various forms and configurations. For instance, the capsule 200 may have any of the forms and configurations as subsequently discussed in connection with FIGS. 32-46. Specifically, in an example embodiment, the capsule 200 may be the same as described in connection with the capsule 1300 in FIGS. 37-41. Referring to FIGS. 37-41, the capsule 1300 has a housing configured to contain an aerosol-forming substrate (e.g., aerosol-forming substrate 1860' in FIG. 48) and a heater, wherein the downstream portion of the housing may be in the form of a first end cap 1310 (e.g., downstream cap). The upstream portion of the housing may be in the form of a second end cap 1320 (e.g., upstream cap, connector cap). The body portion of the housing may be in the form of a cover 1330 (e.g., shell, box sleeve).

Figure 37:
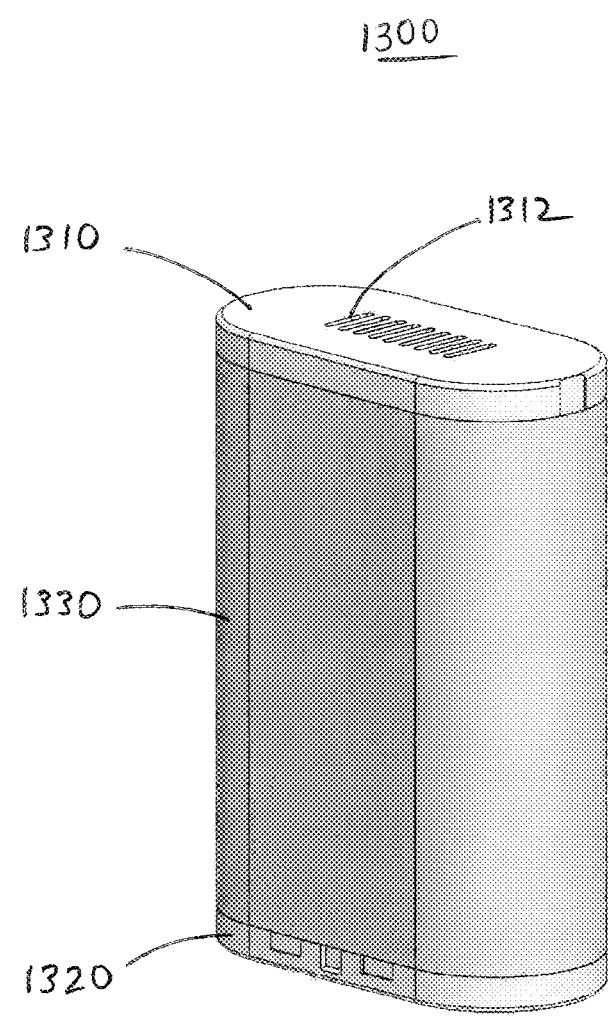
FIG. 37 is a downstream perspective view of another capsule for an aerosol-generating device according to an example embodiment.
Figure 38:
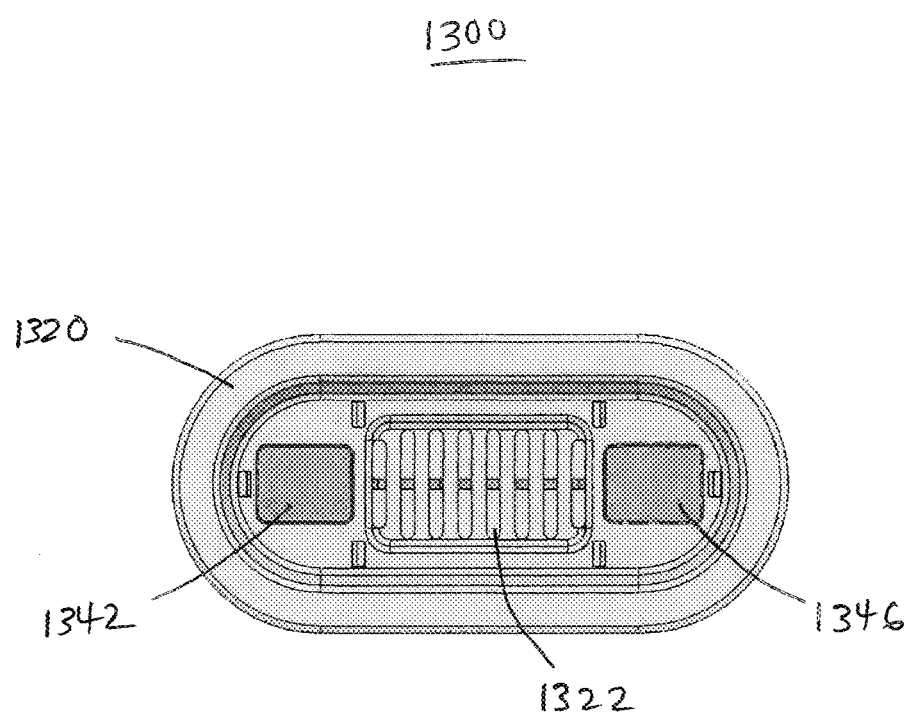
FIG. 38 is an upstream end view of the capsule of FIG. 37.

As illustrated in FIGS. 37-38, the first end cap 1310 defines a first opening 1312, while the second end cap 1320 defines a second opening 1322. In an example embodiment, the first opening 1312 is in the form of a series of outlet openings (e.g., nine outlet openings), and the second opening 1322 is in the form of a series of inlet openings (e.g., eight inlet openings). Additionally, the second end cap 1320 may expose a first end section 1342 and a second end section 1346 of a heater 1340 (e.g., FIG. 41). As illustrated, the second opening 1322 may be between the exposed portions of the first end section 1342 and the second end section 1346. The first end cap 1310 and/or the second end cap 1320 may be transparent so as to serve as windows configured to permit a viewing of the contents/components (e.g., aerosol-forming substrate and/or heater) within the capsule 1300.

Figure 39:
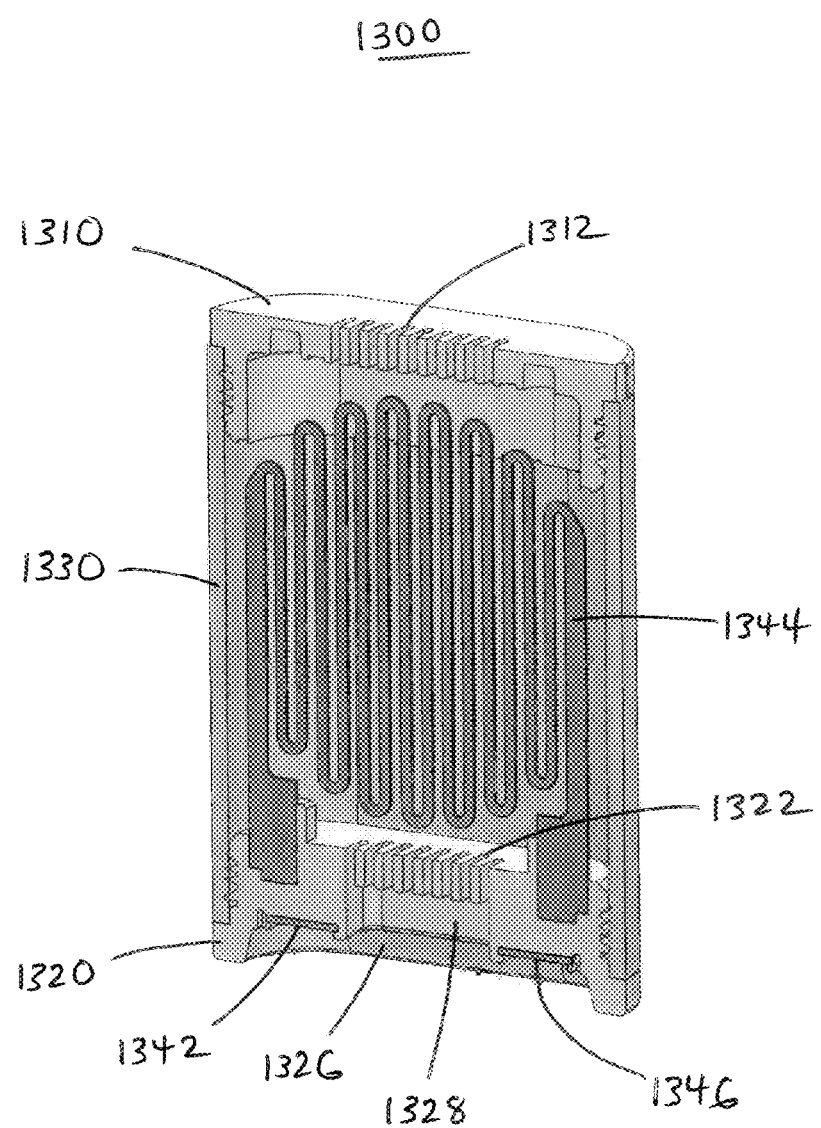
FIG. 39 is a cross-sectional view of the capsule of FIG. 37.

Referring to FIG. 39, the intermediate section 1344 of the heater 1340 is an internal segment configured to heat an aerosol-forming substrate within the capsule 1300. The first end section 1342 and the second end section 1346 of the heater 1340 are external segments configured to establish an electrical connection with a power source (e.g., electrical connection with the power source 150 via the electrical contacts 152a and 152b).

In addition to the second opening 1322, the second end cap 1320 also defines an alignment recess 1326 and an inlet recess 1328. The alignment recess 1326 and the inlet recess 1328 may be viewed as being in a multi-level arrangement, wherein the base/inner end surface of the alignment recess 1326 (which exposes the first end section 1342 and the second end section 1346) may be regarded as being on one level, while the base/inner end surface of the inlet recess 1328 (or the grille-like surface of the second opening 1322) may be regarded as being on another level. The alignment recess 1326 is configured to facilitate a positioning of the capsule 1300 during its insertion into the device body of an aerosol-generating device. In an example embodiment, the alignment recess 1326 has angled sidewalls which taper inward toward the inlet recess 1328. With the angled sidewalls, the alignment recess 1326 may be quickly coupled with a corresponding engagement member of the device body with greater ease. For instance, when received within the capsule-receiving cavity 130 of the aerosol-generating device 100, the alignment recess 1326 of the capsule 1300 may be engaged with the angled surfaces 176 of the capsule connector 132, while the inlet recess 1328 of the capsule 1300 may be engaged with the capsule seal 202 (e.g., FIG. 12). As a result, the capsule 1300 may be properly loaded and aligned within the device body of the aerosol-generating device in a relatively consistent manner.

Figure 40:
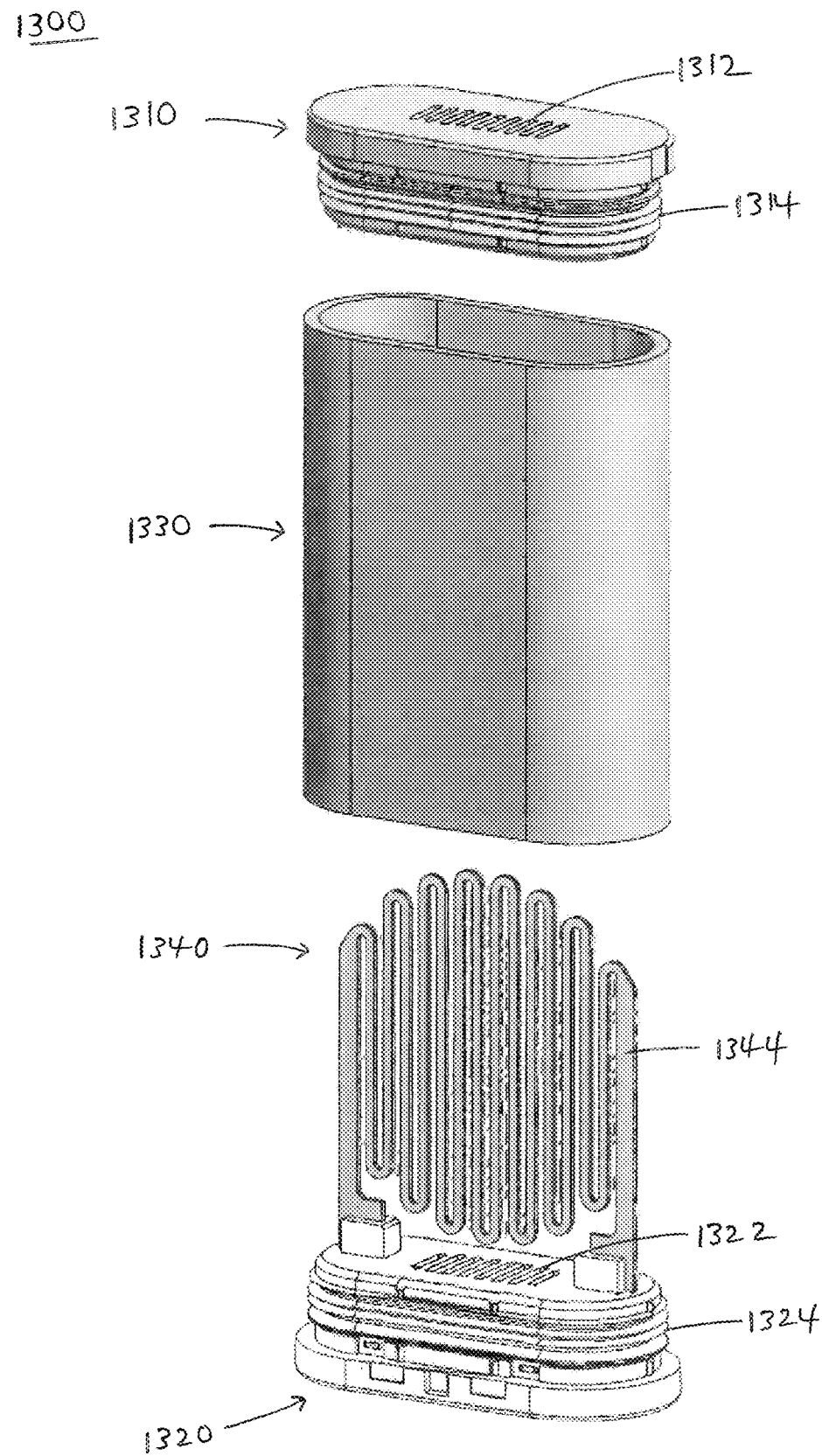
FIG. 40 is an exploded view of the capsule of FIG. 37.

Referring to FIG. 40, the first end cap 1310 includes a first sealing ridge 1314, while the second end cap 1320 includes a second sealing ridge 1324. In an example embodiment, the first sealing ridge 1314 is in the form of a series of ribs (e.g., four ribs), and the second sealing ridge 1324 is in the form of a series of ribs (e.g., four ribs). In some instances, the ribs in each of the series may be of different heights to ensure a desired contact with the cover 1330. When the capsule 1300 is assembled, the first sealing ridge 1314 of the first end cap 1310 and the second sealing ridge 1324 of the second end cap 1320 are configured to interface with the inner surface of the cover 1330 (e.g., via an interference fit) to provide an air seal. As a result, when air is directed to the capsule 1300 during an operation of the aerosol-generating device, the air will enter the capsule 1300 via the inlet recess 1328 and the second opening 1322 in the second end cap 1320 (as opposed to entering the capsule 1300 via a gap between the second end cap 1320 and the cover 1330, wherein such air may essentially just flow along the inner surface of the cover 1330 so as to primarily bypass the aerosol-forming substrate and/or the intermediate section 1344 of the heater 1340). Similarly, with an appropriate seal, the aerosol generated within the chamber of the capsule 1300 will be drawn out through the first opening 1312 in the first end cap 1310 (as opposed to leaking out through a gap between the first end cap 1310 and the cover 1330).

Figure 41:
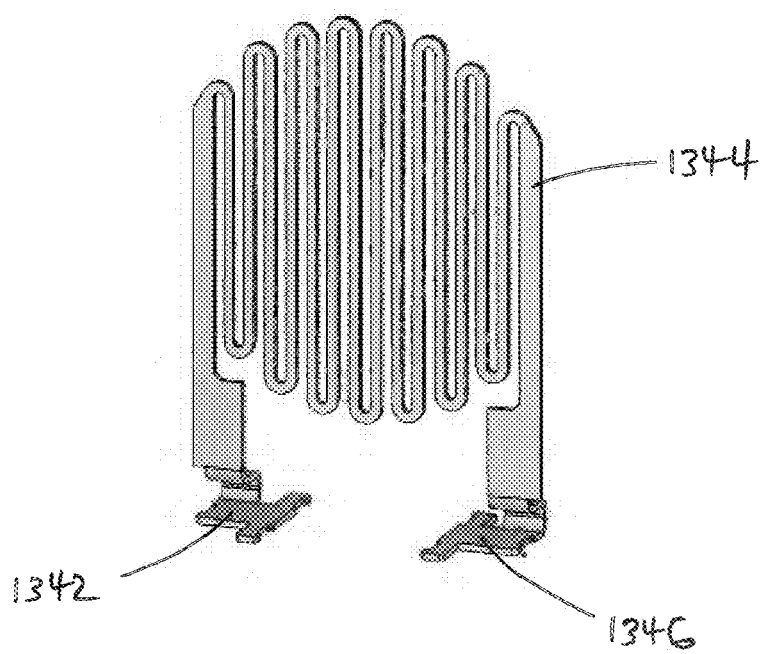
FIG. 41 is an isolated view of the heater in FIG. 40.

Referring to FIG. 41, the heater 1340 includes a first end section 1342, an intermediate section 1344, and a second end section 1346. The intermediate section 1344 of the heater 1340 may have a planar and winding form resembling a compressed oscillation or zigzag with a plurality of parallel segments (e.g., eight to sixteen parallel segments). However, it should be understood that other forms for the intermediate section 1344 of the heater 1340 are also possible (e.g., spiral form, flower-like form). The terminus of each of the first end section 1342 and the second end section 1346 may be oriented orthogonally to the plane of the intermediate section 1344. Each of the first end section 1342 and the second end section 1346 may also include segments having a sideways J-shape. As a result, the first end section 1342 and the second end section 1346 may be embedded relatively securely within the second end cap 1320 while providing a pair of electrical contact surfaces.

The above discussion should be understood to be a non-limiting introduction to the capsule 200, which, as noted supra, may be the same as the capsule 1300. As a result, the insertion and mechanical/electrical engagement of the capsule 200 within the aerosol-generating device 100 may be discussed with reference to the specific details of the capsule 1300. Further details and alternatives regarding the capsule 1300 are also subsequently discussed herein.

In at least one example embodiment, such as best illustrated in FIG. 10, the housing 120 encases or houses an air hose 180. The air hose 180 may extend between and/or physically connect the capsule-receiving cavity 130 (via an air inlet connection 184) and the one or more air inlets or pores 173. An air channel assembly 181 may also be provided as an intermediary between the air hose 180 and the pores 173. In such an instance, the air channel assembly 181 may be configured to direct the incoming airflow (that is drawn in through the pores 173) to the air hose 180. In at least one example embodiment, the air channel assembly 181 includes an airflow restrictor configured to provide optional control over the airflow through the device 100. In at least one example embodiment, one or more flow sensors 185 may be disposed within or along the air channel assembly 181 and/or along the air hose 180. In at least one example embodiment, the one or more flow sensors 185 includes a microelectromechanical system (MEMS) flow or pressure sensor or another type of sensor configured to measure air flow, such as a hot-wire anemometer. In at least one example embodiment, the one or more flow sensors 185 may include pressure sensors, such as a capacitive pressure sensor, that are configured to measure a negative pressure during a draw event. In at least one example embodiment, the air channel assembly 181 may omit the one or more sensors 185.

In at least some example embodiments, the housing 120 encloses a capsule connector 132. Additionally, in some instances, the capsule connector 132 may be mounted or otherwise secured to a printed circuit board (PCB) within the housing 120. In at least one example embodiment, the capsule connector 132 defines the capsule-receiving cavity 130. FIGS. 11-15 are illustrations of a capsule connector 132 in accordance with at least one example embodiment.

Figure 13:
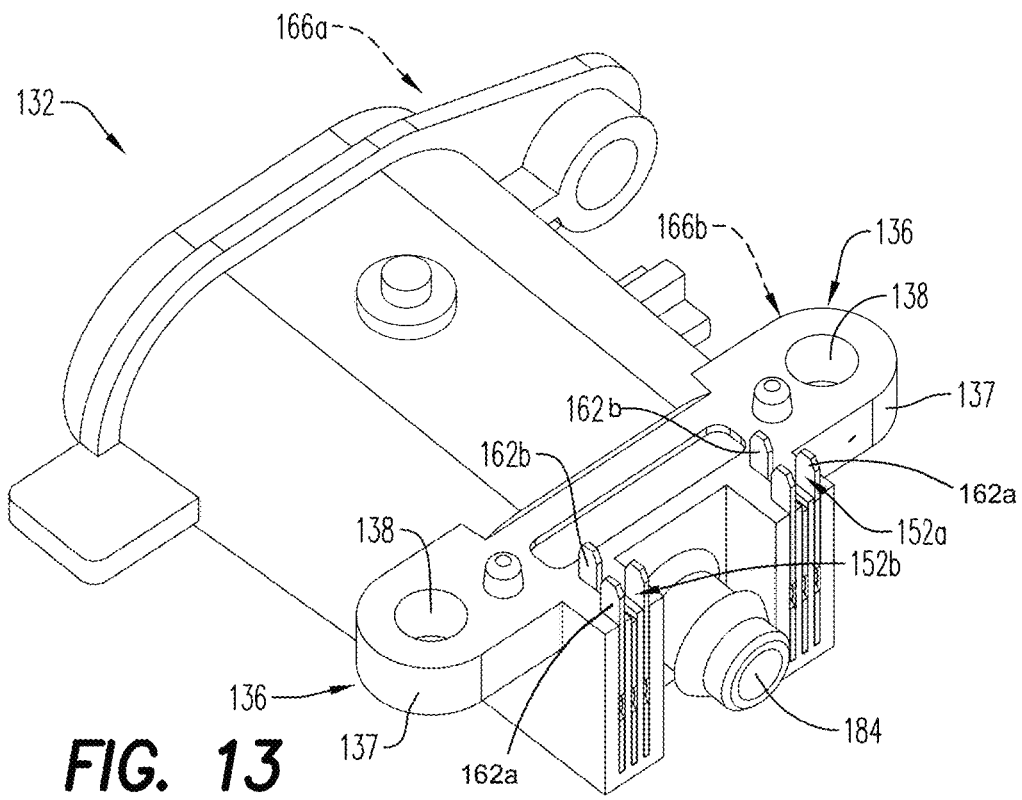
FIG. 13 is a bottom, rear perspective view of the capsule connector illustrated in FIG. 11.

In at least some example embodiments, the capsule connector 132 includes a body or housing 134 that defines the capsule-receiving cavity 130. In at least some example embodiments, such as best illustrated in FIG. 13, the body 134 includes an air inlet connection 184. The air inlet connection 184 may be configured to be coupled to an end of the air hose 180. In at least some example embodiments, the body 134 includes one or more couplers or mounting brackets 135, 136 configured to couple the capsule connector 132 to the housing 120 and/or to a component within the housing 120. A first coupler or mounting bracket 136 may include, for example, one or more wings or tab portions 137 and coupler-receiving openings 138 (e.g., mounting bosses). The coupler-receiving openings 138 may be configured to receive one or more corresponding couplers of the housing 120 (such as, coupler 128 (e.g., screw) as illustrated best in FIG. 15). A second coupler or mounting bracket 135 may include, for example, one or more wings or tab portions 141 and coupler-receiving openings 139. The coupler-receiving openings 139 may be configured to receive one or more corresponding couplers of the lid 110. For example, the coupler-receiving openings 139 may be configured to receive a post 115 defined on an interior surface of the lid 110. Specifically, a switch (e.g., push button switch) may be positioned within the coupler-receiving opening 139 so as to be pressed by the post 115 when the lid 110 is closed and released when the lid 110 is open. As a result, a lid open/closed detection method may be provided.

In at least some example embodiments, the capsule connector 132 includes one or more electrical connectors or contacts 152A, 152B. For example, as illustrated, the capsule connector 132 may include a first electrical contact 152A and a second electrical contact 152B. As illustrated, the first electrical contact 152A may be in the form of three contact members. Similarly, the second electrical contact 152B may also be in the form of three contact members. The electrical contacts 152A, 152B are configured to apply current or other electrical signals to the capsule 200 received by the capsule-receiving cavity 130. In at least one example embodiment, the electrical contacts 152A, 152B may be in electrical communication with the power source 150 and/or control circuitry 160 disposed within the housing 120. The electrical contacts 152A, 152B may be formed of copper or of a copper alloy (e.g., copper-titanium) with the option of also having a gold plating.

Figure 14:
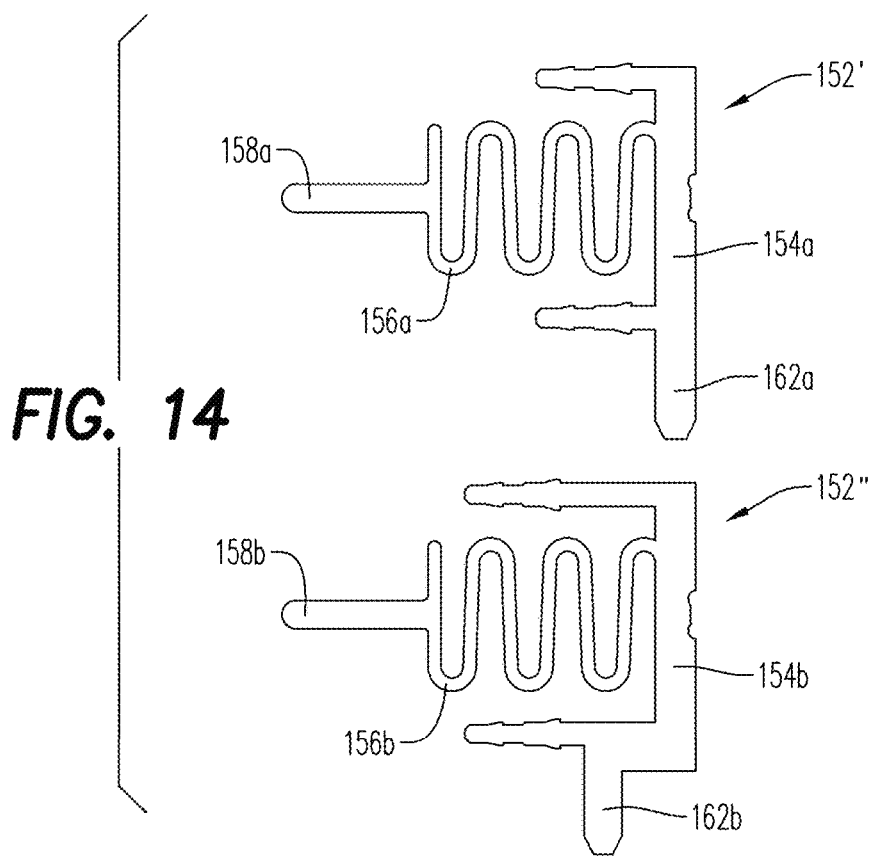
FIG. 14 is a top view of the electrical contacts in accordance with at least one example embodiment.

In at least some example embodiments, as best illustrated in FIG. 14, each of the contact members of the electrical contacts 152A, 152B may be one of two types: contact member 152' or contact member 152". For instance, the electrical contact 152A may include a combination of both the contact member 152' and the contact member 152". As illustrated, the electrical contact 152A may include a contact member 152" between a pair of contact members 152'. In another instance, the electrical contact 152A may include a contact member 152' between a pair of contact members 152". Alternatively, instead of two types of contact members, the electrical contact 152A may include a plurality of one of the contact member 152' or the contact member 152" (e.g., identical contact members).

Similarly, the electrical contact 152B may include a combination of both the contact member 152' and the contact member 152". As illustrated, the electrical contact 152B may include a contact member 152" between a pair of contact members 152'. In another instance, the electrical contact 152B may include a contact member 152' between a pair of contact members 152". Alternatively, instead of two types of contact members, the electrical contact 152B may include a plurality of one of the contact member 152' or the contact member 152" (e.g., identical contact members).

Each of the contact members 152', 152" includes a base 154A, 154B, respectively. In at least one example embodiment, each of the contact members 152', 152" has a terminal or soldering point 162A, 162B, respectively. As illustrated, the soldering point 162A of the contact member 152' may be aligned (e.g., coaxial) with the base 154A. In contrast, the soldering point 162B of the contact member 152" may be laterally shifted/offset relative to the base 154B so as to not be aligned with the base 154B while extending in parallel to the base 154B. As a result, an alternating arrangement of the contact members 152', 152" may provide a staggered positioning of the soldering points 162A, 162B for the electrical contacts 152A, 152B (e.g., FIGS. 13-14). In an example, embodiment, the soldering points 162A, 162B are configured for engagement with corresponding apertures in a printed circuit board within the housing 120. As a result, the soldering points 162A, 162B may establish a mechanical and electrical connection between the contact members 152', 152" (which form the electrical contacts 152A, 152B) and the power source 150 and/or control circuitry 160 disposed within the housing 120.

In at least one example embodiment, each of the contact members 152', 152" (of the electrical contacts 152A, 152B) includes a continuous spring feature 156A, 156B that extends from each base 154A, 154B. The continuous spring features 156A, 156B may have a planar, winding form. The continuous spring features 156A, 156B are movable between a first compressed position and a second extended position (e.g., in a perpendicular direction relative to each base 154A, 154B).

In at least one example embodiment, each of the contact members 152', 152" (of the electrical contacts 152A, 152B) includes a contact pin or contact surface 158A, 158B that extends from the respective continuous spring features 156A, 156B. For example, the contact surfaces 158A, 158B extend from the respective continuous spring features 156A, 156B at an end distal from the base 154A, 154B. The contact surfaces 158A, 158B may extend from the respective continuous spring features 156A, 156B and into the capsule-receiving cavity 130, such that the contact surfaces 158A, 158B may make contact with the capsule 200 therein (e.g., via end sections of the capsule 200 analogous to the first end section 1342 and the second end section 1346 of the capsule 1300).

In this manner, the contact surfaces 158A, 158B are spring-loaded so as to enhance an engagement with the capsule 200. For example, the contact surfaces 158A, 158B may extend into the capsule-receiving cavity 130 by a first amount when in use and by a second amount when not in use. The first amount may be smaller than the second amount. For example, when in use, the contact surfaces 158A, 158B may extend into the capsule-receiving cavity 130 by about 0.20 mm (i.e., first amount) as a result of the continuous spring features 156A, 156B being in a compressed or loaded state. On the other hand, when not in use, the contact surfaces 158A, 158B may extend into the capsule-receiving cavity 130 by about 0.90 mm (i.e., second amount) as a result of the continuous spring features 156A, 156B being in an uncompressed or unloaded state. In this manner, in at least one example embodiment, the electrical contacts 152A, 152B are configured such that a connection with the capsule 200 is not established until the full insertion of the capsule 200 into the capsule-receiving cavity 130.

Figure 11:
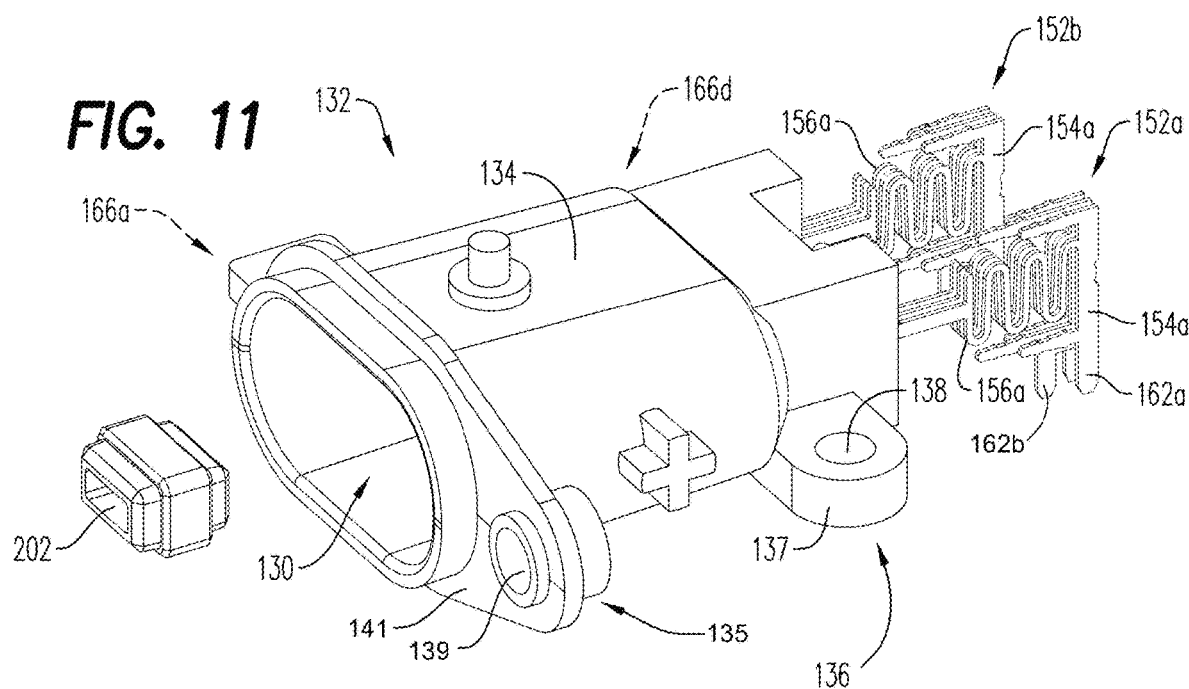
FIG. 11 is an exploded perspective view of a capsule connector in accordance with at least one example embodiment.

In at least some example embodiments, as illustrated best in FIG. 11, each of the electrical contacts 152A, 152B may be formed of a combination of both the contact member 152' and the contact member 152" (e.g., FIG. 14). For instance, the electrical contact 152A may include a contact member 152" between a pair of contact members 152'. Similarly, the electrical contact 152B may include a contact member 152" between a pair of contact members 152'. Although the electrical contacts 152A, 152B are shown as including three contact members each, it should be understood that example embodiments are not limited thereto. Specifically, in other instances, the electrical contacts 152A, 152B may include more (e.g., 4 contact members each) or less (e.g., 1-2 contact members each) than the three contact members each shown in the drawings. Because the contact members 152', 152" of the electrical contacts 152A, 152B are separate structures configured to allow for independent mechanical/electrical engagement, an improved electrical connection can be established between the electrical contacts 152A, 152B and the capsule 200 (via end sections of the capsule 200 analogous to the first end section 1342 and the second end section 1346 of the capsule 1300). Notably, a more reliable and flexible connection with the power source 150 and/or control circuitry 160 may be provided by the separate constituent structures of the electrical contacts 152A, 152B.

In at least some example embodiments, the method of control/heating and associated circuitry and electrical contacts (e.g., capsule connector 132 including the one or more electrical connectors or contacts 152A, 152B) may be as described in U.S. application Ser. No. 17/151,375, titled "Heat-Not-Burn (HNB) Aerosol-Generating Devices Including Energy Based Heater Control, And Methods Of Controlling A Heater", filed concurrently herewith; and U.S. application Ser. No. 17/151,409, titled "Heat-Not-Burn (HNB) Aerosol-Generating Devices Including Intra-Draw Heater Control, and Methods of Controlling a Heater", filed concurrently herewith, the entire contents of each of which are incorporated herein by reference.

The capsule 200 is loaded into the aerosol-generating device 100 by initially inserting the capsule 200 into the capsule-receiving cavity 130 defined by the capsule connector 132. In at least some example embodiments, the capsule 200 makes contact (e.g., full contact) with the electrical contacts 152A, 152B within capsule-receiving cavity 130 only upon the application of force (e.g., downward/inward force) to the capsule 200. In at least one example embodiment, a force is applied to the capsule 200 by the closure and/or latching of the lid 110. In other example embodiments, a force is applied to the capsule 200 by an adult consumer. In still other example embodiments, a force is applied by a combination of pressure applied by the adult consumer and the closure and/or latching of the lid 110. For example, in each instance, a force is applied until a resistance is felt and/or a clicking sound is heard, which signals a complete engagement of the capsule 200 in the capsule-receiving cavity 130.

The underside of the lid 110 may include an impingement/engagement member or surface 113 configured to engage the capsule 200 when the lid 110 is pivoted to transition to a closed position. The impingement/engagement member or surface 113 of the lid 110 may include a recess (e.g., that corresponds to the size and shape of the capsule 200) and/or a resilient material to enhance an interface with the capsule 200 so as to provide the desired seal. When the capsule 200 is inserted into the capsule-receiving cavity 130, the weight of the capsule 200 itself may not be sufficient to compress the electrical contacts 152A, 152B (e.g., at least not to any significant degree). As a result, the capsule 200 may simply rest on the exposed pins of the electrical contacts 152A, 152B (e.g., contact surfaces 158A, 158B of the contact members 152'/152") without any compression (or without any significant compression) of the electrical contacts 152A, 152B. Additionally, the weight of the lid 110 itself, when pivoted to transition to a closed position, may not compress the electrical contacts 152A, 152B to any significant degree and, instead, may simply rest on the capsule 200 in an intermediate, partially open/closed position. In such an instance, a deliberate action (e.g., downward force) to close the lid 110 will cause the impingement/engagement member or surface 113 of the lid 110 to press down onto the capsule 200 to provide the desired seal and also cause the capsule 200 to compress and, thus, fully engage electrical contacts 152A, 152B. Additionally, a full closure of the lid 110 will result in an engagement with the latch 114, which will maintain the closed position and the desired mechanical/electrical engagements involving the capsule 200 until released (e.g., via the latch release button 118). The force requirement for closing the lid 110 may help to ensure and/or improve air/aerosol sealing and to provide a more robust electrical connection, as well as improved device and thermal efficiency and battery life by reducing or eliminating early power draws and/or parasitic heating of the capsule 200.

In at least some example embodiments, such as best illustrated in FIG. 11, the capsule-receiving cavity 130 includes a first or top end 166A and a second or bottom end 166D distal from the first end 166A. For example, the contact surfaces 158A, 158B may extend through the second end 166D of the capsule-receiving cavity 130. When the lid 110 is in a closed position, the first end 166A may be in communication with the lid 110 and/or replaceable mouthpiece 190. In at least some example embodiments, the first end 166A has a first width and the second end 166D has a second width. The first width may be greater than the second width. For example, in at least one example embodiment, a first cross-sectional dimension of the capsule-receiving cavity 130 at the first end 166A may be 7.2 mm×13.6 mm, and the second cross-sectional dimension of the capsule-receiving cavity 130 at the second end 166D may be 6.2 mm×12.6 mm, when the capsule 200 has a cross-sectional dimension of 6.0 mm×12.4 mm. In this manner, in at least one example embodiment, the capsule-receiving cavity 130 may be tapered between the first end 166A and the second end 166D (e.g., 5-15% decrease in a width/lateral dimension), such that the capsule-receiving cavity 130 is configured to steer the capsule 200 into position. The tapered configuration may also improve moldability, as well as providing for a thin air layer around the capsule 200 (e.g. for thermal insulation) during use of the device 200.

Figure 12:
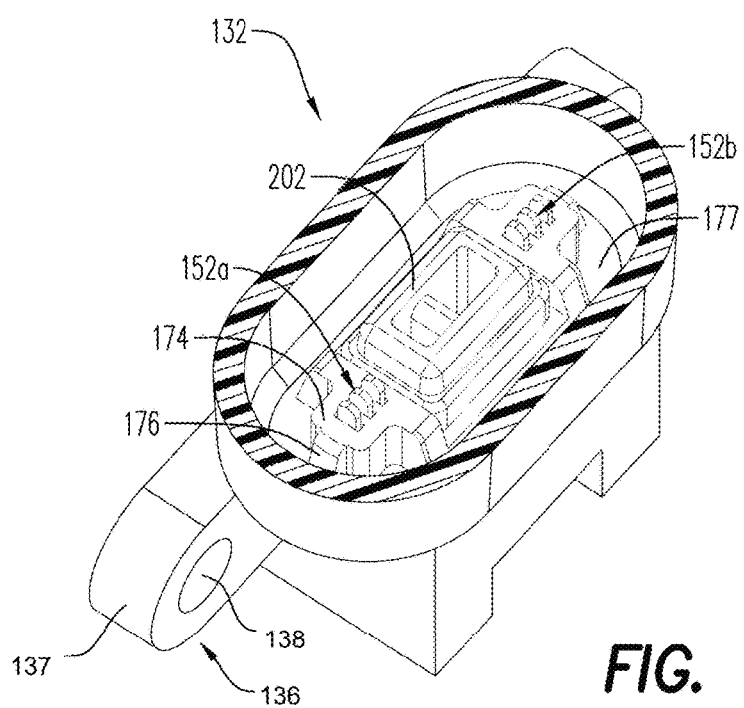
FIG. 12 is a top, front perspective view of the capsule connector illustrated in FIG. 11.
Figure 15:
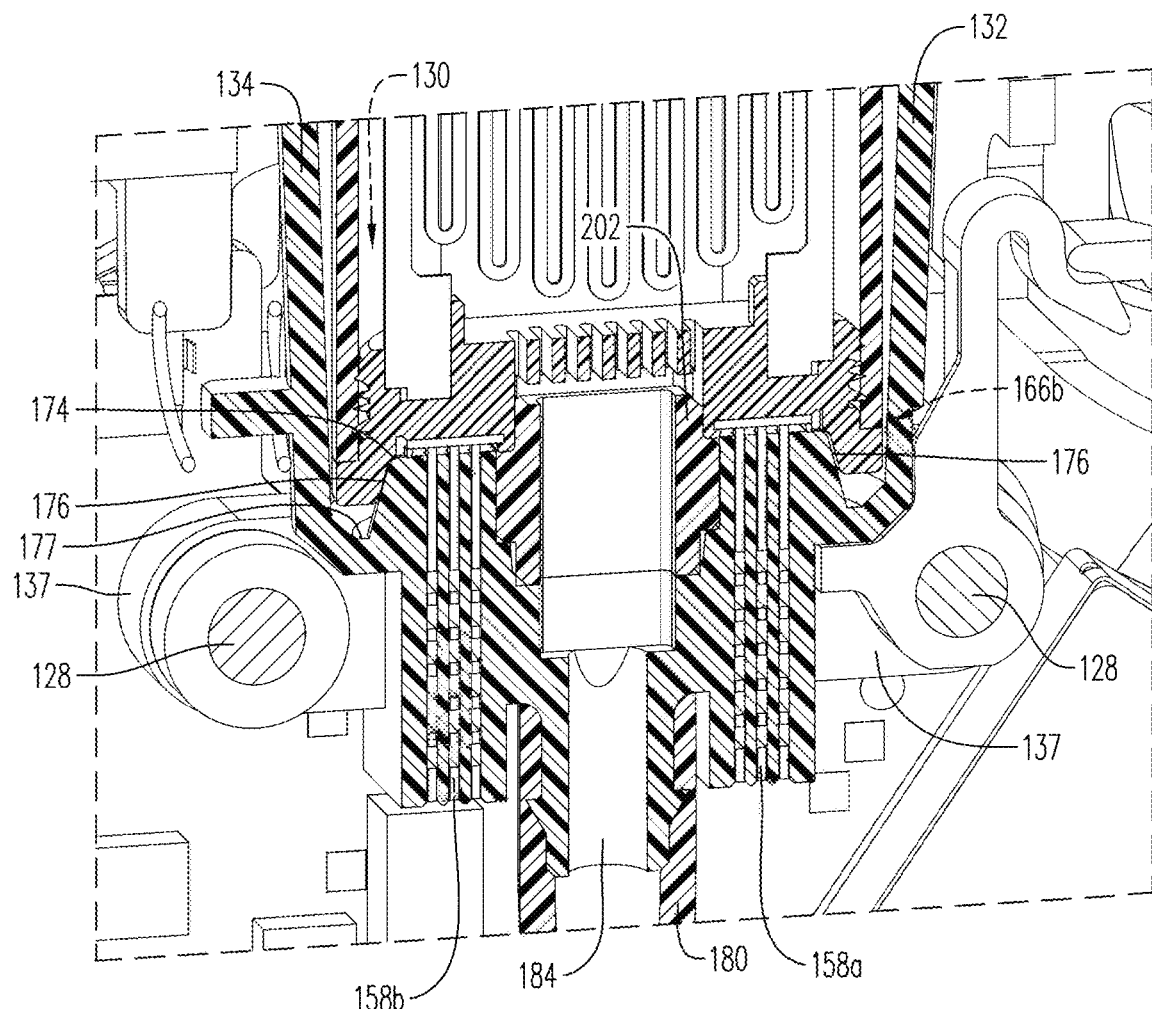
FIG. 15 is a partial cross-sectional view of the capsule connector illustrated in FIG. 11 as disposed in the aerosol-generating device illustrated in FIG. 9.
Figure 16:
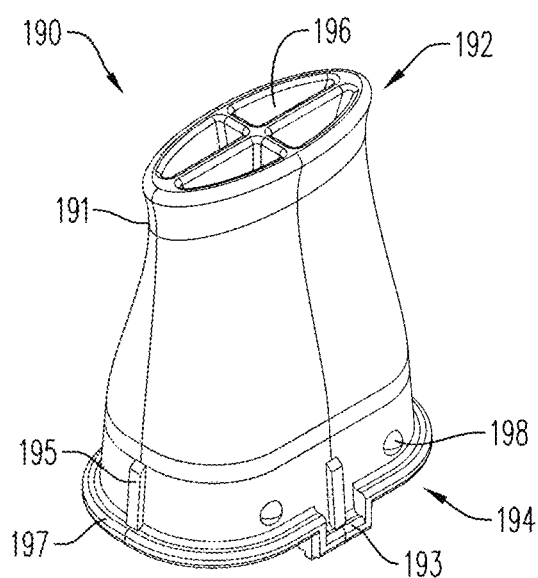
FIG. 16 is a top right, front perspective view of a replaceable mouthpiece in accordance with at least one example embodiment.
Figure 17:
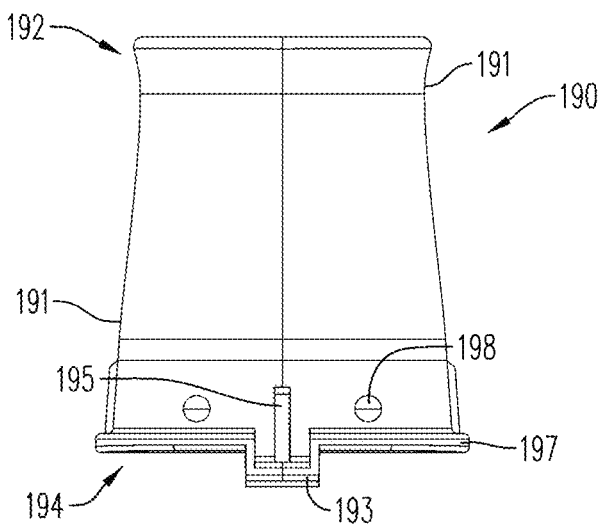
FIG. 17 is a front view of the replaceable mouthpiece illustrated in FIG. 16.
Figure 18:
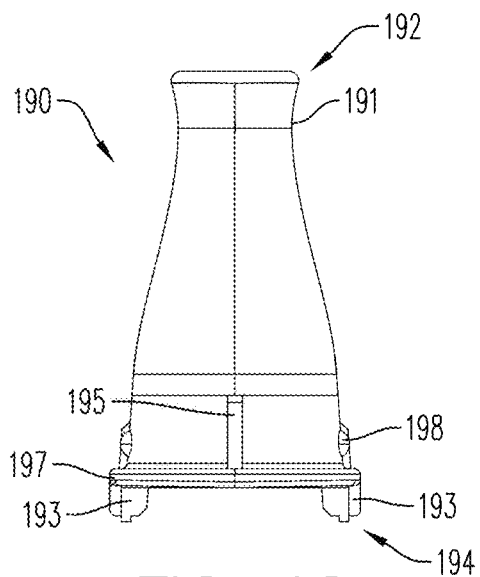
FIG. 18 is a first side view of the replaceable mouthpiece illustrated in FIG. 16.
Figure 19:
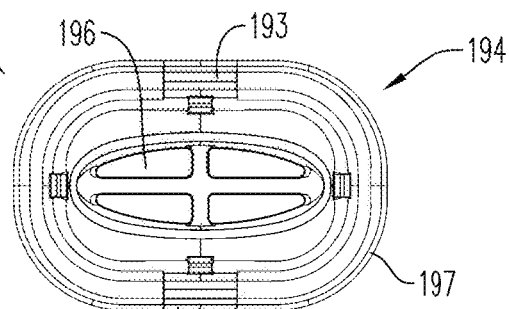
FIG. 19 is a bottom view of the replaceable mouthpiece illustrated in FIG. 16.
Figure 20:
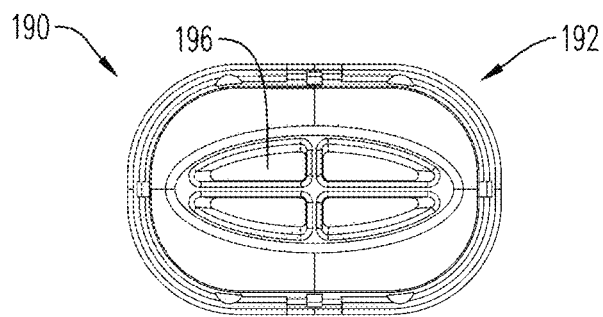
FIG. 20 is a top view of the replaceable mouthpiece illustrated in FIG. 16.

In at least some example embodiments, such as best illustrated in FIGS. 12 and 15, the bottom end 166D of the capsule-receiving cavity 130 includes a capsule seal 202. When the capsule 200 is seated within the capsule-receiving cavity 130, the capsule seal 202 is configured to mate with the inlet recess of the capsule 200 (e.g., inlet recess of the capsule 200 analogous to the inlet recess 1328 of the capsule 1300). The capsule seal 202 may be configured to help ensure and/or improve air/aerosol sealing between the capsule 200 and the capsule connector 132 such that all (or substantially all) of the air received via the air inlet connection 184 is directed into the capsule 200. In at least one example embodiment, the capsule seal 202 may be a silicone seal.

In at least some example embodiments, the bottom end 166D of the capsule-receiving cavity 130 includes one or more alignment members that are configured to help ensure a correct alignment between the capsule 200 and the electrical contacts 152A, 152B. In at least one example embodiment, as best illustrated in FIGS. 12 and 13, the one or more alignment members may include one or more flat surfaces 174 and/or one or more angled surfaces 176. The one or more flat surfaces 174 may provide hard stops for the capsule 200, and the electrical contacts 152A, 152B may extend through the one or more flat surfaces 174. As illustrated, a pair of flat surfaces 174 may be provided, wherein the capsule seal 202 is disposed between the flat surfaces 174. The one or more angled surfaces 176 may include one or more 15° draft surfaces (e.g., 0.05 mm smaller than an equivalent profile on the capsule 200) that extend downwards from the one or more flat surfaces 174 to a surrounding depth 177, which is the deepest depth or bottom of the capsule-receiving cavity 130. In an example embodiment, the alignment members may resemble a pair of plateaus, wherein angled surfaces 176 (e.g., ramps) rise up from the surrounding depth 177 to the flat surfaces 174. Additionally, in some instances, three angled surfaces 176 may lead up to each flat surface 174.

The distal/upstream end of the capsule 200 may have a shape that corresponds with the one or more alignment members formed within the capsule-receiving cavity 130. As a result, the capsule 200 may be properly aligned in a relatively simple and consistent manner when loaded within the aerosol-generating device 100. When the capsule 200 is inserted into the capsule-receiving cavity 130, the end sections of the capsule 200 (which may be analogous to the first end section 1342 and the second end section 1346 of the capsule 1300) may initially come to rest on the electrical contacts 152A, 152B. A downward/inward force on the capsule 200 (e.g., via the closing of the lid 110) will urge the capsule 200 downward/inward so as to cause the electrical contacts 152A, 152B to compress (e.g., via the spring features 156A, 156B of the contact members 152', 152") and, thus, retract into the capsule connector 132. As a result, while pressed against the electrical contacts 152A, 152B, the end sections of the capsule 200 (which may be analogous to the first end section 1342 and the second end section 1346 of the capsule 1300) may also contact the flat surfaces 174 of the alignment members in the capsule-receiving cavity 130. Additionally, the alignment recess of the capsule 200 (which may be analogous to the alignment recess 1326 of the capsule 1300) may contact or otherwise be adjacent to the angled surfaces 176 of the alignment members in the capsule-receiving cavity 130. Furthermore, the inlet recess of the capsule 200 (which may be analogous to the inlet recess 1328 of the capsule 1300) may receive the capsule seal 202 for a resilient engagement. In such instances, a relatively close fit and, consequently, a secure electrical connection and desirable seal may be established with the capsule 200.

FIGS. 16-20 are illustrations of the replaceable mouthpiece 190. In at least some example embodiments, the replaceable mouthpiece 190 includes a first end 192 and a second end 194 distal from the first end 192. In at least one example embodiment, the replaceable mouthpiece 190 may be tapered between the first end 192 and the second end 194. For example, the diameter or average length/width dimensions of the first end 192 may be smaller than the diameter or average length/width dimensions of the second end 194. Towards the first end 192, the taper may have a slight inward curvature 191 that is configured to receive the lips of an adult consumer and improve the comfort and experience.

The first end 192 may have an oblong or elliptical shape and may include one or more outlets 196. For example, as illustrated, the first end 192 may include four outlets 196, such that four or more different areas or quadrants of the adult consumer's mouth can be engaged during use of the aerosol-generating device 100.

The second end 194 may be coupleable to the lid 110. For example, in at least one example embodiment, the second end 194 includes a ledge 197, one or more ridges 195, and one or more coupling structures 198. The ledge 197 may include a recessed portion 193 and, in at least some example embodiments, the one or more ridges 195 may extend perpendicularly (or substantially in a perpendicular direction) from the recessed portion 193. In other example embodiments, the one or more ridges 195 may extend perpendicularly (or substantially in a perpendicular direction) from a main surface of the ledge 197. The ledge 197 and the one or more ridges 195 may be configured to position or align the replaceable mouthpiece 190 with respect to the lid 110. The one or more coupling structures 198 may be configured to couple the replaceable mouthpiece 190 to the lid 110. The one or more coupling structures 198 may be bubble or projection couplers. For example, as illustrated, the replaceable mouthpiece 190 may include four bubble or projection couplers, two disposed along each major length of the second end 194 of the replaceable mouthpiece 190.

In at least some example embodiments, the replaceable mouthpiece 190 may be inserted through an opening 111 of the lid 110 that is configured to receive and secure the second end 194 of the replaceable mouthpiece 190 (e.g., via a snap-fit arrangement). In this manner, as illustrated best in FIGS. 1, 6, and 9, the ledge 197, the one or more ridges 195, and the one or more coupling structures 198 are covered by the lid 110 when assembled with the aerosol-generating device 100. For example, only the tapered portion and the first end 192 of the replaceable mouthpiece 190 may be visible once the aerosol-generating device 100 is assembled. Furthermore, as a result of the mating features (e.g., coupling structures 198), a confirmatory feedback (e.g., audible click) may be provided when the replaceable mouthpiece 190 is properly engaged with the lid 110.

Figure 21:
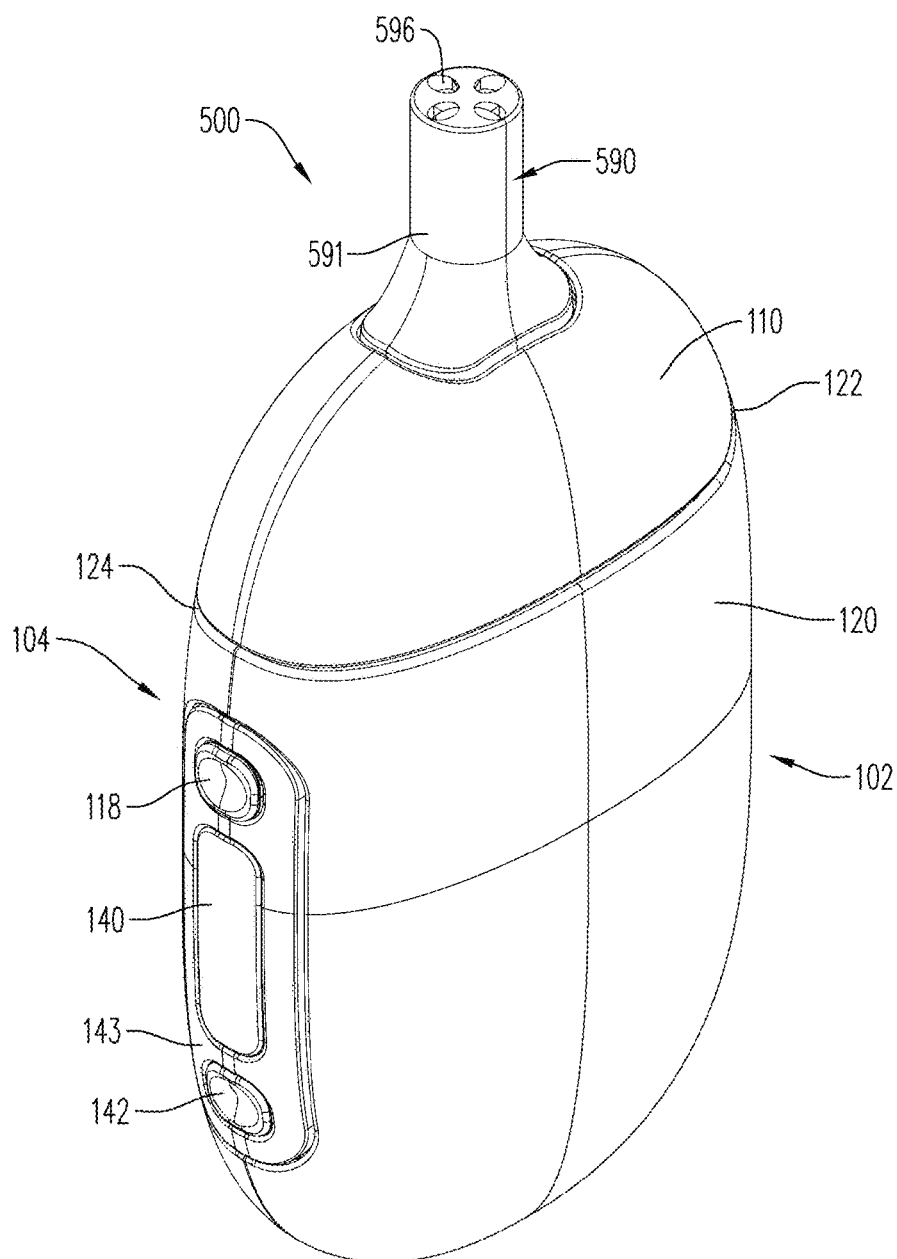
FIG. 21 is a top right, front perspective view of another aerosol-generating device in accordance with at least one example embodiment.
Figure 25:
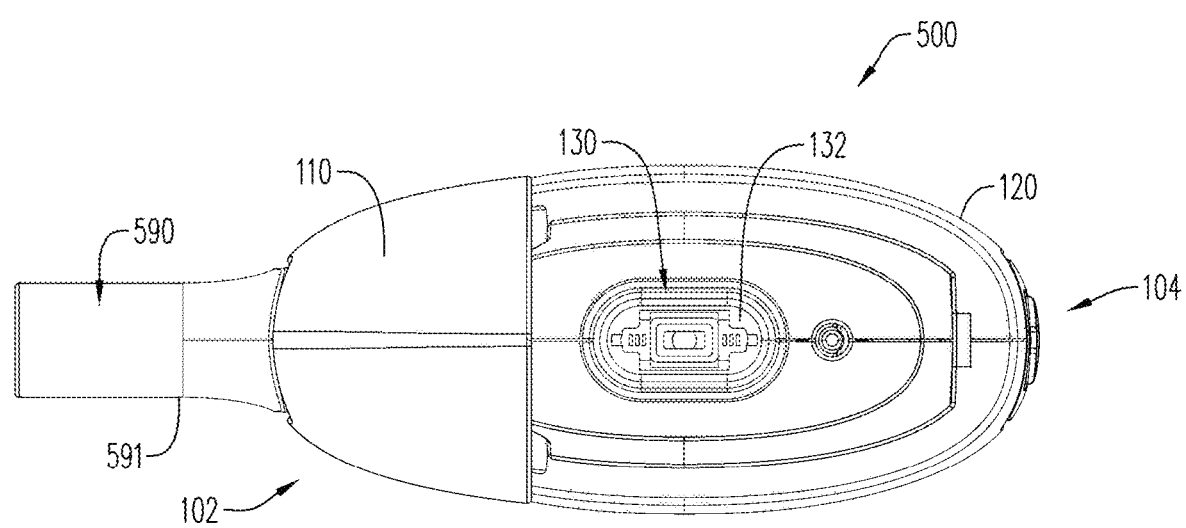
FIG. 25 is a top view of the aerosol-generating device illustrated in FIG. 24.
Figure 26:
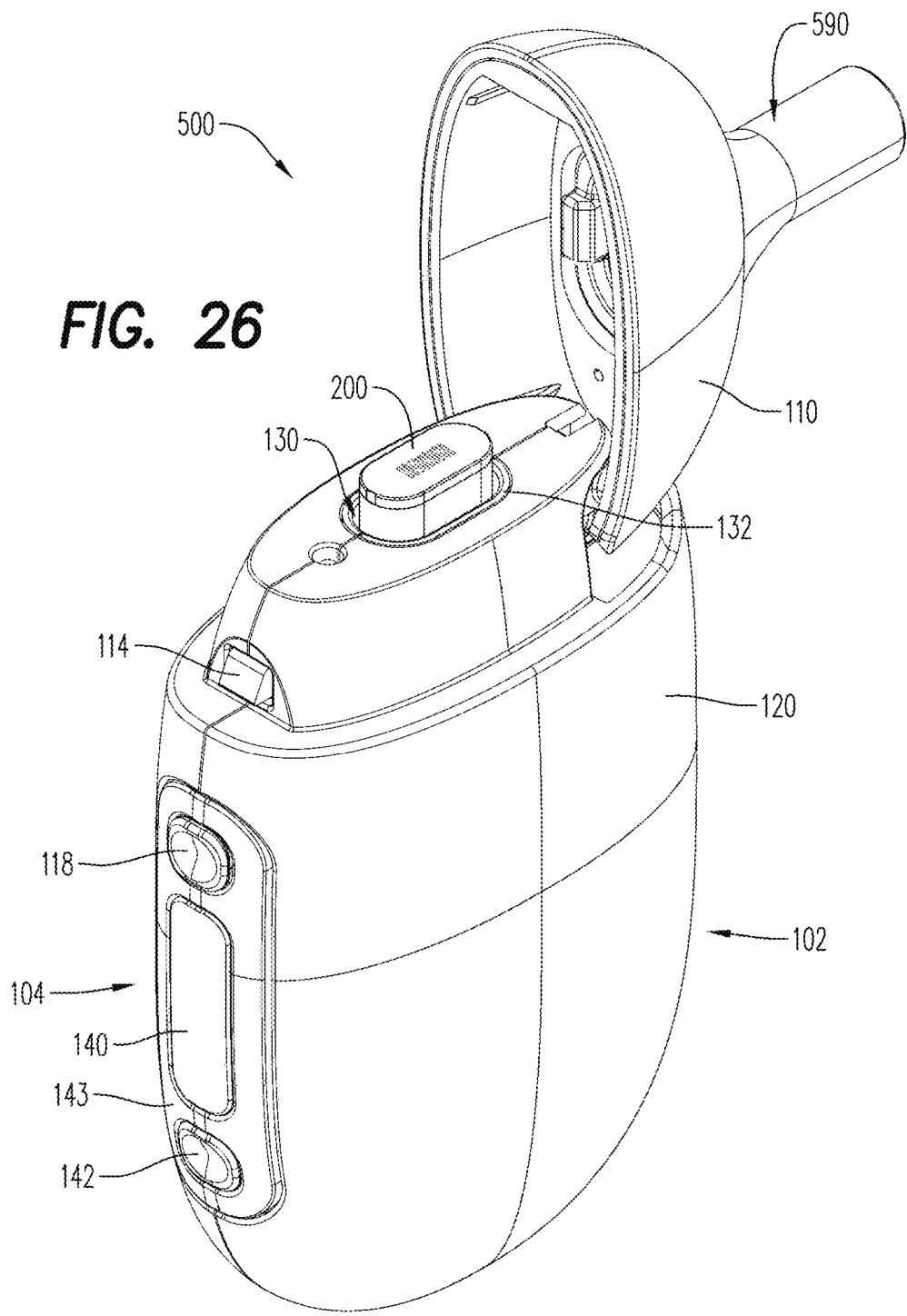
FIG. 26 is a top right, front perspective view of the aerosol-generating device illustrated in FIG. 24 receiving a capsule.
Figure 27:
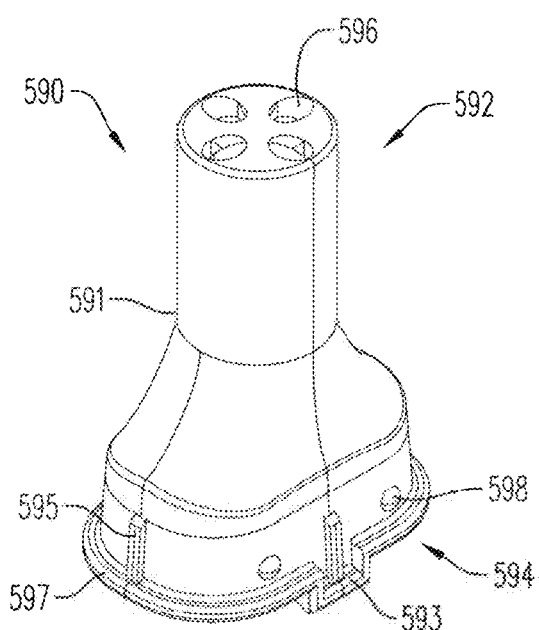
FIG. 27 is a top right, front perspective view of another replaceable mouthpiece in accordance with at least one example embodiment.
Figure 28:
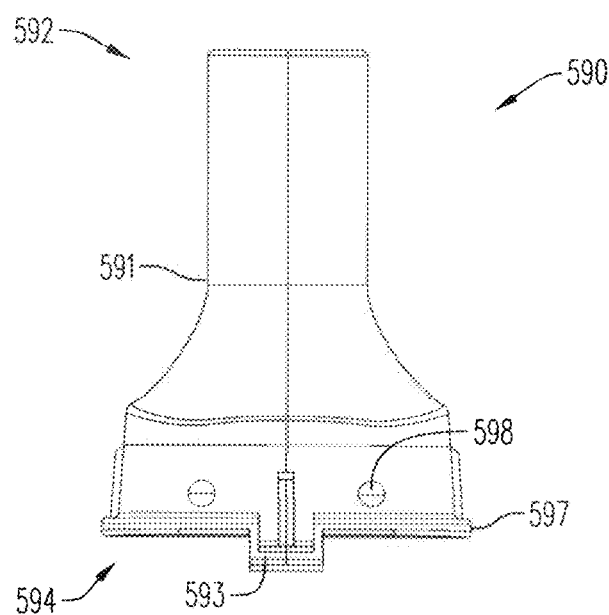
FIG. 28 is a front view of the replaceable mouthpiece illustrated in FIG. 27.
Figure 29:
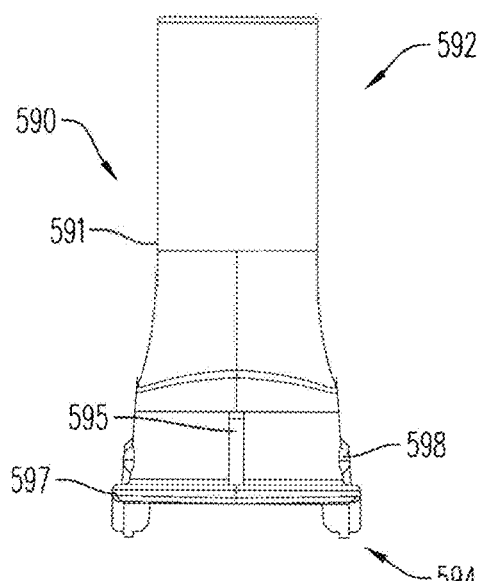
FIG. 29 is a side view of the replaceable mouthpiece illustrated in FIG. 27.
Figure 30:
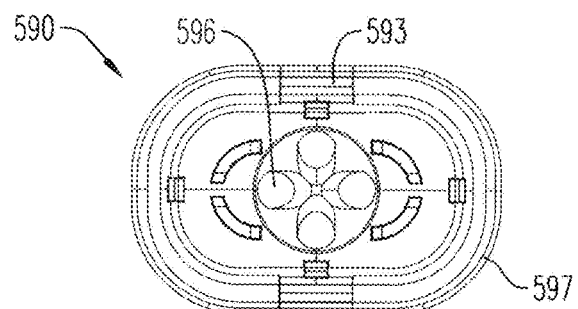
FIG. 30 is a bottom view of the replaceable mouthpiece illustrated in FIG. 27.
Figure 31:
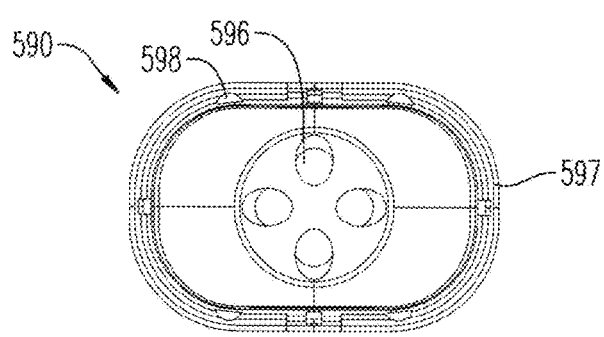
FIG. 31 is a top view of the replaceable mouthpiece illustrated in FIG. 27.

FIGS. 21-26 are illustrations of an aerosol-generating device 500 (e.g., heat-not-burn (HNB) aerosol-generating device) in accordance with at least one example embodiment. The aerosol-generating device 500 is the same as the aerosol-generating device 100 except the aerosol-generating device 500 includes a cylindrical mouthpiece 590. For example, FIG. 21 is a top perspective view of the aerosol-generating device 500, where the lid 110 is closed. FIG. 22 is a bottom perspective view of the aerosol-generating device 500, where the lid 110 is closed. FIG. 23 is a top-down view of the aerosol-generating device 500, where the lid 110 is closed. FIG. 24 is another top perspective view of the aerosol-generating device 500, where the lid 110 is opened. FIG. 25 is a top-down view of the aerosol-generating device 500, where the lid 110 is opened. FIG. 26 is another top perspective view of the aerosol-generating device 500, where the lid 110 is opened and a capsule 200 is received by the capsule receiving cavity 130.

FIGS. 27-31 are illustrations of the replaceable mouthpiece 590. In at least some example embodiments, the replaceable mouthpiece 590 includes a first end 592 and a second end 594 distal from the first end 592. Different from the replaceable mouthpiece 190, the first end 592 of the replaceable mouthpiece 590 may have a substantially cylindrical shape. Though only two shapes are illustrated, the skilled artisan will recognize that the first ends 192, 592 of the replaceable mouthpieces 190, 590 may take a variety of other configurations. The second end 594 of the replaceable mouthpiece 590 may have a shape the same or similar as the second end 194 of the replaceable mouthpiece 190, such that the replaceable mouthpiece 590 may be similarly engaged by an opening 111 of the lid 110.

For example, in at least one example embodiment, the replaceable mouthpiece 590 may be tapered between the first end 592 and the second end 594. For example, the diameter of the first end 592 may be smaller than the diameter or average length/width dimensions of the second end 594. Towards the first end 592, the taper may have a slight inward curvature 591 that is configured to receive the lips of an adult consumer and improve the comfort and experience.

The first end 592 of the replaceable mouthpiece 590 includes one or more outlets 596. For example, as illustrated, the first end 592 may include four outlets 596 (e.g., diverging outlets), such that four or more different areas or quadrants of the consumer's mouth can be engaged during use of the aerosol-generating device 500.

The second end 594 is coupleable to the lid 110. For example, in at least one example embodiment, the second end 594 includes a ledge 597, one or more ridges 595, and one or more coupling structures 598. The ledge 597 may include a recessed portion 593 and, in at least some example embodiments, the one or more ridges 595 may extend perpendicularly (or substantially in a perpendicular direction) from the recessed portion 593. In other example embodiments, the one or more ridges 595 may extend perpendicularly (or substantially in a perpendicular direction) from a main surface of the ledge 597. The ledge 597 and the one or more ridges 595 may be configured to position or align the replaceable mouthpiece 590 with respect to the lid 110. The one or more coupling structures 598 may be configured to couple the replaceable mouthpiece 590 to the lid 110. The one or more coupling structures 598 may be bubble or projection couplers. For example, as illustrated, the replaceable mouthpiece 590 may include four bubble or projection couplers, two disposed along each major length of the second end 594 of the replaceable mouthpiece 590.

In at least some example embodiments, the aerosol-generating device in accordance with at least some example embodiments (such as the aerosol-generating device 100 illustrated in FIGS. 1-10 and/or the aerosol-generating device 500 illustrated in FIGS. 21-26) are configured to receive a capsule (e.g., capsule 200) that includes an aerosol-forming substrate (e.g., aerosol-forming substrate 1860'). Additional details and/or alternatives for the aerosol-generating device, the capsule, and/or the aerosol-forming substrate may be found in U.S. application Ser. No. 17/151,277, titled "Capsules Including Embedded Heaters And Heat-Not-Burn (HNB) Aerosol-Generating Devices"), filed concurrently herewith; U.S. application Ser. No. 29/766,691, titled "Aerosol-Generating Capsules", filed concurrently herewith; and U.S. application Ser. No. 17/151,336, titled "Heat-Not-Burn (HNB) Aerosol-Generating Devices And Capsules", filed concurrently herewith, the entire contents of each of which are incorporated herein by reference.

As discussed herein, an aerosol-forming substrate is a material or combination of materials that may yield an aerosol. An aerosol relates to the matter generated or output by the devices disclosed, claimed, and equivalents thereof. The material may include a compound (e.g., nicotine, cannabinoid), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

In some example embodiments, the tobacco material may include material from any member of the genus *Nicotiana*. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a *cannabis* plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of *cannabis* plants such as *Cannabis sativa, Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from a heater may cause decarboxylation so as to convert the tetrahydrocannabinolic acid (THCA) in the capsule to tetrahydrocannabinol (THC), and/or to convert the cannabidiolic acid (CBDA) in the capsule to cannabidiol (CBD).

In instances s where both tetrahydrocannabinolic acid (THCA) and tetrahydrocannabinol (THC) are present in the capsule, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule. Similarly, in instances where both cannabidiolic acid (CBDA) and cannabidiol (CBD) are present in the capsule, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule.

Furthermore, the compound may be or may additionally include a non-naturally occurring additive that is subsequently introduced into the fibrous material. In one instance, the fibrous material may include at least one of cotton, polyethylene, polyester, rayon, combinations thereof, or the like (e.g., in a form of a gauze). In another instance, the fibrous material may be a cellulose material (e.g., non-tobacco and/or non-cannabis material). In either instance, the compound introduced may include nicotine, cannabinoids, and/or flavorants. The flavorants may be from natural sources, such as plant extracts (e.g., tobacco extract, cannabis extract), and/or artificial sources. In yet another instance, when the fibrous material includes tobacco and/or cannabis, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of cannabis may be increased through supplementation with an extract containing such cannabinoids.

In at least some example embodiments, the aerosol-generating device in accordance with at least some example embodiments (such as, the aerosol-generating device 100 illustrated in FIGS. 1-10 and/or the aerosol-generating device 500 illustrated in FIGS. 21-26) are configured to heat a capsule (e.g., capsule 200) to generate an aerosol. In an example embodiment, a method of generating an aerosol may include initially loading a capsule 200 into the aerosol-generating device 100 or the aerosol-generating device 500. To load the capsule 200, the lid 110 is pivoted to the open position, and the capsule 200 is inserted into the capsule-receiving cavity 130 defined by the capsule connector 132. Next, pivoting the lid 110 to the closed position such that the lid 110 engages the latch 114 and will maintain the closed position while pressing the capsule 200 further into the capsule-receiving cavity 130 to fully seat the capsule 200.

When the capsule 200 is fully seated within the capsule-receiving cavity 130, the end sections of the capsule 200 (which may be analogous to the first end section 1342 and the second end section 1346 of the capsule 1300) will be pressed against the electrical contacts 152A, 152B (e.g., pressed against the exposed tips of the contact surfaces 158A, 158B of the contact members 152', 152"), which will, in turn, be compressed and retracted via the spring features 156A, 156B of the contact members 152', 152". While pressed against the electrical contacts 152A, 152B, the end sections of the capsule 200 (which may be analogous to the first end section 1342 and the second end section 1346 of the capsule 1300) may also contact the flat surfaces 174 of the alignment members in the capsule-receiving cavity 130. Additionally, the alignment recess of the capsule 200 (which may be analogous to the alignment recess 1326 of the capsule 1300) may contact or otherwise be adjacent to the angled surfaces 176 of the alignment members in the capsule-receiving cavity 130. Furthermore, the inlet recess of the capsule 200 (which may be analogous to the inlet recess 1328 of the capsule 1300) may receive the capsule seal 202 for a resilient engagement. As a result, a relatively secure electrical connection and desirable seal may be established with the capsule 200.

The aerosol-generating device 100 or the aerosol-generating device 500 may be activated using the consumer interface panel 143 (e.g., by pressing the power button 142) and/or upon the detection of a draw event (e.g., via the flow sensor 185). Upon activation, the control circuitry 160 is configured to instruct the power source 150 to supply an electrical current to the capsule 200 via the electrical contacts 152A, 152B in the capsule-receiving cavity 130. Specifically, the capsule 200 includes a heater (which may be analogous to the heater 1340 of the capsule 1300) that is configured to undergo resistive heating in response to the electrical current from the power source 150 that is introduced via its end sections (which may be analogous to the first end section 1342 and the second end section 1346 of the capsule 1300). As a result of the resistive heating, the temperature of the aerosol-forming substrate within the capsule 200 will increase such that volatiles are released so as to generate an aerosol.

In at least one example embodiment, the heating of the aerosol-forming substrate within the capsule 200 may be below a combustion temperature of the aerosol-forming substrate so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental. The method of heating/control may be as described in U.S. application Ser. No. 17/151,375, titled "Heat-Not-Burn (HNB) Aerosol-Generating Devices Including Energy Based Heater Control, And Methods Of Controlling A Heater", filed concurrently herewith; and U.S. application Ser. No. 17/151,409, titled "Heat-Not-Burn (HNB) Aerosol-Generating Devices Including Intra-Draw Heater Control, and Methods of Controlling a Heater", filed concurrently herewith, the entire contents of each of which are incorporated herein by reference.

Upon a draw or application of negative pressure to the aerosol-generating device 100 (e.g., via the mouthpiece 190) or the aerosol-generating device 500 (e.g., via the mouthpiece 590), ambient air is drawn into the aerosol-generating device 100 or the aerosol-generating device 500 through the pores 173 in the grille 172. Once inside, the air streams from the pores 173 converge and may pass through an air channel assembly 181 before being directed to the air hose 180. The converged airflow may be optionally detected/monitored with a flow sensor 185 within the air channel assembly 181 and/or the air hose 180. From the air hose 180, the airflow is directed to the air inlet connection 184 of the capsule connector 132. The airflow then travels through the capsule seal 202 and enters the inlet openings in the capsule 200 (which may be analogous to the openings 1322 in the capsule 1300). Inside the capsule 200, the air may flow (e.g., longitudinally) through the aerosol-forming substrate and along the plane of the heater so as to entrain the volatiles released by the aerosol-forming substrate, which results in an aerosol. Finally, the resulting aerosol passes through the outlet openings in the capsule 200 (which may be analogous to the openings 1312 in the capsule 1300) before exiting the aerosol-generating device 100 (e.g., via the outlets 196 in the mouthpiece 190) or the aerosol-generating device 500 (e.g., via the outlets 596 in the mouthpiece 590).

In at least some example embodiments, the method of use regarding the aerosol-generating device 100 or the aerosol-generating device 500 may include securing the replaceable mouthpiece (e.g., replaceable mouthpiece 190 and/or replaceable mouthpiece 590) to the lid (e.g., 110). For example, the method may include inserting the replaceable mouthpiece into the opening (e.g., opening 111) of the lid when the lid is in an opened position until resistance is felt and/or a click is heard. In at least some example embodiments, the method of use may include replacing the replaceable mouthpiece (e.g., replaceable mouthpiece 190 and/or replaceable mouthpiece 590). Replacing the replaceable mouthpiece may including opening the lid (e.g., 110); removing a first replaceable mouthpiece from the opening (e.g., opening 111); and inserting a second replaceable mouthpiece into the opening until resistance is felt and/or a click is heard.

Although a capsule 200 has been illustrated as one example in connection with the aerosol-generating device 100 and the aerosol-generating device 500, it should be understood other suitable examples are also available. Further details, variants, and alternatives of the capsule are discussed below in connections with FIGS. 32-46.

Figure 32:
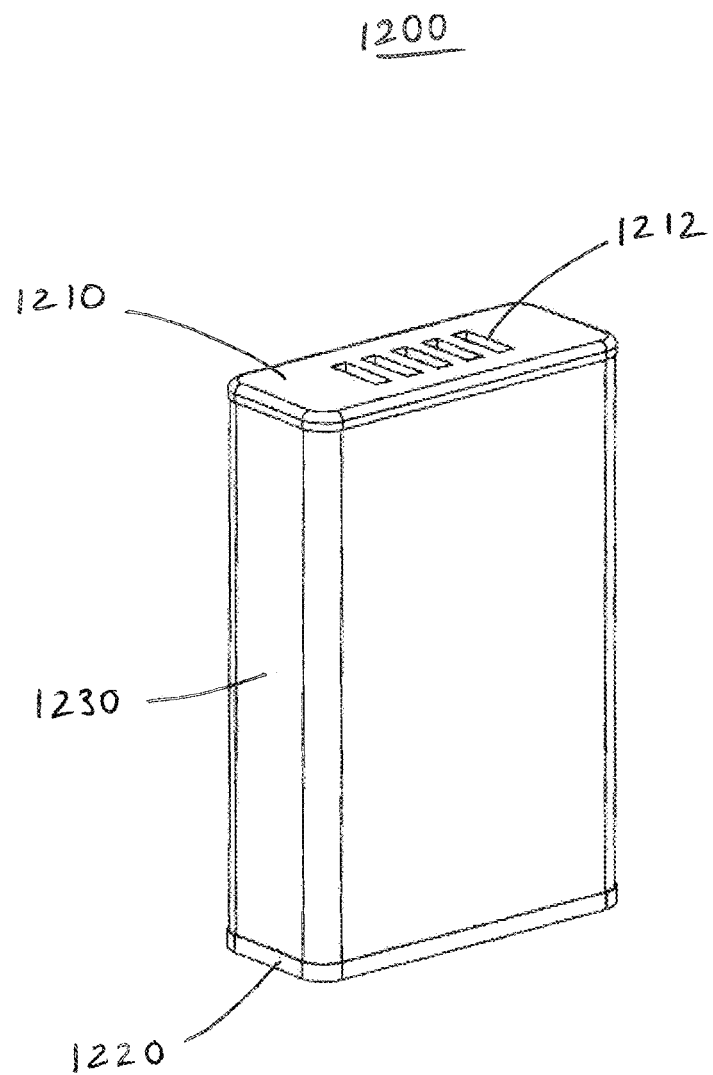
FIG. 32 is a downstream perspective view of a capsule for an aerosol-generating device according to an example embodiment.
Figure 33:
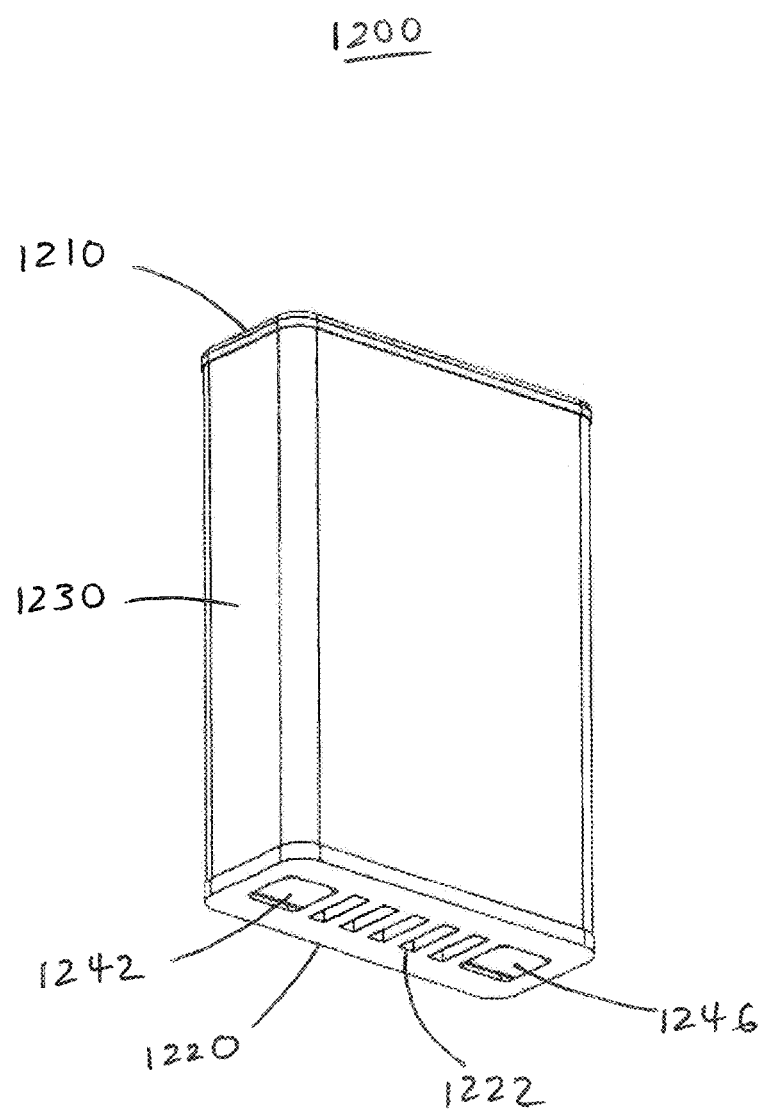
FIG. 33 is an upstream perspective view of the capsule of FIG. 32.

FIG. 32 is a downstream perspective view of a capsule for an aerosol-generating device according to an example embodiment. FIG. 33 is an upstream perspective view of the capsule of FIG. 32. Referring to FIGS. 32-33, a capsule 1200 may include a housing having a downstream portion, an upstream portion, and a body portion between the downstream portion and the upstream portion. The downstream portion of the housing may be in the form of a first end cap 1210 (e.g., downstream cap). The upstream portion of the housing may be in the form of a second end cap 1220 (e.g., upstream cap). The body portion of the housing may be in the form of a cover 1230 (e.g., shell, box sleeve).

The first end cap 1210 defines a first opening 1212, while the second end cap 1220 defines a second opening 1222. In an example embodiment, the first opening 1212 is in the form of a series of outlet openings (e.g., five outlet openings), and the second opening 1222 is in the form of a series of inlet openings (e.g., five inlet openings). In another instance, instead of being arranged in series, the openings may be arranged in an array of rows and columns. Additionally, the second end cap 1220 may expose a first end section 1242 and a second end section 1246 of a heater 1240 (e.g., FIG. 34). As illustrated, the second opening 1222 may be between the exposed portions of the first end section 1242 and the second end section 1246. The first end cap 1210 and the second end cap 1220 may be formed of a high-temperature plastic. Non-limiting examples of suitable high-temperature plastics include liquid crystal polymer (LCP), polyetheretherketone (PEEK), or cyclic olefin copolymer (COC).

Furthermore, the first end cap 1210 and the second end cap 1220 may be of the same color or of different colors (e.g., including transparent). In instances where the first end cap 1210 and/or the second end cap 1220 are transparent, the first end cap 1210 and/or the second end cap 1220 may serve as windows configured to permit a viewing of the contents/components (e.g., aerosol-forming substrate and/or heater) within the capsule 1200. The color(s) of the first end cap 1210 and the second end cap 1220 may be optionally used for stock keeping unit (SKU) identification.

The cover 1230 may be formed of a metal/alloy, a high-temperature plastic, and/or a plant material. In some instances, the metal may include aluminum, and the alloy may be stainless steel. The high-temperature plastic may be the same as those disclosed in connection with the first end cap 1210 and the second end cap 1220. The plant material may include cellulose fibers (e.g., in the form of paper pulp). As for dimensions, the cover 1230 may have a thickness (e.g., wall thickness) of about 0.4 mm-0.6 mm (e.g., 0.5 mm), although example embodiments are not limited thereto. In addition to being wholly formed of one of the above materials, the cover 1230 may also have a composite/multi-layer structure. For instance, the cover 1230 may include an underlying/inner layer of metal combined with an overlying/outer layer of plastic and/or plant material (e.g., paper, cardboard).

When a metal/alloy is used to produce the cover 1230, the fabrication process may include extrusion of the metal/alloy to form the cover 1230. In another instance, the fabrication process may include pressing/drawing (e.g., punching an appropriate shape out of a sheet of the metal/alloy) and cutting to form the cover 1230. In yet another instance, the fabrication process may include stamping a sheet of the metal/alloy to an appropriate size/shape and folding to form the cover 1230 followed by an optional seam welding and/or application of a label. These latter two processes may reduce fabrication costs.

The capsule 1200 may have a cuboid-like shape which includes a front face, a rear face opposite the front face, a first side face between the front face and the rear face, a second side face opposite the first side face, a downstream end face, and an upstream end face opposite the downstream end face. To receive the capsule 1200, it should be understood that the capsule-receiving cavity (e.g., capsule-receiving cavity 130 of the aerosol-generating device 100) may be configured to accommodate such a shape. Although the capsule 1200 is illustrated as having a cuboid-like shape (e.g., rounded rectangular cuboid) with a rectangular cross-section, it should be understood that example embodiments are not limited thereto. For instance, in some embodiments, the capsule 1200 may have a shape wherein an end view or cross-section resembles a rectangle with a pair of opposing semicircular ends (e.g., elongated circle, obround, discorectangle, stadium, racetrack), an oval/ovoid, or an ellipse. The chamber defined within the capsule 1200 may have the same or a different shape as the exterior of the capsule 1200. For instance, the cross-sections of the chamber and the exterior of the capsule 1200 may both be rectangular. In another instance, the cross-section of the chamber may be non-rectangular (e.g., obround), while the cross-section of the exterior of the capsule 1200 may be rectangular (or vice versa).

Figure 34:
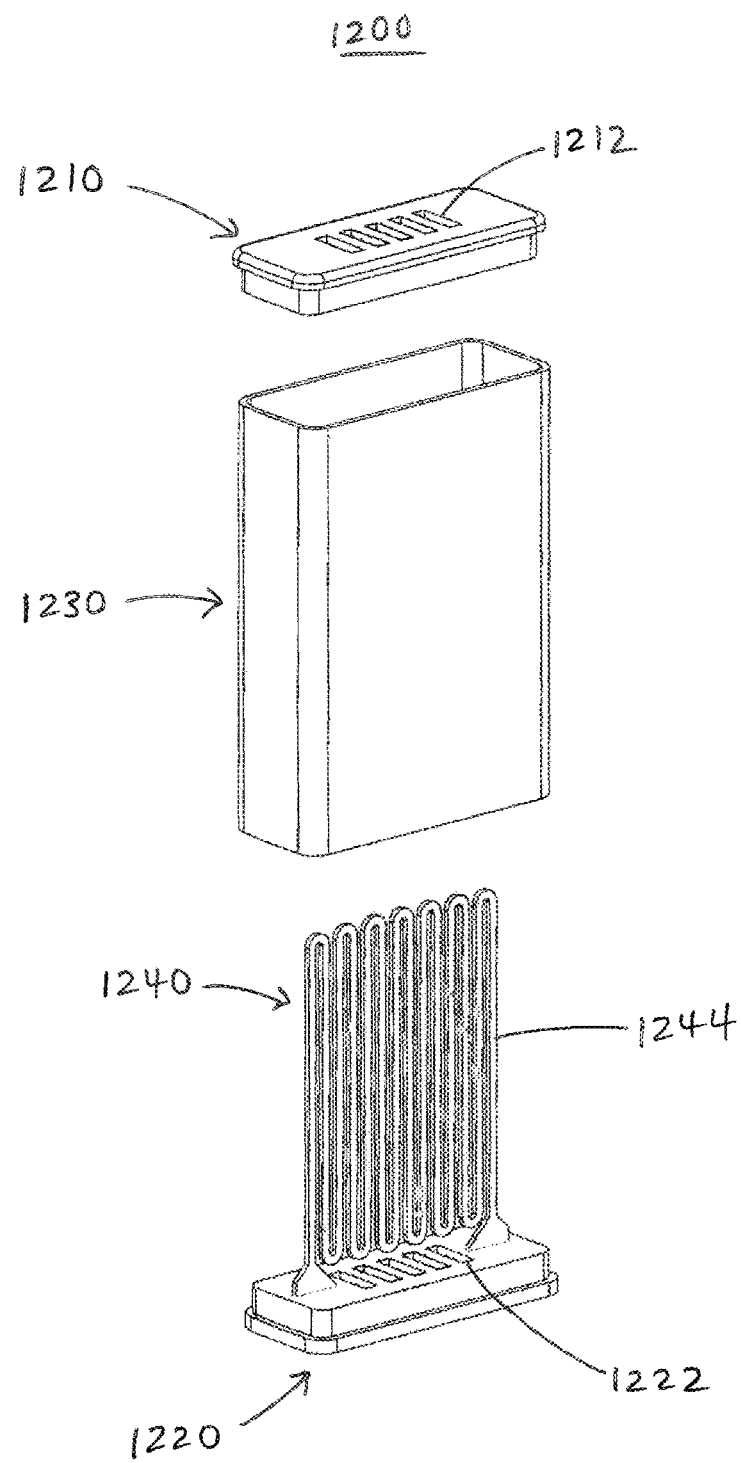
FIG. 34 is an exploded view of the capsule of FIG. 32.
Figure 35:
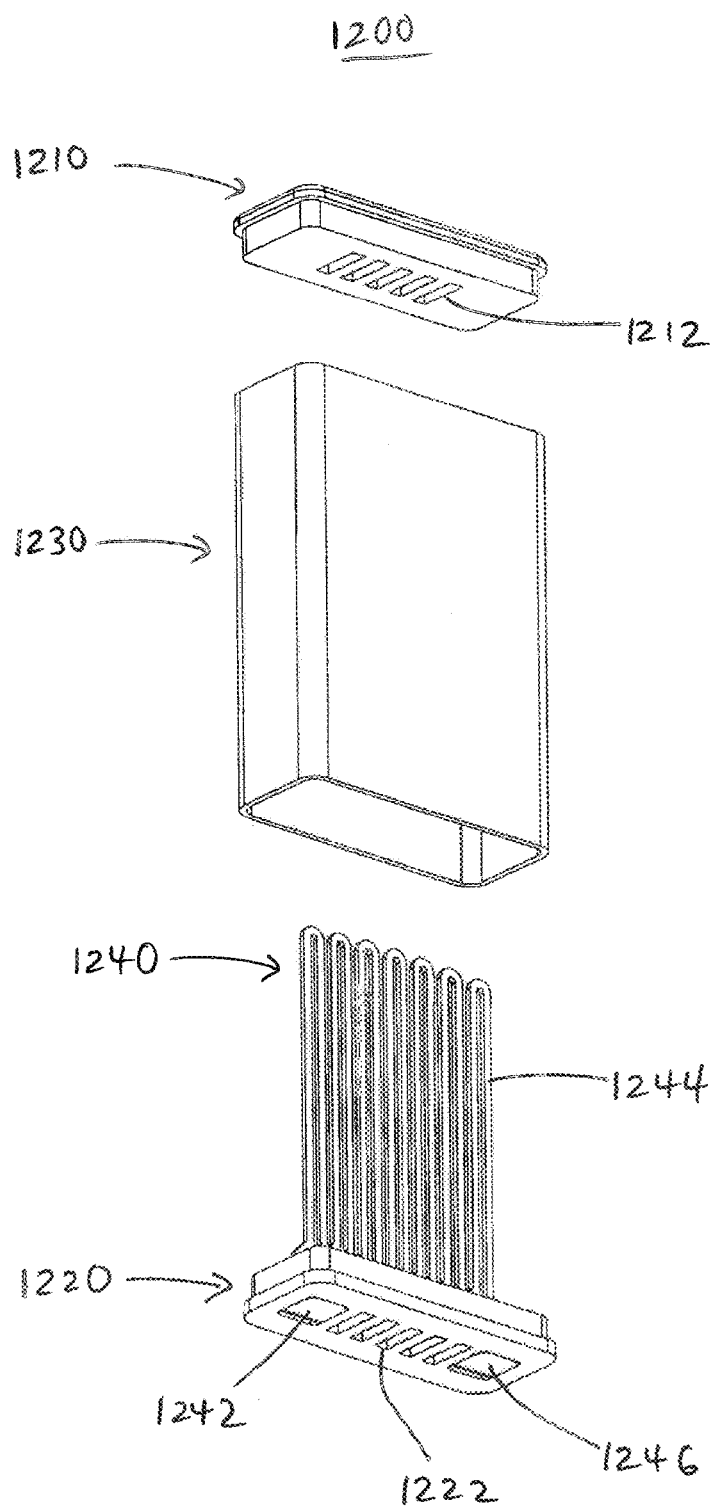
FIG. 35 is an exploded view of the capsule of FIG. 33.

FIG. 34 is an exploded view of the capsule of FIG. 32. FIG. 35 is an exploded, upstream perspective view of the capsule of FIG. 32. Referring to FIGS. 34-35, the first end cap 1210 includes a projecting edge or flange around its periphery. The extent of the protrusion of the projecting edge of the first end cap 1210 may be about equal to the wall thickness of the cover 1230. Similarly, the second end cap 1220 includes a projecting edge or flange around its periphery. The extent of the protrusion of the projecting edge of the second end cap 1220 may also be about equal to the wall thickness of the cover 1230. The first end cap 1210 and the second end cap 1220 are configured to engage with inner surfaces of the cover 1230. The projecting edges of the first end cap 1210 and the second end cap 1220 may function as stoppers when the first end cap 1210 and the second end cap 1220 are being engaged with the cover 1230. Additionally, when the capsule 1200 is assembled, the edges of the first end cap 1210 and the second end cap 1220 may be substantially flush with the adjacent surfaces of the cover 1230.

In an alternative embodiment, the first end cap 1210 may be integrated with the cover 1230 so as to constitute a single structure. For instance, the fabrication process may include pressing/drawing a metal sheet such that the first end cap 1210 and the cover 1230 are integrally formed of the same material (e.g., as a continuous shell). The first opening 1212 may be pre-punched into the metal sheet before the pressing/drawing or post-punched into the metal sheet after the pressing/drawings.

The heater 1240 includes a first end section 1242, an intermediate section 1244, and a second end section 1246. The first end section 1242 and the second end section 1246 include external segments of the heater 1240 configured to establish an electrical connection with a power source (e.g., for receiving an electric current from the power source 150). During manufacturing, the heater 1240 may be embedded within the second end cap 1220 via injection molding (e.g., insert molding, overmolding). The intermediate section 1244 is an internal segment of the heater 1240 configured to heat the aerosol-forming substrate (e.g., aerosol-forming substrate 1860 in FIG. 47). When the capsule 1200 is assembled, the intermediate section 1244 of the heater 1240 may be aligned between the first opening 1212 and the second opening 1222.

The aerosol-forming substrate for the capsule 1200 may be in a consolidated form or in a loose form. Specifically, when in a consolidated form, the aerosol-forming substrate may have a shape that facilitates its placement within the housing. For instance, the aerosol-forming substrate may be in the form of one or more rectangular sheets/slabs dimensioned for insertion into the cover 1230. When in a loose form, the aerosol-forming substrate may be loaded into the cover 1230 via a vacuum-assisted process. With such a process, the housing may first be partially assembled such that the second end cap 1220 (with the heater 1240 embedded therein) is engaged with the cover 1230. A vacuum may then be applied to the second opening 1222 of the second end cap 1220 to pull aerosol-forming substrate provided in the vicinity into the open end of the cover 1230. The level of the vacuum may be varied as appropriate to achieve the desired density of the aerosol-forming substrate for the capsule 1200. In this manner, a plurality of capsules may be loaded simultaneously and relatively consistently.

Figure 36:
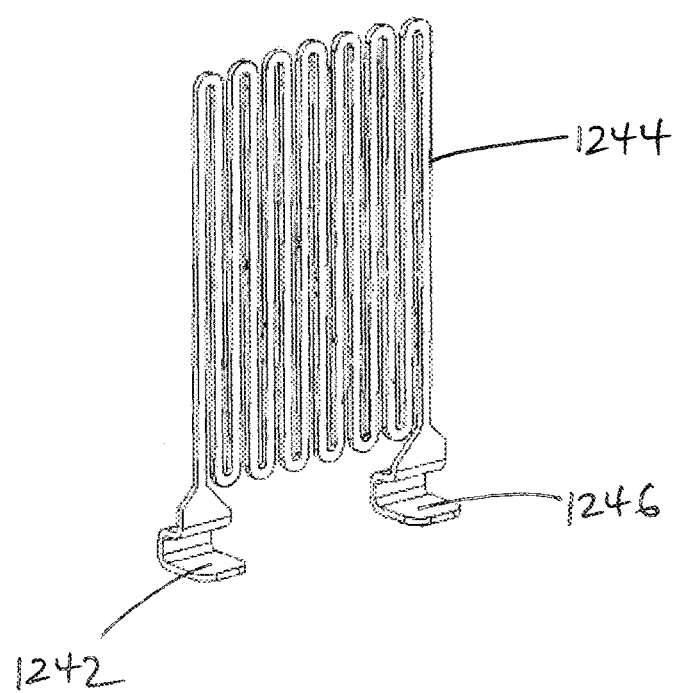
FIG. 36 is an enlarged view of the heater in FIG. 34.

FIG. 36 is an enlarged view of the heater in FIG. 34. A sheet material may be cut or otherwise processed (e.g., stamping, electrochemical etching, die cutting, laser cutting) to produce the heater 1240. In such an instance, the heater 1240 will have an integral, continuous form. The sheet material may be formed of one or more conductors configured to undergo Joule heating (which is also known as ohmic/resistive heating). Suitable conductors for the sheet material include an iron-based alloy (e.g., stainless steel, iron aluminides), a nickel-based alloy (e.g., nichrome), and/or a ceramic (e.g., ceramic coated with metal). For instance, the stainless steel may be a type known in the art as SS316L, although example embodiments are not limited thereto. The sheet material may have a thickness of about 0.10 mm-0.30 mm (e.g., 0.15 mm-0.25 mm). The heater 1240 may have a resistance between 0.5 Ohm-2.5 Ohms (e.g., 1.0 Ohm-2.0 Ohms). Referring to FIG. 36, the heater 1240 has a first end section 1242, an intermediate section 1244, and a second end section 1246. The first end section 1242 and the second end section 1246 are configured to electrically connect to a power source when the capsule 1200 is loaded into the device body of an aerosol-generating device. When the heater 1240 is activated (e.g., so as to undergo Joule heating), the temperature of the aerosol-forming substrate may increase, and an aerosol may be generated and drawn or otherwise released through the first opening 1212 of the capsule 1200 before continuing downstream and exiting from the mouthpiece (e.g., replaceable mouthpiece 190).

The intermediate section 1244 of the heater 1240 may have a planar and winding form resembling a compressed oscillation or zigzag with a plurality of parallel segments (e.g., eight to sixteen parallel segments). Each parallel segment may have a width of about 0.28 mm-0.32 mm (e.g., 0.30 mm) and a spacing between parallel segments of about 0.30 mm-0.34 mm (e.g., 0.32 mm), although other dimensions are also possible. In an example embodiment, the intermediate section 1244 may occupy a rectangular area so as to more fully heat the chamber within the cover 1230. However, it should be understood that other forms for the intermediate section 1244 of the heater 1240 are also possible (e.g., spiral form, flower-like form). Additionally, the terminus of each of the first end section 1242 and the second end section 1246 may be oriented orthogonally to the plane of the intermediate section 1244. Furthermore, each of the first end section 1242 and the second end section 1246 may include a segment having a sideways, square J-shape which facilitates a transition from the plane of the intermediate section 1244 to the orthogonal plane of the electrical contact surfaces of the first end section 1242 and the second end section 1246. In this regard, the first end section 1242 and the second end section 1246 may also be viewed as resembling a pair of "feet" of the heater 1240. As a result, the first end section 1242 and the second end section 1246 may be embedded relatively securely within the second end cap 1220 while providing a pair of electrical contact surfaces (e.g., for engagement with the electrical contacts 152a and 152b of the aerosol-generating device 100).

FIG. 37 is a downstream perspective view of another capsule for an aerosol-generating device according to an example embodiment. FIG. 38 is an upstream end view of the capsule of FIG. 37. Generally, the capsule 1300 has commonalties (e.g., features, properties, materials of construction, methods of manufacture) with the capsule 200 and the capsule 1200. Thus, it should be understood that analogous aspects of the capsule 1300 may be the same as those disclosed in connection with the capsule 200 and the capsule 1200 unless otherwise indicated. Referring to FIGS. 37-38, the capsule 1300 has a housing configured to contain an aerosol-forming substrate (e.g., aerosol-forming substrate 1860' in FIG. 48) and a heater, wherein the downstream portion of the housing may be in the form of a first end cap 1310 (e.g., downstream cap). The upstream portion of the housing may be in the form of a second end cap 1320 (e.g., upstream cap, connector cap). The body portion of the housing may be in the form of a cover 1330 (e.g., shell, box sleeve).

The first end cap 1310 defines a first opening 1312, while the second end cap 1320 defines a second opening 1322. In an example embodiment, the first opening 1312 is in the form of a series of outlet openings (e.g., nine outlet openings), and the second opening 1322 is in the form of a series of inlet openings (e.g., eight inlet openings). In another instance, instead of being arranged in series, the openings may be arranged in an array of rows and columns. Additionally, each of the openings may have a width of about 0.26 mm-0.30 mm (e.g., 0.28 mm) to reduce or prevent the egress of particles of the aerosol-forming substrate. Although rectangular recesses are shown on the sides of the first end cap 1310 and the second end cap 1320, it should be understood that these features (e.g., gating features) are the result of a manufacturing process (e.g., injection molding) and may be omitted is some embodiments. Furthermore, the second end cap 1320 may expose a first end section 1342 and a second end section 1346 of a heater 1340 (e.g., FIG. 41). As illustrated, the second opening 1322 may be between the exposed portions of the first end section 1342 and the second end section 1346.

As shown in the drawings, the capsule 1300 has a shape wherein an end view or cross-section resembles a rectangle with a pair of opposing semicircular ends (e.g., elongated circle, obround, discorectangle, stadium, racetrack). The shape of the capsule 1300 may also be viewed as one wherein a cylinder has been diametrically elongated or flattened along its longitudinal axis. However, it should be understood that the capsule 1300 may have other suitable shapes. For example, in some instances, the capsule 1300 may have an ovoid or ellipsoid shape with an oval or elliptical cross-section. In other instances, the capsule 1300 may have a cuboid-like shape (e.g., rounded rectangular cuboid) with a rectangular cross-section. The chamber defined within the capsule 1300 may have the same or a different shape as the exterior of the capsule 1300. For instance, the cross-sections of the chamber and the exterior of the capsule 1300 may both be obround. In another instance, the cross-section of the chamber may be non-obround (e.g., rectangular), while the cross-section of the exterior of the capsule 1300 may be obround (or vice versa).

FIG. 39 is a cross-sectional view of the capsule of FIG. 37. Referring to FIG. 39, the intermediate section 1344 of the heater 1340 is an internal segment configured to heat an aerosol-forming substrate within the capsule 1300. It should be understood that the aerosol-forming substrate for the capsule 1300 may be the same as described in connection with the aerosol-forming substrate for the capsule 200 and the capsule 1200. The first end section 1342 and the second end section 1346 of the heater 1340 are external segments configured to establish an electrical connection with a power source (e.g., electrical connection with the power source 150 via the electrical contacts 152a and 152b).

In addition to the second opening 1322, the second end cap 1320 also defines an alignment recess 1326 and an inlet recess 1328. The alignment recess 1326 and the inlet recess 1328 may be viewed as being in a multi-level arrangement, wherein the base/inner end surface of the alignment recess 1326 (which exposes the first end section 1342 and the second end section 1346) may be regarded as being on one level, while the base/inner end surface of the inlet recess 1328 (or the grille-like surface of the second opening 1322) may be regarded as being on another level. The alignment recess 1326 is configured to facilitate a positioning of the capsule 1300 during its insertion into the device body of an aerosol-generating device. In an example embodiment, the alignment recess 1326 has angled sidewalls which taper inward toward the inlet recess 1328. With the angled sidewalls, the alignment recess 1326 may be quickly coupled with a corresponding engagement member of the device body with greater ease. For instance, when received within the capsule-receiving cavity 130 of the aerosol-generating device 100, the alignment recess 1326 of the capsule 1300 may be engaged with the angled surfaces 176, while the inlet recess 1328 of the capsule 1300 may be engaged with the capsule seal 202. As a result, the capsule 1300 may be properly loaded and aligned within the device body of the aerosol-generating device in a relatively consistent manner.

FIG. 40 is an exploded view of the capsule of FIG. 37. Referring to FIG. 40, the first end cap 1310 includes a first sealing ridge 1314, while the second end cap 1320 includes a second sealing ridge 1324. In an example embodiment, the first sealing ridge 1314 is in the form of a series of ribs (e.g., four ribs), and the second sealing ridge 1324 is in the form of a series of ribs (e.g., four ribs). In some instances, the ribs in each of the series may be of different heights to ensure a desired contact with the cover 1330. When the capsule 1300 is assembled, the first sealing ridge 1314 of the first end cap 1310 and the second sealing ridge 1324 of the second end cap 1320 are configured to interface with the inner surface of the cover 1330 (e.g., via an interference fit) to provide an air seal. As a result, when air is directed to the capsule 1300 during an operation of the aerosol-generating device, the air will enter the capsule 1300 via the inlet recess 1328 and the second opening 1322 in the second end cap 1320 (as opposed to entering the capsule 1300 via a gap between the second end cap 1320 and the cover 1330, wherein such air may essentially just flow along the inner surface of the cover 1330 so as to primarily bypass the aerosol-forming substrate and/or the intermediate section 1344 of the heater 1340). Similarly, with an appropriate seal, the aerosol generated within the chamber of the capsule 1300 will be drawn out through the first opening 1312 in the first end cap 1310 (as opposed to leaking out through a gap between the first end cap 1310 and the cover 1330).

The first end cap 1310 and the second end cap 1320 may be configured to include lead-in features to facilitate their introduction into the cover 1330. For instance, the first end cap 1310 may have a distal end with a periphery in a form of a tapered edge. Similarly, the second end cap 1320 may have a proximal end with a periphery in a form of a tapered edge. Such configurations may ease the insertions of the first end cap 1310 and the second end cap 1320 into the cover 1330 (e.g., via press fitting) during the assembly of the capsule 1300.

FIG. 41 is an isolated view of the heater in FIG. 40. Referring to FIG. 41, the heater 1340 includes a first end section 1342, an intermediate section 1344, and a second end section 1346. The intermediate section 1344 of the heater 1340 may have a planar and winding form resembling a compressed oscillation or zigzag with a plurality of parallel segments (e.g., eight to sixteen parallel segments). In an example embodiment, the two outermost parallel segments of the intermediate section 1344 may be wider than the inner parallel segments (e.g., 0.60 mm versus 0.30 mm) for thermal relief and mechanical stiffening. The inner parallel segments of the intermediate section 1344 may also be closer to the first opening 1312 in the first end cap 1310 and the second opening 1322 in the second end cap 1320 than the outer parallel segments of the intermediate section 1344. Such a configuration may promote heating in the center of the capsule 1300. However, it should be understood that other forms for the intermediate section 1344 of the heater 1340 are also possible (e.g., spiral form, flower-like form).

The terminus of each of the first end section 1342 and the second end section 1346 may be oriented orthogonally to the plane of the intermediate section 1344. Each of the first end section 1342 and the second end section 1346 may also include segments having a sideways J-shape. Furthermore, each of the first end section 1342 and the second end section 1346 may include opposing finger/claw-like structures. The finger/claw-like structures may serve as locating features for manufacturing equipment (e.g., overmolding tool). As a result, the first end section 1342 and the second end section 1346 may be embedded relatively securely within the second end cap 1320 while providing a pair of electrical contact surfaces.

Figure 42:
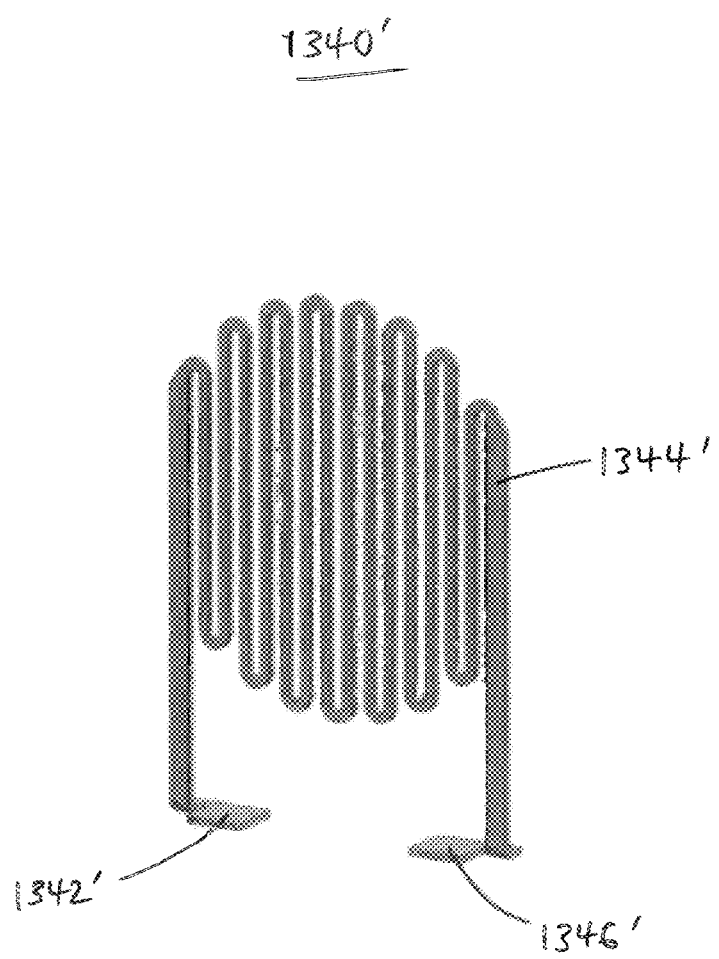
FIG. 42 is a perspective view of a variant of the heater of FIG. 41.

FIG. 42 is a perspective view of a variant of the heater of FIG. 41. Referring to FIG. 42, the heater 1340' includes a first end section 1342', an intermediate section 1344', and a second end section 1346'. The first end section 1342', the intermediate section 1344', and the second end section 1346' of the heater 1340' may be the same as described in connection with the first end section 1342, the intermediate section 1344, and the second end section 1346, respectively, of the heater 1340 unless indicated otherwise. For instance, with regard to differences, the transition from the intermediate section 1344' to the first end section 1342' and the second end section 1346' may involve little or no dimension change (e.g., uniform width versus the wider, thermal relief/lower resistance sections in FIG. 41). In addition, the first end section 1342' and the second end section 1346' may each include a simplified tab as the anchor structure and the electrical contact structure.

Figure 43:
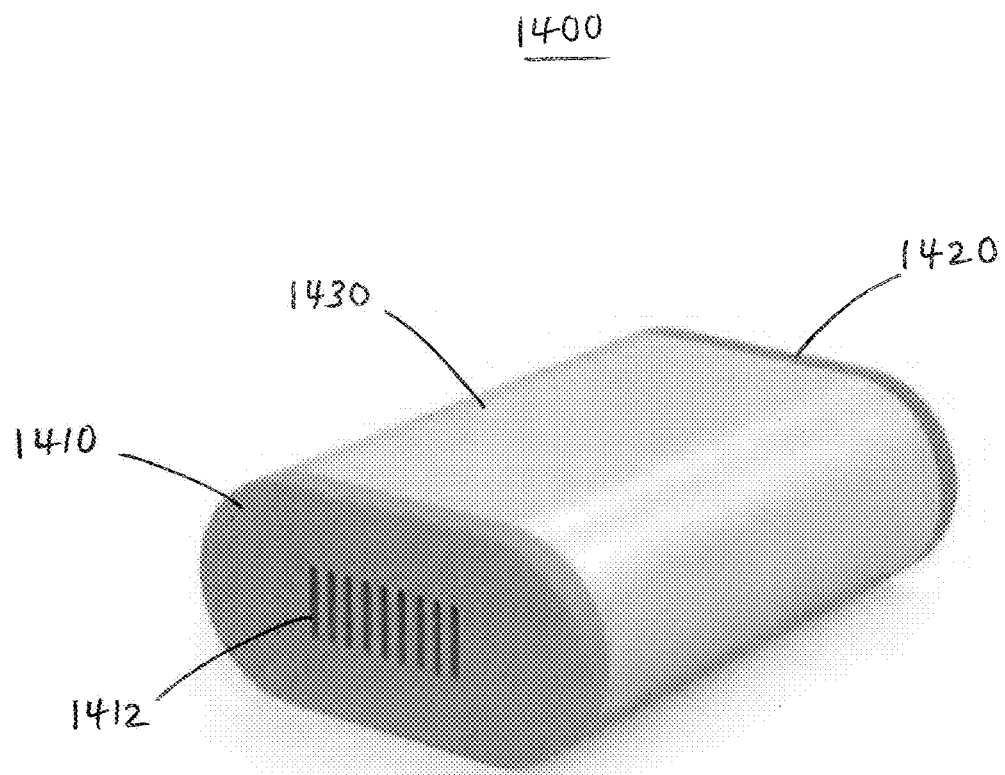
FIG. 43 is a downstream perspective view of another capsule for an aerosol-generating device according to an example embodiment.

FIG. 43 is a downstream perspective view of another capsule for an aerosol-generating device according to an example embodiment. Generally, the capsule 1400 has commonalties (e.g., features, properties, materials of construction, methods of manufacture) with the capsule 1300. Thus, it should be understood that analogous aspects of the capsule 1400 may be the same as those disclosed in connection with the capsule 1300 unless otherwise indicated. Referring to FIG. 43, the capsule 1400 has a housing with a downstream portion in the form of a first end cap 1410 (e.g., downstream cap) defining a first opening 1412, an upstream portion in the form of a second end cap 1420 (e.g., upstream cap, connector cap), and a body portion therebetween in the form of a cover 1430 (e.g., shell, box sleeve). With regard to alternatives to the shape shown, it should be understood that, in some instances, the capsule 1400 may instead have a cuboid-like shape (e.g., rounded rectangular cuboid) with a rectangular cross-section. In other instances, the capsule 1400 may have an ovoid or ellipsoid shape with an oval or elliptical cross-section. The chamber defined within the capsule 1400 may have the same or a different shape as the exterior of the capsule 1400. For instance, the cross-sections of the chamber and the exterior of the capsule 1400 may both be obround. In another instance, the cross-section of the chamber may be non-obround (e.g., rectangular), while the cross-section of the exterior of the capsule 1400 may be obround (or vice versa).

As illustrated, the sides of the first end cap 1410 and the second end cap 1420 may be devoid of rectangular recesses (e.g., gating features) present in some other embodiments (e.g., compare with capsule 1300 in FIG. 37) as a result of a manufacturing process. Additionally, although the side surfaces of the first end cap 1410 and the second end cap 1420 may be substantially flush with the adjacent/adjoining surfaces of the cover 1430, it should be understood that other variants are possible. For example, in some instances, the projecting edge/flange of the first end cap 1410 (which functions as a hard stop for the cover 1430) may be greater than the wall thickness of the cover 1430 such that the adjacent/adjoining surfaces of the first end cap 1410 and the cover 1430 are neither flush nor substantially flush. In other instances, the projecting edge/flange of the second end cap 1420 (which functions as a hard stop for the cover 1430) may be greater than the wall thickness of the cover 1430 such that the adjacent/adjoining surfaces of the second end cap 1420 and the cover 1430 are neither flush nor substantially flush. In yet other instances, both the projecting edges/flanges of the first end cap 1410 and the second end cap 1420 may be greater than the wall thickness of the cover 1430 such that the adjacent/adjoining surfaces of the first end cap 1410 and the cover 1430 are neither flush nor substantially flush, and the adjacent/adjoining surfaces of cover 1430 and the second end cap 1420 are neither flush nor substantially flush.

In another variation, the first end cap 1410 and/or the second end cap 1420 may be configured to be fully seated within the cover 1430. For example, the downstream end face of the first end cap 1410 may be flush (or slightly sub-flush) with the downstream rim of the cover 1430. Similarly, the upstream end face of the second end cap 1420 may be flush (or slightly sub-flush) with the upstream rim of the cover 1430.

Figure 44:
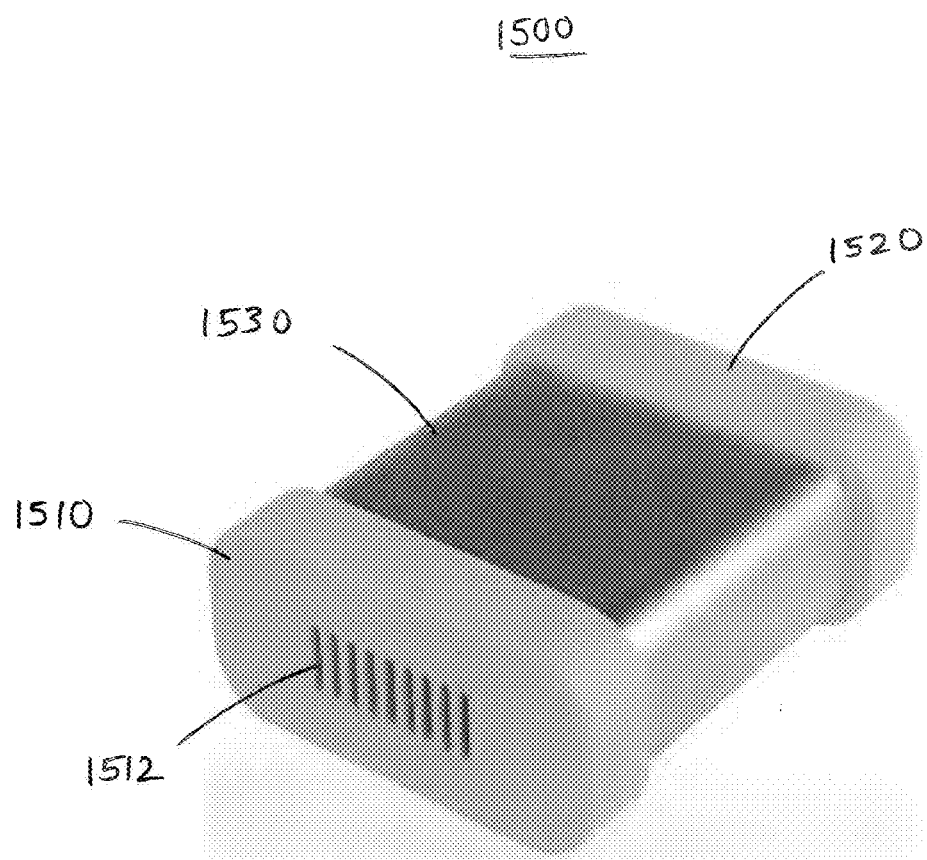
FIG. 44 is a downstream perspective view of another capsule for an aerosol-generating device according to an example embodiment.

FIG. 44 is a downstream perspective view of another capsule for an aerosol-generating device according to an example embodiment. Generally, the capsule 1500 has commonalties (e.g., features, properties, materials of construction, methods of manufacture) with the capsule 1300. Thus, it should be understood that analogous aspects of the capsule 1500 may be the same as those disclosed in connection with the capsule 1300 unless otherwise indicated. Referring to FIG. 44, the capsule 1500 has a housing with a downstream portion in the form of a first end cap 1510 (e.g., downstream cap) defining a first opening 1512, an upstream portion in the form of a second end cap 1520 (e.g., upstream cap, connector cap), and a body portion therebetween in the form of a cover 1530 (e.g., shell, box sleeve). With regard to alternatives to the shape shown, it should be understood that, in some instances, the capsule 1500 may instead have a shape wherein an end view or cross-section resembles a rectangle with a pair of opposing semicircular ends (e.g., elongated circle, obround, discorectangle, stadium, racetrack), an oval/ovoid, or an ellipse.

As illustrated, the first end cap 1510 and the second end cap 1520 may overlap with the cover 1530. Specifically, the periphery of each of the first end cap 1510 and the second end cap 1520 may be greater than the periphery of the cover 1530 so that the opposite ends of the cover 1530 can be received within the first end cap 1510 and the second end cap 1520. In such an instance, the first end cap 1510 and the second end cap 1520 may interface with the outer surface of the cover 1530. In another instance, the first end cap 1510 and the second end cap 1520 may interface with both the outer surface and the inner surface of the cover 1530. In either instance, the first end cap 1510 and the second end cap 1520 may include sealing ridges configured to interface with the cover 1530 to provide the desired air seal. Furthermore, the overlapping configuration of FIG. 44 may provide improved ergonomics by allowing the capsule 1500 to be grasped and handled with greater ease.

Figure 45:
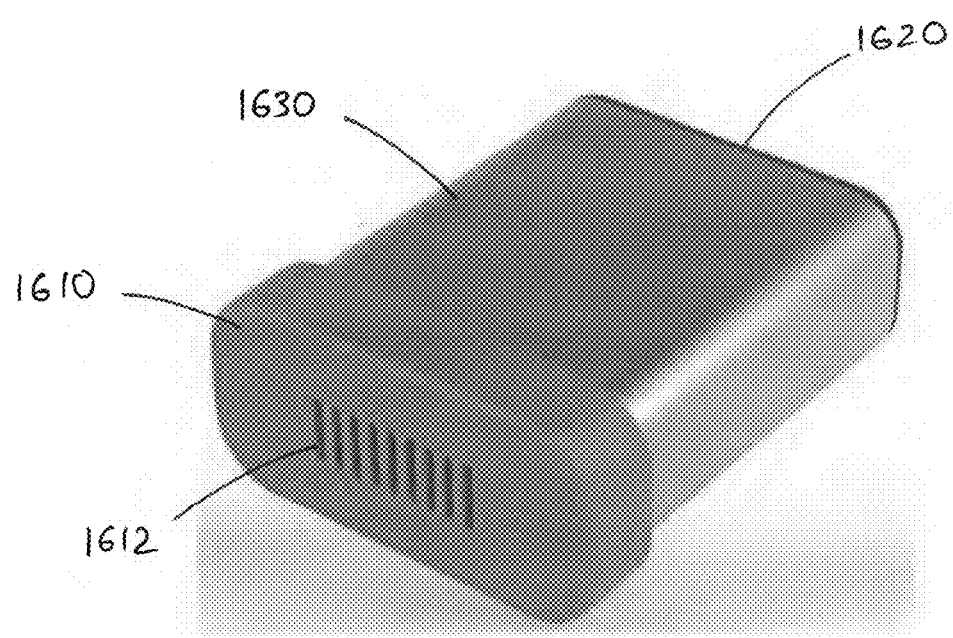
FIG. 45 is a downstream perspective view of another capsule for an aerosol-generating device according to an example embodiment.

FIG. 45 is a downstream perspective view of another capsule for an aerosol-generating device according to an example embodiment. Generally, the capsule 1600 has commonalties (e.g., features, properties, materials of construction, methods of manufacture) with the capsule 1500. Thus, it should be understood that analogous aspects of the capsule 1600 may be the same as those disclosed in connection with the capsule 1500 unless otherwise indicated. Referring to FIG. 45, the capsule 1600 has a housing with a downstream portion in the form of a first end cap 1610 (e.g., downstream cap) defining a first opening 1612, an upstream portion in the form of a second end cap 1620 (e.g., upstream cap, connector cap), and a body portion therebetween in the form of a cover 1630 (e.g., shell, box sleeve). With regard to alternatives to the shape shown, it should be understood that, in some instances, the capsule 1600 may instead have a shape wherein an end view or cross-section resembles a rectangle with a pair of opposing semicircular ends (e.g., elongated circle, obround, discorectangle, stadium, racetrack), an oval/ovoid, or an ellipse.

As illustrated, the first end cap 1610 may overlap with the cover 1630. Specifically, the periphery of the first end cap 1610 may be greater than the periphery of the cover 1630 so that the proximal end of the cover 1630 can be received within the first end cap 1610. In such an instance, the first end cap 1610 may interface with the outer surface of the cover 1630, while the second end cap 1620 may interface with the inner surface of the cover 1630. Conversely, in another instance, the first end cap 1610 may interface with the inner surface of the cover 1630, while the second end cap 1620 may interface with the outer surface of the cover 1630. In either instance, the first end cap 1610 and the second end cap 1620 may include sealing ridges configured to interface with the cover 1630 to provide the desired air seal. Furthermore, the overlapping configuration of FIG. 45, wherein the first end cap 1610 overlaps the cover 1630, may help to ensure a proper orientation of the capsule 1600 when loading into the device body of an aerosol-generating device (e.g., by limiting the possible orientation options for loading the capsule 1600).

Figure 46:
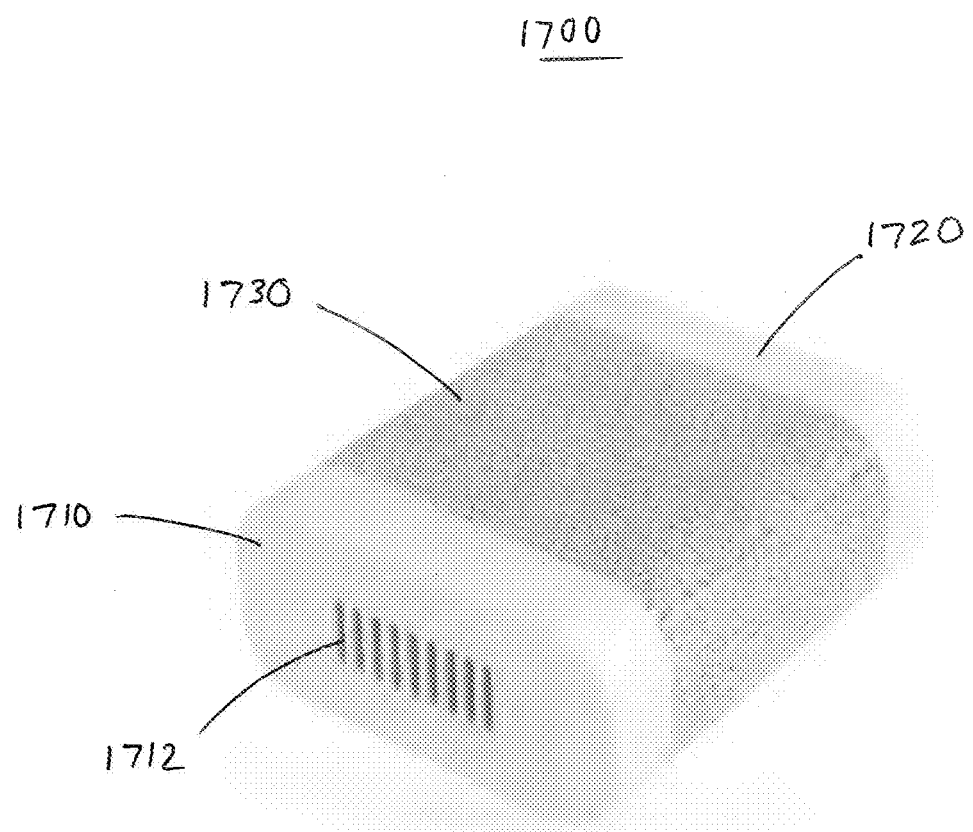
FIG. 46 is a downstream perspective view of another capsule for an aerosol-generating device according to an example embodiment.

FIG. 46 is a downstream perspective view of another capsule for an aerosol-generating device according to an example embodiment. Generally, the capsule 1700 has commonalties (e.g., features, properties, materials of construction, methods of manufacture) with the capsule 1500. Thus, it should be understood that analogous aspects of the capsule 1700 may be the same as those disclosed in connection with the capsule 1500 unless otherwise indicated. Referring to FIG. 46, the capsule 1700 has a housing with a downstream portion in the form of a first end cap 1710 (e.g., downstream cap) defining a first opening 1712, an upstream portion in the form of a second end cap 1720 (e.g., upstream cap, connector cap), and a body portion therebetween in the form of a cover 1730 (e.g., shell, box sleeve). With regard to alternatives to the shape shown, it should be understood that, in some instances, the capsule 1700 may instead have a shape wherein an end view or cross-section resembles a rectangle with a pair of opposing semicircular ends (e.g., elongated circle, obround, discorectangle, stadium, racetrack), an oval/ovoid, or an ellipse.

As illustrated, the cover 1730 may be a composite structure including an inner shell and an outer wrapper. The inner shell of the cover 1730 may be formed of a metal/alloy or a high-temperature plastic, while the outer wrapper of the cover 1730 may be formed of an insulating and/or fibrous material (e.g., pulp/cork wrapper, paper label). For instance, the material of the outer wrapper of the cover 1730 may be one that allows for printing (e.g., branding/aesthetics or other information). When the capsule 1700 is assembled, the side surfaces of the first end cap 1710 and the second end cap 1720 may be substantially flush with the adjacent/adjoining surfaces of the cover 1730. Furthermore, the composite structure of the cover 1730 may improve the thermal properties (e.g., heat insulating effect for safer handling) and/or the aesthetic characteristics of the capsule 1700.

Figure 47:
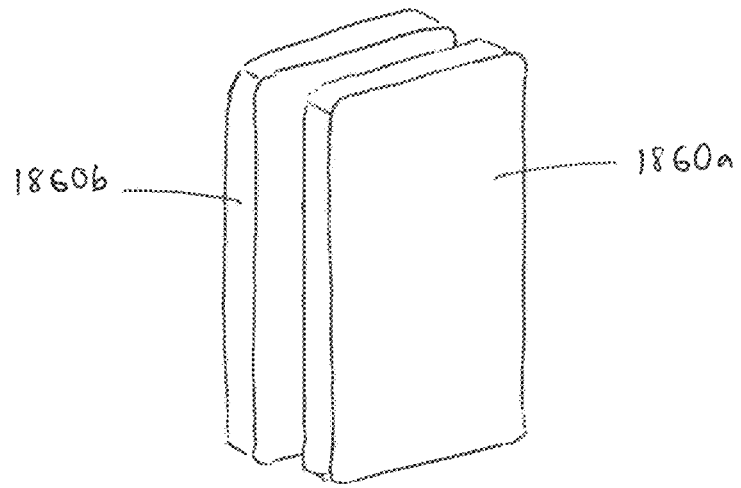
FIG. 47 is a perspective view of an aerosol-forming substrate in consolidated form according to an example embodiment.

FIG. 47 is a perspective view of an aerosol-forming substrate in consolidated form according to an example embodiment. Referring to FIG. 47, the aerosol-forming substrate 1860 may include a first aerosol-forming substrate 1860*a* and a second aerosol-forming substrate 1860*b* to facilitate substrate loading during an assembly of a capsule. Each of the first aerosol-forming substrate 1860*a* and the second aerosol-forming substrate 1860*b* may be in a consolidated form that is configured to maintain its shape so as to allow placement in a unified manner within the chamber of a capsule. For instance, the first aerosol-forming substrate 1860*a* and the second aerosol-forming substrate 1860*b* may be in the form of rectangular sheets/slabs dimensioned for insertion into the capsule 1200. Specifically, during assembly/loading, the first aerosol-forming substrate 1860*a* and the second aerosol-forming substrate 1860*b* may be inserted into the cover 1230 so as to be on respective sides of the intermediate section 1244 of the heater 1240 (e.g., sandwiching the intermediate section 1244 in between). Based on the shape and dimensions of the first aerosol-forming substrate 1860*a* and the second aerosol-forming substrate 1860*b*, the aerosol-forming substrate 1860 may occupy all or substantially all of the available space within the chamber defined by the interior surfaces of the first end cap 1210, the second end cap 1220, and the cover 1230.

Figure 48:
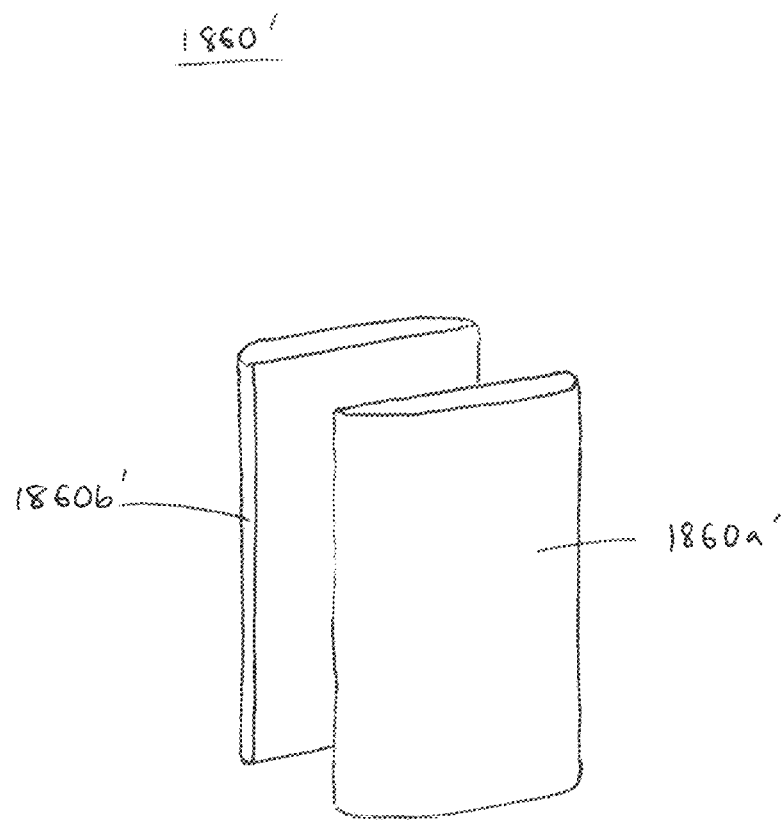
FIG. 48 is a perspective view of another aerosol-forming substrate in consolidated form according to an example embodiment.

FIG. 48 is a perspective view of another aerosol-forming substrate in consolidated form according to an example embodiment. Referring to FIG. 48, the aerosol-forming substrate 1860' may differ from the aerosol-forming substrate 1860 with regard to its shape and dimensions. Otherwise, the aerosol-forming substrate 1860' may be the same as described in connection with the aerosol-forming substrate 1860. As a result, analogous aspects that were already discussed may not have been repeated in the interest of brevity. The aerosol-forming substrate 1860' may include a first aerosol-forming substrate 1860*a*' and a second aerosol-forming substrate 1860*b*', wherein each may be in a consolidated form. For instance, the first aerosol-forming substrate 1860*a*' and the second aerosol-forming substrate 1860*b*' may be in the form slabs/pallets with a semi-obround cross-section dimensioned for insertion into the capsule 1300. Specifically, during assembly/loading, the first aerosol-forming substrate 1860*a*' and the second aerosol-forming substrate 1860*b*' may be inserted into the cover 1330 so as to be on respective sides of the intermediate section 1344 of the heater 1340 (e.g., sandwiching the intermediate section 1344 in between). Based on the shape and dimensions of the first aerosol-forming substrate 1860*a*' and the second aerosol-forming substrate 1860*b*', the aerosol-forming substrate 1860' may occupy all or substantially all of the available space within the chamber defined by the interior surfaces of the first end cap 1310, the second end cap 1320, and the cover 1330 (due to its resulting shape and dimensions having an obround cross-section that corresponds to the cross-section of the chamber).

Figure 49:
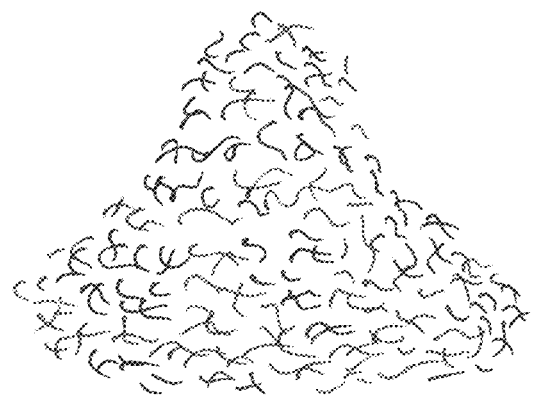
FIG. 49 is a perspective view of an aerosol-forming substrate in loose form according to an example embodiment.

FIG. 49 is a perspective view of an aerosol-forming substrate in loose form according to an example embodiment. Referring to FIG. 49, the aerosol-forming substrate 1860" may be in a loose form (e.g., particles, fibers, grounds, fragments, shreds) that does not have a set shape but rather is configured to take on the shape of an available space within a chamber when introduced into a capsule. Specifically, during assembly/loading, the loose form of the aerosol-forming substrate 1860" may partially or fully occupy the available space within a chamber of a capsule so as to be on respective sides of the intermediate section of the heater (e.g., so as to surround and contact the intermediate section 1344 of the heater 1340). For instance, the loose form of the aerosol-forming substrate 1860" may be used to fill in a remainder of a chamber (e.g., top off a chamber) that is already loaded with an aerosol-forming substrate in consolidated form. In another instance, the loose form of the aerosol-forming substrate 1860" may be used to fill the entirety of a chamber of a capsule. Furthermore, the aerosol-forming substrate 1860" may be loaded into capsule (e.g., capsule 1200, capsule 1300) via a vacuum-assisted process.

Figure 50:
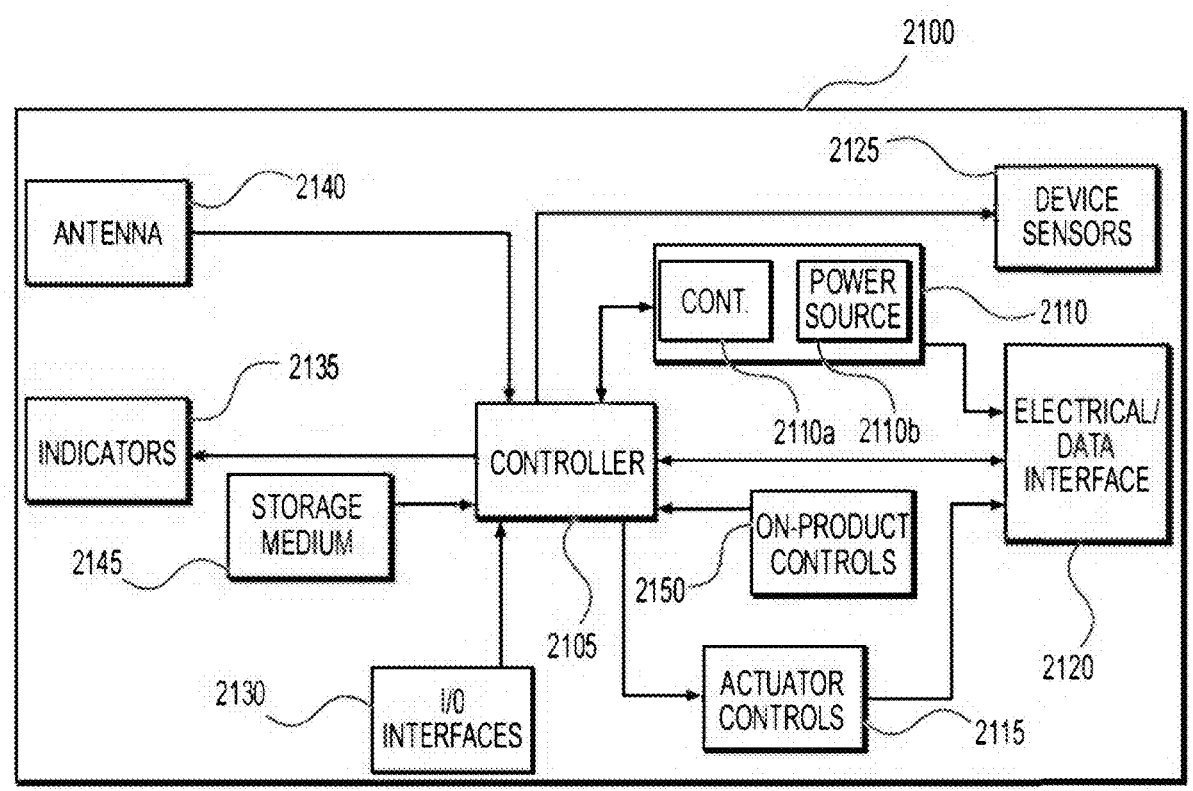
FIG. 50 is a block diagram of an aerosol-generating device according to an example embodiment.

FIG. 50 is a block diagram of an aerosol-generating device according to an example embodiment. In one instance, the aerosol-generating device may be the aerosol-generating device 100. In another instance, the aerosol-generating device may be the aerosol-generating device 500. Unless indicated otherwise, the details of the block diagram are applicable to both the aerosol-generating device 100 and the aerosol-generating device 500.

As shown in FIG. 50, according to at least one example embodiment, a control subsystem 2100 may include a controller 2105, a power supply 2110, actuator controls 2115, a capsule electrical/data interface 2120, device sensors 2125, input/output (I/O) interfaces 2130, aerosol indicators 2135, at least one antenna 2140, and/or a storage medium 2145, etc., but the example embodiments are not limited thereto. For example, the control subsystem 2100 may include additional elements. However, for the sake of brevity, the additional elements are not described. In other example embodiments, the capsule electrical/data interface 2120 may be an electrical interface only, etc.

The controller 2105 may be hardware including logic circuits; a hardware/software combination such as a processor executing software; or a combination thereof. For example, the controller 2105 may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

In the event where the controller 2105 is, or includes, a processor executing software, the controller 2105 is configured as a special purpose machine (e.g., a processing device) to execute the software, stored in memory accessible by the controller 2105 (e.g., the storage medium 2145 or another storage device), to perform the functions of the controller 2105. The software may be embodied as program code including instructions for performing and/or controlling any or all operations described herein as being performed by the controller 2105.

As disclosed herein, the term "storage medium", "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

The controller 2105 communicates with the power supply 2110, the actuator control 2115, the electrical/data interface 2120, the device sensors 2125, the input/output (I/O) interfaces 2130, the aerosol indicators 2135, on-product controls 2150, and/or the at least one antenna 2140, etc. According to at least some example embodiments, the on-product controls 2150 can include any device or devices capable of being manipulated manually by an adult operator to indicate a selection of a value. Example implementations include, but are not limited to, one or more buttons, a dial, a capacitive sensor, and a slider, etc.

The controller 2105 (or storage medium 2145) stores key material and proprietary algorithm software for the encryption. For example, encryption algorithms rely on the use of random numbers. The security of these algorithms depends on how truly random these numbers are. These numbers are usually pre-generated and coded into the processor or memory devices. Example embodiments may increase the randomness of the numbers used for the encryption by using the aerosol drawing parameters e.g., durations of instances of aerosol drawing, intervals between instances of aerosol drawing, or combinations of them, to generate numbers that are more random and more varying from individual to individual than pre-generated random numbers. All communications between the controller 2105 and the capsule 200 may be encrypted.

The controller 2105 is configured to operate a real time operating system (RTOS), control the control subsystem 2100 and may be updated through reading and/or sensing update information from a tag, chip, and/or label (e.g., a security tag, a security chip, etc.) included on the capsule 200, through communicating with the NVM or CC-NVM, and/or when the control subsystem 2100 is connected with other devices (e.g., a smart phone) through the I/O interfaces 2130 and/or the antenna 2140. For example, the update information may include parameter information related to the corresponding capsule, such as heater parameter information and/or heater profile information tailored and/or directed towards the aerosol-forming substrate contained within the installed capsule 200, capsule authentication update information with information relevant to the capsule authentication method (e.g., security settings related to the capsules, updates to the security keys used during authentication, etc.), programming updates, etc. Additionally, the I/O interfaces 2130 and the antenna 2140 allow the control subsystem 2100 to connect to various external devices such as smart phones, tablets, and PCs, etc. For example, the I/O interfaces 2130 may include a USB-C connector, a micro-USB connector, etc. The USB-C connector (e.g., connector port 114) may be used by the control subsystem 2100 to charge the power source 2110*b* (e.g., which may correspond to the power source 150), and may also be used to transmit and/or receive data from at least one external device, such as aerosol profiles, heater profiles, device performance log data (e.g., controller performance data, memory performance data, battery performance data, heater performance data, etc.), firmware upgrades, software upgrades, etc., but the example embodiments are not limited thereto.

The controller 2105 may include on-board RAM and flash memory to store and execute code including analytics, diagnostics and software upgrades. As an alternative, the storage medium 2145 may store the code. Additionally, in another example embodiment, the storage medium 2145 may be on-board the controller 2105.

The controller 2105 may further include on-board clock, reset and power management modules to reduce an area covered by a PCB in the device body housing.

The device sensors 2125 may include a number of sensor transducers that provide measurement information to the controller 2105. The device sensors 2125 may include a power supply temperature sensor, an external capsule temperature sensor, a current sensor for the heater, power supply current sensor, airflow sensor and an accelerometer to monitor movement and orientation. The power supply temperature sensor and external capsule temperature sensor may be a thermistor or thermocouple and the current sensor for the heater and power supply current sensor may be a resistive based sensor or another type of sensor configured to measure current. The air flow sensor (e.g., flow sensor 185) may be a pressure sensor (e.g., a capacitive pressure sensor, etc.) configured to detect positive or negative air pressure (e.g., a draw or a puff), a microelectromechanical system (MEMS) flow sensor, and/or another type of sensor configured to measure air flow such as a hot-wire anemometer. Further, instead of, or in addition to, measuring air flow using a flow sensor included in the device sensors 2125 of the control subsystem 2100 of the device body housing, air flow may be measured using a hot wire anemometer 2220A located in the capsule 200. According to at least one example embodiment, the device sensors 2125 further includes a capsule detection sensor for detecting the presence of the capsule in the aerosol-generating device 100, and/or a door detection sensor for detecting the closure of a door and/or lid of the aerosol-generating device, but the example embodiments are not limited thereto.

The data generated from one or more of the device sensors 2125 may be detected based on a binary signal (e.g., on/off signal) using a general purpose input/output (GPIO) circuit, etc., and/or may be sampled at a sample rate appropriate to the parameter being measured using, for example, a discrete, multi-channel analog-to-digital converter (ADC), etc.

Additionally, according to at least one example embodiment, the device sensors may further include a tag sensor, such as a barcode sensor, a secure element (SE) reader, an optical reader, a physical parameter reader, etc. The tag sensor and/or the tag antenna (e.g., RFID antenna, NFC antenna, etc.) may be used individually or in combination to detect information stored on a tag (e.g., a RFID tag, a NFC tag, a barcode tag, a SE, etc.) installed and/or attached to an exterior portion of the capsule 200, and/or may be used to detect and/or sense a physical parameter of the capsule 200, such as a resistance value of a heater included within the capsule 200, etc. The tag sensor and/or tag antenna may be arranged in physical proximity to a properly inserted capsule 200 such that information stored on the tag, such as electronic identity information, authentication information, hardware parameter information, aerosol-forming substrate information (such as aerosol-forming substrate expiration information, date of manufacture information, etc.), profile information, etc.

The controller 2105 may adapt heater profiles for an aerosol-forming substrate and other profiles based on the measurement information received from the controller 2105. For the sake of convenience, these are generally referred to as aerosol profiles. The heater profile identifies the power profile to be supplied to the heater during the few seconds when aerosol drawing takes place and/or the power profile to be supplied to the heater in between aerosol drawing instances in order to apply continual heating to the capsule (e.g., to provide an "oven mode" where a desired temperature is maintained within the capsule for a desired period of time). For example, a heater profile can deliver maximum power to the heater when an instance of aerosol drawing is initiated, but then after a second or so immediately reduce the power to half way or a quarter way. According to at least some example embodiments, the modulation of electrical power provided to the heater may be implemented using pulse width modulation, but is not limited thereto.

In addition, a heater profile can also be modified based on a detected draw and/or application of negative pressure on the aerosol-generating device 100. The use of the flow sensor allows aerosol drawing strength to be measured and used as feedback to the controller 2105 to adjust the power delivered to the heater of the capsule 200, which may be referred to as heating or energy delivery.

According to at least some example embodiments, when the controller 2105 recognizes the capsule 200 which is currently installed (e.g., via SKU, via a unique identifier included in a tag (e.g., RFID tag, NFC tag, etc.), etc.), the controller 2105 matches an associated heating profile that is designed for that particular capsule. The controller 2105 and the storage medium 2145 will store data and algorithms that allow the generation of heating profiles for all SKUs, capsule types, aerosol-forming substrate types, etc. In another example embodiment, the controller 2105 may read the heating profile from the capsule. Additionally, the adult operators may also adjust heating profiles to suit their preferences using the on-product controls 2150, using an external device wirelessly paired with the aerosol-generating device 100 and/or connected to the aerosol-generating device 100 via the I/O interfaces 2130, etc. In other example embodiments, the controller 2105 may use the heating profile applied for a previously installed capsule, which has been stored in memory, to a currently installed capsule on the assumption that the current capsule is of a same type as the previously installed capsule, etc.

The controller 2105 may send data to and receives data from the power supply 2110. The power supply 2110 includes a power source 2110b (e.g., which may correspond to the power source 150) and a power controller 2110a to manage the power output by the power source 2110b.

The power source 2110b may be a Lithium-ion battery or one of its variants, for example a lithium-ion polymer battery. Alternatively, the power source 2110b may be a Nickel-metal hydride battery, a Nickel cadmium battery, a Lithium-manganese battery, a Lithium-cobalt battery or a fuel cell. Alternatively, the power source 2110b may be rechargeable and include circuitry allowing the battery to be chargeable by an external charging device. In that case, the circuitry, when charged, provides power for a desired (or alternatively a pre-determined) number of instances of aerosol drawing, after which the circuitry must be re-connected to an external charging device.

The power controller 2110a provides commands to the power source 2110b based on instructions from the controller 2105. For example, the power supply 2110 may receive a command from the controller 2105 to provide power to the capsule (through the capsule electrical/data interface 2120) when the capsule is detected and the adult operator activates the control subsystem 2100 (e.g., by activating a switch such as a toggle button, capacitive sensor, IR sensor). Additionally, according to some example embodiments, the controller 2105 may transmit the command to the power supply 2110 based on the proper authentication of the capsule, but the example embodiments are not limited thereto.

In addition to supplying power to the capsule, the power supply 2110 also supplies power to the controller 2105. Moreover, the power controller 2110a may provide feedback to the controller 2105 indicating performance of the power source 2110b.

The controller 2105 sends data to and receives data from the at least one antenna 2140. The at least one antenna 2140 may include a NFC modem and a Bluetooth Low Energy (LE) modem and/or other modems for other wireless technologies (e.g., WiFi, etc.). In an example embodiment, the communications stacks are in the modems, but the modems are controlled by the controller 2105. The Bluetooth LE modem is used for data and control communications with an application on an external device (e.g., smart phone, etc.).

The NFC/Bluetooth LE/WiFi modem may be used for pairing of the aerosol-generating device 100 to the application and transmission of diagnostic information, data, profile information, capsule information, hardware parameter information, firmware updates, etc. Moreover, the Bluetooth LE/WiFi modem may be used to provide location information (for an adult operator to find the aerosol-generating device) or authentication during a purchase, etc.

As described above, the control subsystem 2100 may generate and adjust various profiles for aerosol generation. The controller 2105 uses the power supply 2110 and the actuator controls 2115 to regulate the profile for the adult operator.

The actuator controls 2115 include passive and active actuators to regulate a desired aerosol profile. For example, the device body housing may include actuators within an air inlet path and/or air inlet channel of the device body housing, such as within the air flow subsystem of the aerosol-generating device 100 (e.g., air channel assembly 181, the air hose 180, the air inlet connection 184, etc.). The actuator controls 2115 may control the flow of air within the air inlet channel using the actuators based on commands from the controller 2105 associated with the desired aerosol profile.

Moreover, the actuator controls 2115 are used to energize the heater in conjunction with the power supply 2110. More specifically, the actuator controls 2115 are configured to generate a drive waveform associated with the desired aerosol profile. As described above, each possible profile is associated with a drive waveform. Upon receiving a command from the controller 2105 indicating the desired aerosol profile, the actuator controls 2115 may produce the associated modulating waveform for the power supply 2110.

The controller 2105 supplies information to the aerosol indicators 2135 to indicate statuses and occurring operations to the adult operator. The indicators 2135 include a power indicator displayed on the display panel (e.g., communication screen 140), a separate indicator light (e.g., a LED indicator light, etc.) that may be activated when the controller 2105 senses a button pressed by the adult operator. The indicators 2135 may also include a haptic feedback motor, speaker, an indicator for a current state of an adult operator-controlled aerosol parameter (e.g., generated aerosol volume), and other feedback mechanisms.

A number of non-limiting examples of different capsules are disclosed herein. It should be understood that the relevant teachings/variants with regard to one capsule may be applicable to the other capsules unless indicated otherwise. In addition, although the aerosol-generating device 100 and the aerosol-generating device 500 are disclosed as being configured to receive and heat the capsule 200, it should be understood that the aerosol-generating device 100 and the aerosol-generating device 500 may also be adapted to receive and heat the capsule 1200, the capsule 1300, the capsule 1400, the capsule 1500, the capsule 1600, and the capsule 1700 as well as variants thereof.

While some example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

Although described with reference to specific examples and drawings, modifications, additions and substitutions of example embodiments may be variously made according to the description by those of ordinary skill in the art. For example, the described techniques may be performed in an order different with that of the methods described, and/or elements such as the described system, architecture, devices, circuit, and the like, may be connected or combined to be different from the above-described methods, or results may be appropriately achieved by other elements or equivalents.

The invention claimed is:

1. A capsule for an aerosol-generating device, comprising:
 a housing defining inlet openings, outlet openings, and a chamber between the inlet openings and the outlet openings;
 an aerosol-forming substrate within the chamber of the housing; and
 a heater in an upstream portion of the housing adjacent to the inlet openings, the upstream portion of the housing defining the inlet openings and an alignment recess.

2. The capsule of claim 1, wherein the housing has a longitudinal axis, and a longest dimension of the chamber extends along the longitudinal axis of the housing.

3. The capsule of claim 1, wherein the housing includes the upstream portion, a downstream portion, and a body portion between the upstream portion and the downstream portion.

4. The capsule of claim 3, wherein the body portion of the housing includes a proximal end and a distal end, the upstream portion of the housing configured to engage with the distal end of the body portion, the downstream portion of the housing configured to engage with the proximal end of the body portion.

5. The capsule of claim 3, wherein the downstream portion of the housing defines the outlet openings.

6. The capsule of claim 3, wherein the upstream portion, the downstream portion, and the body portion jointly define the chamber within the housing.

7. The capsule of claim 3, wherein the upstream portion and the downstream portion are configured to engage with inner surfaces of the body portion.

8. The capsule of claim 3, wherein the upstream portion and the downstream portion include sealing ridges extending around exterior sidewalls of the upstream portion and the downstream portion.

9. The capsule of claim 1, wherein the heater is embedded in the upstream portion of the housing.

10. The capsule of claim 1, wherein the upstream portion of the housing exposes end sections of the heater.

11. The capsule of claim 1, wherein the upstream portion of the housing further defines an inlet recess, the inlet recess being downstream from the alignment recess and upstream from the inlet openings.

12. The capsule of claim 3, wherein the upstream portion of the housing is in a form of an upstream cap, the downstream portion of the housing is in a form of a downstream cap, and the body portion of the housing is in a form of a sleeve.

13. The capsule of claim 3, wherein the body portion of the housing is formed of a plant material.

14. The capsule of claim 3, wherein the body portion of the housing has a multi-layer structure including an underlying conductive layer and an overlying insulating layer.

15. The capsule of claim 1, wherein the aerosol-forming substrate includes a plant material.

16. The capsule of claim 15, wherein the plant material includes tobacco.

17. The capsule of claim 1, wherein the heater includes a first end section, an intermediate section, and a second end section, the first end section and the second end section being external to the chamber.

18. The capsule of claim 17, wherein the intermediate section of the heater is disposed within the aerosol-forming substrate in the chamber.

19. The capsule of claim 17, wherein the intermediate section of the heater has a planar and winding form.

20. The capsule of claim 17, wherein the intermediate section of the heater includes a plurality of parallel segments extending along a longest dimension of the chamber.

* * * * *